US012428407B2

(12) United States Patent
Lee et al.

(10) Patent No.: US 12,428,407 B2
(45) Date of Patent: Sep. 30, 2025

(54) ORGANIC ELECTROLUMINESCENT COMPOUND AND ORGANIC ELECTROLUMINESCENT DEVICE INCLUDING THE SAME

(71) Applicant: SFC CO., LTD, Cheongju-si (KR)

(72) Inventors: Se-jin Lee, Cheongju-si (KR); Si-In Kim, Cheongju-si (KR); Seok-bae Park, Cheongju-si (KR); Hee-dae Kim, Cheongju-si (KR); Yeong-tae Choi, Cheongju-si (KR); Seung-soo Lee, Cheongju-si (KR); Ji-yung Kim, Cheongju-si (KR); Kyeong-hyeon Kim, Cheongju-si (KR); Kyung-tae Kim, Cheongju-si (KR); Myeong-jun Kim, Cheongju-si (KR); Tae-gyun Lee, Cheongju-si (KR); Joon-ho Kim, Cheongju-si (KR)

(73) Assignee: SFC CO., LTD, Cheongju-si (KR)

(*) Notice: Subject to any disclaimer, the term of this patent is extended or adjusted under 35 U.S.C. 154(b) by 967 days.

(21) Appl. No.: 17/543,996

(22) Filed: Dec. 7, 2021

(65) Prior Publication Data
US 2022/0181559 A1 Jun. 9, 2022

(30) Foreign Application Priority Data

Dec. 8, 2020 (KR) .................. 10-2020-0170555
Jun. 2, 2021 (KR) .................. 10-2021-0071356

(51) Int. Cl.
| | | |
|---|---|---|
| H01L 51/54 | (2006.01) | |
| C07D 307/79 | (2006.01) | |
| C07D 407/04 | (2006.01) | |
| C07D 409/10 | (2006.01) | |
| C09K 11/06 | (2006.01) | |
| H10K 85/30 | (2023.01) | |
| H10K 85/60 | (2023.01) | |
| H10K 50/11 | (2023.01) | |
| H10K 101/00 | (2023.01) | |

(52) U.S. Cl.
CPC ......... *C07D 407/04* (2013.01); *C07D 307/79* (2013.01); *C07D 409/10* (2013.01); *C09K 11/06* (2013.01); *H10K 85/322* (2023.02); *H10K 85/6574* (2023.02); *H10K 85/6576* (2023.02); *H10K 85/658* (2023.02); *C09K 2211/1018* (2013.01); *H10K 50/11* (2023.02); *H10K 2101/90* (2023.02)

(58) Field of Classification Search
None
See application file for complete search history.

(56) References Cited

U.S. PATENT DOCUMENTS

| 2011/0121269 A1* | 5/2011 | Lecloux ................. C07C 15/28 |
| | | 564/426 |
| 2017/0342318 A1 | 11/2017 | Kim et al. |
| 2020/0227639 A1* | 7/2020 | Yamatani ............... C09K 11/06 |

FOREIGN PATENT DOCUMENTS

| CN | 107004776 A | 8/2017 |
|---|---|---|
| EP | 3 660 024 A1 | 6/2020 |
| JP | 2005-47868 A | 2/2005 |
| JP | 2007-186449 A | 7/2007 |
| JP | 2009-203203 A | 9/2009 |
| JP | 2009-283899 A | 12/2009 |
| JP | 2012-522042 A | 9/2012 |
| JP | 2020-83896 A | 6/2020 |
| KR | 10-2014-0058290 A | 5/2014 |
| KR | 10-2016-0081531 A | 7/2016 |
| KR | 10-2019-0056338 A | 5/2019 |
| KR | 10-2094830 B1 | 3/2020 |
| KR | 10-2020-0047400 A | 5/2020 |
| KR | 10-2020-0066208 A | 6/2020 |
| KR | 10-2148296 B1 | 8/2020 |
| KR | 10-2022-0042160 A | 4/2022 |
| KR | 10-2022-0126245 A | 9/2022 |
| WO | WO 2020/085829 A1 | 4/2020 |

OTHER PUBLICATIONS

Korean Office Action issued on Nov. 1, 2021, in counterpart Korean Patent Application No. 10-2021-0071356 (7 pages in Korean).
Extended European search report issued on Apr. 13, 2022, in counterpart European Patent Application No. 21212082.8 (6 pages in English).
Tsuji, Hayato et al., "The Hydrogen/Deuterium Isotope Effect of the Host Material on the Lifetime of Organic Light-Emitting Diodes," The Royal Society of Chemistry, Chem Communication, Sep. 15, 2014, (pp. 14870-14872).
Japanese Office Action Issued on Dec. 20, 2022, in Counterpart Japanese Patent Application No. 2021-199176 (2 Pages in Japanese).
Korean Office Action Issued on Mar. 22, 2023, in Counterpart Korean Patent Application No. 10-2023-0020927 (12 Pages in Korean).
Chinese Office Action issued on Jul. 9, 2023, in counterpart Chinese Patent Application No. 202111479829.0 (8 pages in English, 6 pages in Chinese).

(Continued)

*Primary Examiner* — Andrew K Bohaty
(74) *Attorney, Agent, or Firm* — NSIP Law

(57) ABSTRACT

Disclosed are an anthracene derivative with a specific structure and an organic electroluminescent device including the anthracene derivative. The organic electroluminescent device includes a light emitting layer employing the anthracene derivative as a host compound and a polycyclic aromatic derivative with a specific structure as a dopant compound. The use of the host and dopant compounds allows the organic electroluminescent device to have a long lifetime and significantly improved low-voltage characteristics.

20 Claims, No Drawings

(56) References Cited

OTHER PUBLICATIONS

European Third Party Observations against EP 4011872 A1 issued on Sep. 25, 2023, in counterpart European Patent Application No. 21212082.8 (22 pages).

* cited by examiner

ORGANIC ELECTROLUMINESCENT COMPOUND AND ORGANIC ELECTROLUMINESCENT DEVICE INCLUDING THE SAME

CROSS REFERENCE TO RELATED APPLICATIONS

This application claims the benefit under 35 U.S.C. § 119(a) of Korean Patent Application No. 10-2020-0170555 filed on Dec. 8, 2020 and Korean Patent Application No. 10-2021-0071356 filed on Jun. 2, 2021, in the Korean Intellectual Property Office, the entire disclosure of which is incorporated herein by reference for all purposes.

BACKGROUND OF THE INVENTION

1. Field of the Invention

The present invention relates to an organic electroluminescent compound and an organic electroluminescent device including the same. More specifically, the present invention relates to an organic electroluminescent device in which an anthracene derivative with a specific structure as a host compound and a polycyclic aromatic derivative as a dopant compound are employed in a light emitting layer, achieving a long lifetime and significantly improved low-voltage characteristics of the device.

2. Description of the Related Art

Organic electroluminescent devices are self-luminous devices in which electrons injected from an electron injecting electrode (cathode) recombine with holes injected from a hole injecting electrode (anode) in a light emitting layer to form excitons, which emit light while releasing energy. Such organic electroluminescent devices have the advantages of low driving voltage, high luminance, large viewing angle, and short response time and can be applied to full-color light emitting flat panel displays. Due to these advantages, organic electroluminescent devices have received attention as next-generation light sources.

The above characteristics of organic electroluminescent devices are achieved by structural optimization of organic layers of the devices and are supported by stable and efficient materials for the organic layers, such as hole injecting materials, hole transport materials, light emitting materials, electron transport materials, electron injecting materials, and electron blocking materials. However, more research still needs to be done to develop structurally optimized structures of organic layers for organic electroluminescent devices and stable and efficient materials for organic layers of organic electroluminescent devices.

Particularly, for maximum efficiency in a light emitting layer, an appropriate combination of energy band gaps of a host and a dopant is required such that holes and electrons migrate to the dopant through stable electrochemical paths to form excitons.

SUMMARY OF THE INVENTION

Thus, the present invention intends to provide an organic electroluminescent device in which specific host and dopant materials are employed in a light emitting layer, achieving significantly improved low-voltage driving and life characteristics of the device.

One aspect of the present invention provides a compound as a host compound for an organic layer, preferably a light emitting layer of a device, represented by Formula A:

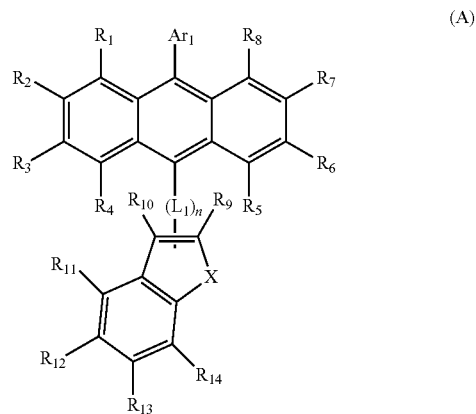

(A)

Structural features of Formula A and specific compounds that can be represented by Formula A are described below, and $Ar_1$, $R_1$ to $R_{14}$, $L_1$, and X in Formula A are as defined below.

Another aspect of the present invention provides an organic electroluminescent device including a first electrode, a second electrode opposite to the first electrode, and a light emitting layer interposed between the first and second electrodes wherein the light emitting layer includes the compound represented by Formula A.

The light emitting layer of the organic electroluminescent device further includes a dopant compound represented by Formula D-1 or D-2:

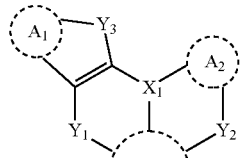

(D-1)

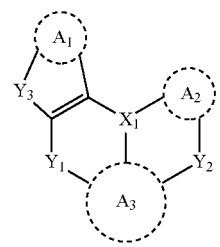

(D-2)

Structural features of Formulae D-1 and D-2 and specific compounds that can be represented by Formulae D-1 and D-2 are described below, and $X_1$, $Y_1$ to $Y_3$, and $A_1$ to $A_3$ in Formulae D-1 and D-2 are as defined below.

The organic electroluminescent device of the present invention includes a light emitting layer employing an anthracene derivative with a specific structure as a host and a polycyclic aromatic derivative as a dopant. The use of the host and dopant ensures significantly improved life and low-voltage driving characteristics of the device. Due to these advantages, the organic electroluminescent device of the present invention can find useful applications in not only lighting systems but also a variety of displays, including flat panel displays, flexible displays, and wearable displays.

The present invention will now be described in more detail.

One aspect of the present invention is directed to a compound represented by Formula A:

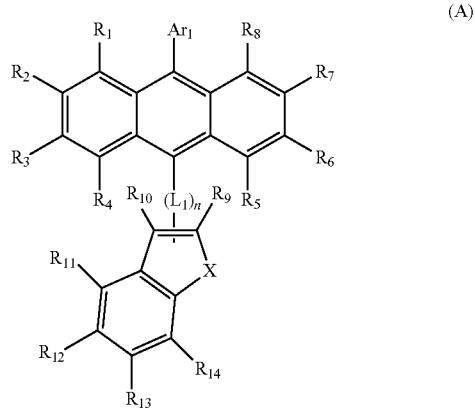

(A)

wherein $Ar_1$ is selected from substituted or unsubstituted $C_6$-$C_{50}$ aryl, substituted or unsubstituted $C_2$-$C_{50}$ heteroaryl, and substituted or unsubstituted $C_3$-$C_{50}$ mixed aliphatic-aromatic cyclic groups, $R_1$ to $R_{14}$ are identical to or different from each other and are each independently selected from hydrogen, deuterium, substituted or unsubstituted $C_1$-$C_{30}$ alkyl, substituted or unsubstituted $C_6$-$C_{50}$ aryl, substituted or unsubstituted $C_2$-$C_{30}$ alkenyl, substituted or unsubstituted $C_2$-$C_{30}$ alkynyl, substituted or unsubstituted $C_3$-$C_{30}$ cycloalkyl, substituted or unsubstituted $C_3$-$C_{30}$ cycloalkenyl, substituted or unsubstituted $C_2$-$C_{50}$ heteroaryl, substituted or unsubstituted $C_2$-$C_{30}$ heterocycloalkyl, substituted or unsubstituted $C_1$-$C_{30}$ alkoxy, substituted or unsubstituted $C_6$-$C_{50}$ aryloxy, substituted or unsubstituted $C_1$-$C_{30}$ alkylthioxy, substituted or unsubstituted $C_6$-$C_{50}$ arylthioxy, substituted or unsubstituted $C_1$-$C_{30}$ alkylamine, substituted or unsubstituted $C_6$-$C_{50}$ arylamine, substituted or unsubstituted $C_1$-$C_{30}$ alkylsilyl, substituted or unsubstituted $C_6$-$C_{50}$ arylsilyl, substituted or unsubstituted $C_3$-$C_{50}$ mixed aliphatic-aromatic cyclic groups, cyano, nitro, and halogen, with the proviso that one of $R_9$ and $R_{10}$ is bonded to $L_1$, X is an oxygen (O) or sulfur atom (S), $L_1$ is a divalent linker and is a single bond or is selected from substituted or unsubstituted $C_6$-$C_{50}$ arylene, substituted or unsubstituted $C_2$-$C_{50}$ heteroarylene, and substituted or unsubstituted $C_3$-$C_{50}$ mixed aliphatic-aromatic cyclic groups, and n is an integer from 1 to 3, provided that when n is 2 or more, the linkers $L_1$ are identical to or different from each other.

The compound of Formula A contains at least one benzofuran or benzothiophene moiety in its structure. The use of the compound of Formula A as a host compound in a light emitting layer of an organic electroluminescent device allows the organic electroluminescent device to have a long lifetime and improved low-voltage characteristics.

As used herein, the term "substituted" in the definition of $Ar_1$, $R_1$ to $R_{14}$, and $L_1$ indicates substitution with one or more substituents selected from deuterium, cyano, halogen, hydroxyl, nitro, $C_1$-$C_{24}$ alkyl, $C_1$-$C_{24}$ haloalkyl, $C_3$-$C_{30}$ cycloalkyl, $C_2$-$C_{24}$ alkenyl, $C_2$-$C_{24}$ alkynyl, $C_1$-$C_{24}$ heteroalkyl, $C_6$-$C_{30}$ aryl, $C_7$-$C_{30}$ arylalkyl, $C_7$-$C_{30}$ alkylaryl, $C_2$-$C_{30}$ heteroaryl, $C_2$-$C_{30}$ heteroarylalkyl, $C_1$-$C_{24}$ alkoxy, $C_1$-$C_{24}$ alkylamino, $C_6$-$C_{30}$ arylamino, $C_2$-$C_{30}$ heteroarylamino, $C_1$-$C_{24}$ alkylsilyl, $C_6$-$C_{30}$ arylsilyl, $C_6$-$C_{30}$ aryloxy, and $C_3$-$C_{30}$ mixed aliphatic-aromatic cyclic groups. The term "unsubstituted" in the same definition indicates having no substituent.

The compound of Formula A contains at least one deuterium atom (D). That is, at least one of $Ar_1$, $R_1$ to $R_{14}$, and $L_1$ in Formula A or at least one of the substituents of $Ar_1$, $R_1$ to $R_{14}$, and $L_1$ is deuterium.

According to one embodiment of the present invention, the degree of deuteration of the anthracene derivative represented by Formula A is at least 10%, indicating that at least 10% of the substituents introduced on the backbone of the compound represented by Formula A are deuterium atoms.

According to one embodiment of the present invention, the degree of deuteration of the anthracene derivative represented by Formula A is at least 30%.

The degree of deuteration of the anthracene derivative represented by Formula A is at least 50%.

According to one embodiment of the present invention, at least one of $R_{11}$ to $R_{14}$ may be selected from substituted or unsubstituted $C_6$-$C_{20}$ aryl, substituted or unsubstituted $C_3$-$C_{20}$ cycloalkyl, and substituted or unsubstituted $C_3$-$C_{20}$ heteroaryl.

According to one embodiment of the present invention, at least one of $R_{11}$ to $R_{14}$ in Formula A may be substituted or unsubstituted deuterated $C_6$-$C_{20}$ aryl, substituted or unsubstituted deuterated $C_3$-$C_{20}$ cycloalkyl or substituted or unsubstituted deuterated $C_3$-$C_{20}$ heteroaryl.

According to one embodiment of the present invention, the anthracene derivative represented by Formula A may be a compound represented by Formula A-1:

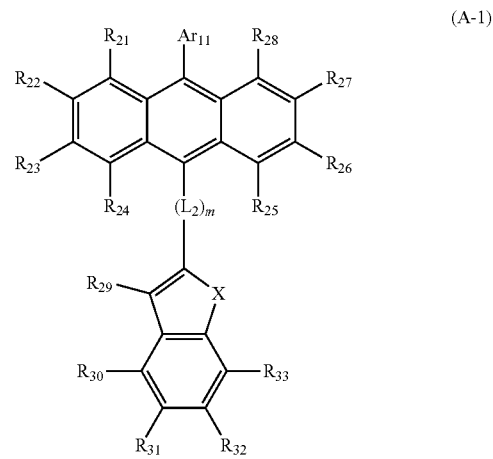

(A-1)

wherein $Ar_{11}$ is selected from substituted or unsubstituted $C_6$-$C_{50}$ aryl, substituted or unsubstituted $C_2$-$C_{50}$ heteroaryl, and substituted or unsubstituted $C_3$-$C_{50}$ mixed aliphatic-aromatic cyclic groups, $R_{21}$ to $R_{33}$ are identical to or different from each other and are each independently selected from hydrogen, deuterium, substituted or unsubstituted $C_1$-$C_{30}$ alkyl, substituted or unsubstituted $C_6$-$C_{50}$ aryl, substituted or unsubstituted $C_2$-$C_{30}$ alkenyl, substituted or unsubstituted $C_2$-$C_{30}$ alkynyl, substituted or unsubstituted $C_3$-$C_{30}$ cycloalkyl, substituted or unsubstituted $C_3$-$C_{30}$ cycloalkenyl, substituted or unsubstituted $C_2$-$C_{50}$ heteroaryl, substituted or unsubstituted $C_2$-$C_{30}$ heterocycloalkyl, substituted or unsubstituted $C_1$-$C_{30}$ alkoxy, substituted or unsubstituted $C_6$-$C_{50}$ aryloxy, substituted or unsubstituted $C_1$-$C_{30}$ alkylthioxy, substituted or unsubstituted $C_6$-$C_{50}$ arylthioxy, substituted or unsubstituted $C_1$-$C_{30}$ alkylamine, substituted or unsubstituted $C_6$-$C_{50}$ arylamine, substituted or unsubstituted $C_1$-$C_{30}$ alkylsilyl, substituted or unsubstituted $C_6$-$C_{50}$ arylsilyl, substituted or unsubstituted $C_3$-$C_{50}$ mixed aliphatic-aromatic cyclic groups, cyano, nitro, and halogen, X is an oxygen (O) or sulfur atom (S), $L_2$ is a divalent linker and is a single bond or is selected from substituted or unsubstituted $C_6$-$C_{50}$ arylene, substituted or unsubstituted $C_2$-$C_{50}$ heteroarylene, and substituted or unsubstituted $C_3$-$C_{50}$ mixed aliphatic-aromatic cyclic groups, and m is an integer from 1 to 3, provided that when m is 2 or more, the linkers $L_1$ are identical to or different from each other, or Formula A-2:

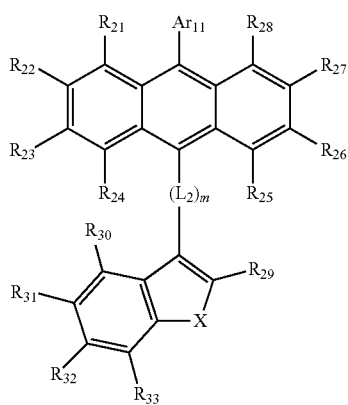

(A-2)

wherein $Ar_{11}$, $R_{21}$ to $R_{33}$, X, $L_2$, and m are as defined in Formula A-1.

As used herein, the term "substituted" in the definition of $Ar_{11}$, $R_{21}$ to $R_{33}$, and $L_2$ indicates substitution with one or more substituents selected from deuterium, cyano, halogen, hydroxyl, nitro, $C_1$-$C_{24}$ alkyl, $C_1$-$C_{24}$ haloalkyl, $C_3$-$C_{30}$ cycloalkyl, $C_2$-$C_{24}$ alkenyl, $C_2$-$C_{24}$ alkynyl, $C_1$-$C_{24}$ heteroalkyl, $C_6$-$C_{30}$ aryl, $C_7$-$C_{30}$ arylalkyl, $C_7$-$C_{30}$ alkylaryl, $C_2$-$C_{30}$ heteroaryl, $C_2$-$C_{30}$ heteroarylalkyl, $C_1$-$C_{24}$ alkoxy, $C_1$-$C_{24}$ alkylamino, $C_6$-$C_{30}$ arylamino, $C_2$-$C_{30}$ heteroarylamino, $C_1$-$C_{24}$ alkylsilyl, $C_6$-$C_{30}$ arylsilyl, $C_6$-$C_{30}$ aryloxy, and $C_3$-$C_{30}$ mixed aliphatic-aromatic cyclic groups. The term "unsubstituted" in the same definition indicates having no substituent.

Each of the compounds of Formulae A-1 and A-2 contains at least one deuterium atom (D). That is, at least one of $Ar_1$, $R_{21}$ to $R_{33}$, and $L_2$ in each of Formulae A-1 and A-2 or at least one of the substituents of $Ar_1$, $R_{21}$ to $R_{33}$, and $L_2$ is deuterium.

In the "substituted or unsubstituted $C_1$-$C_{30}$ alkyl", "substituted or unsubstituted $C_6$-$C_{50}$ aryl", etc., the number of carbon atoms in the alkyl or aryl group indicates the number of carbon atoms constituting the unsubstituted alkyl or aryl moiety without considering the number of carbon atoms in the substituent(s). For example, a phenyl group substituted with a butyl group at the para-position corresponds to a $C_6$ aryl group substituted with a $C_4$ butyl group.

As used herein, the expression "form a ring with an adjacent substituent" means that the corresponding substituent combines with an adjacent substituent to form a substituted or unsubstituted alicyclic or aromatic ring and the term "adjacent substituent" may mean a substituent on an atom directly attached to an atom substituted with the corresponding substituent, a substituent disposed sterically closest to the corresponding substituent or another substituent on an atom substituted with the corresponding substituent. For example, two substituents substituted at the ortho position of a benzene ring or two substituents on the same carbon in an aliphatic ring may be considered "adjacent" to each other.

In the present invention, the alkyl groups may be straight or branched. The number of carbon atoms in the alkyl groups is not particularly limited but is preferably from 1 to 20. Specific examples of the alkyl groups include, but are not limited to, methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 2-methylpentyl, 4-methylhexyl, and 5-methylhexyl groups.

The alkenyl group is intended to include straight and branched ones and may be optionally substituted with one or more other substituents. The alkenyl group may be specifically a vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, stilbenyl or styrenyl group but is not limited thereto.

The alkynyl group is intended to include straight and branched ones and may be optionally substituted with one or more other substituents. The alkynyl group may be, for example, ethynyl or 2-propynyl but is not limited thereto.

The cycloalkyl group is intended to include monocyclic and polycyclic ones and may be optionally substituted with one or more other substituents. As used herein, the term "polycyclic" means that the cycloalkyl group may be directly attached or fused to one or more other cyclic groups. The other cyclic groups may be cycloalkyl groups and other examples thereof include heterocycloalkyl, aryl, and heteroaryl groups. The cycloalkyl group may be specifically a cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl or cyclooctyl group but is not limited thereto.

The heterocycloalkyl group is intended to include monocyclic and polycyclic ones interrupted by a heteroatom such as O, S, Se, N or Si and may be optionally substituted with one or more other substituents. As used herein, the term "polycyclic" means that the heterocycloalkyl group may be directly attached or fused to one or more other cyclic groups. The other cyclic groups may be heterocycloalkyl groups and other examples thereof include cycloalkyl, aryl, and heteroaryl groups.

The aryl groups may be monocyclic or polycyclic ones. Examples of the monocyclic aryl groups include, but are not limited to, phenyl, biphenyl, terphenyl, and stilbenyl groups. Examples of the polycyclic aryl groups include naphthyl, anthracenyl, phenanthrenyl, pyrenyl, perylenyl, tetracenyl, chrysenyl, fluorenyl, acenaphathcenyl, triphenylene, and fluoranthrene groups but the scope of the present invention is not limited thereto.

The heteroaryl groups refer to heterocyclic groups interrupted by one or more heteroatoms. Examples of the heteroaryl groups include, but are not limited to, thiophene, furan, pyrrole, imidazole, triazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phthalazinyl, pyridopyrimidinyl, pyridopyrazinyl, pyrazinopyrazinyl, isoquinoline, indole, carbazole, benzoxazole, benzimidazole, benzothiazole, benzocarbazole, benzothiophene, dibenzothiophene, benzofuranyl, dibenzofuranyl, phenanthroline, thiazolyl, isoxazolyl, oxadiazolyl, thiadiazolyl, benzothiazolyl, and phenothiazinyl groups.

The mixed aliphatic-aromatic cyclic ring refers to a structure in which at least one aliphatic ring and at least one aromatic ring are linked and fused together and which is overall non-aromatic. The mixed aliphatic-aromatic polycyclic ring may contain one or more heteroatoms selected from N, O, P, and S other than carbon atoms (C).

The alkoxy group may be specifically a methoxy, ethoxy, propoxy, isobutyloxy, sec-butyloxy, pentyloxy, iso-amyloxy or hexyloxy group but is not limited thereto.

The silyl group is intended to include alkyl-substituted silyl groups and aryl-substituted silyl groups. Specific examples of such silyl groups include trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl.

The amine groups may be, for example, —$NH_2$, alkylamine groups, and arylamine groups. The arylamine groups are aryl-substituted amine groups and the alkylamine groups are alkyl-substituted amine groups. Examples of the arylamine groups include substituted or unsubstituted monoarylamine groups, substituted or unsubstituted diarylamine groups, and substituted or unsubstituted triarylamine groups. The aryl groups in the arylamine groups may be monocyclic or polycyclic ones. The arylamine groups may include two or more aryl groups. In this case, the aryl groups may be monocyclic aryl groups or polycyclic aryl groups. Alternatively, the aryl groups may consist of a monocyclic aryl group and a polycyclic aryl group. The aryl groups in the arylamine groups may be selected from those exemplified above.

The aryl groups in the aryloxy group and the arylthioxy group are the same as those described above. Specific examples of the aryloxy groups include, but are not limited to, phenoxy, p-tolyloxy, m-tolyloxy, 3,5-dimethylphenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, and 9-phenanthryloxy groups. The arylthioxy group may be, for example, a phenylthioxy, 2-methylphenylthioxy or 4-tert-butylphenylthioxy group but is not limited thereto.

The halogen group may be, for example, fluorine, chlorine, bromine or iodine.

According to one embodiment of the present invention, the compound represented by Formula A can be selected from the following compounds 1 to 104 but the scope of the present invention is not limited thereto:

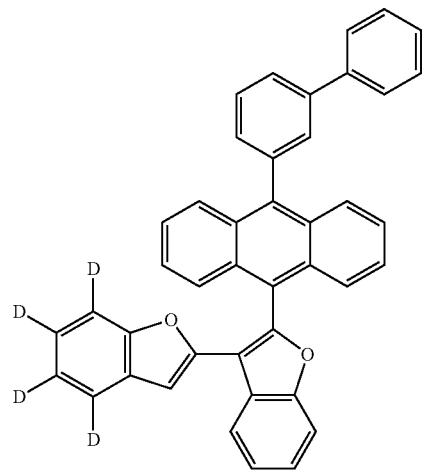

1

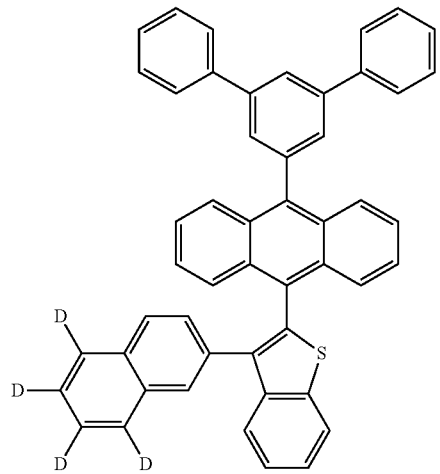

2

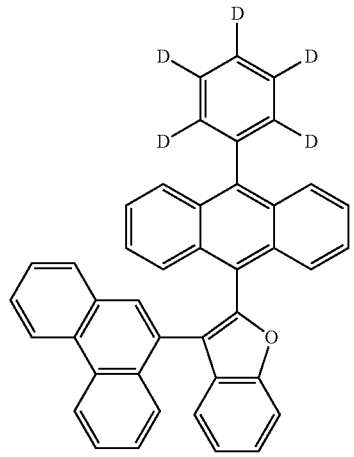

3

4
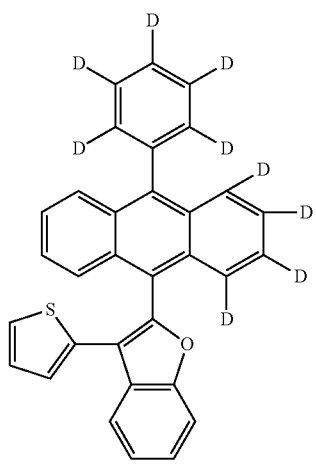
5
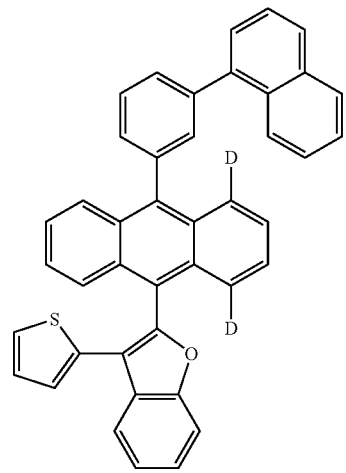
6
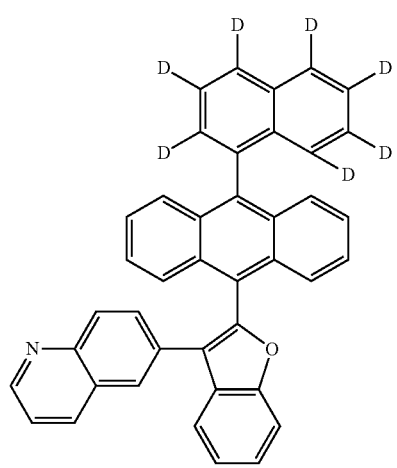
7
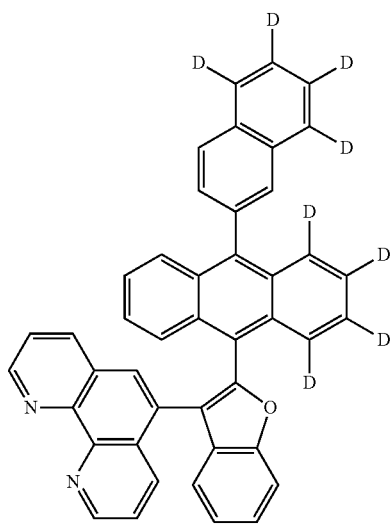
8
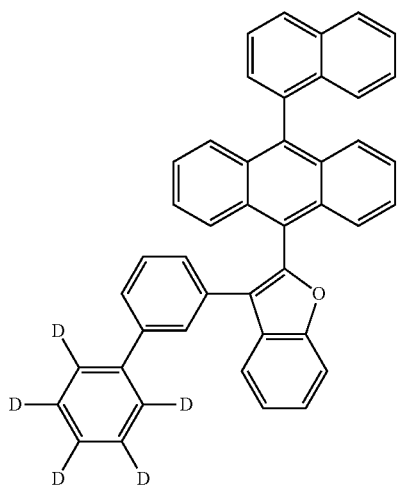
9
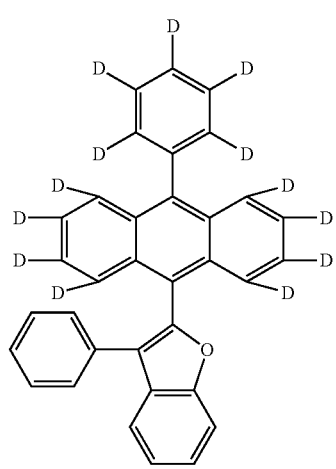

10
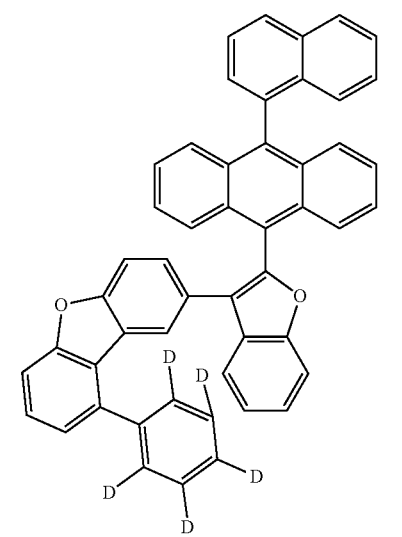
11
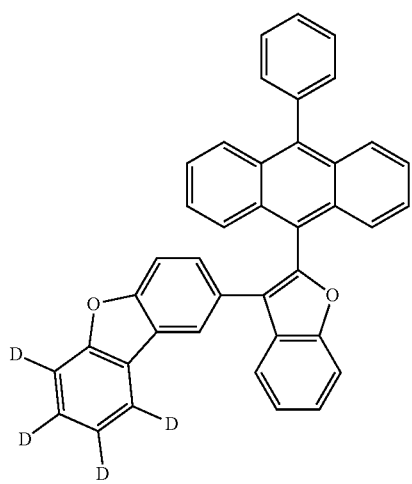
12
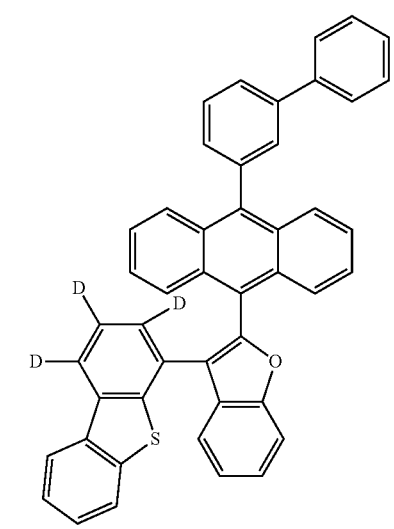
13
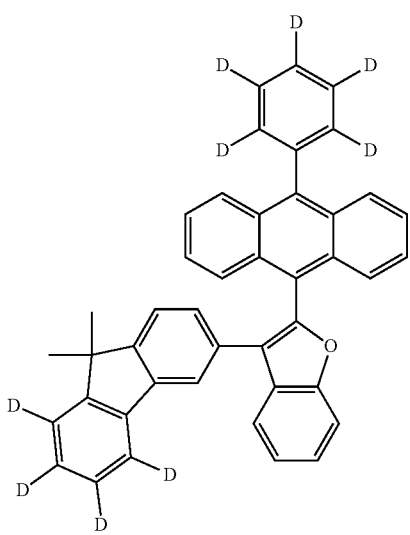
14
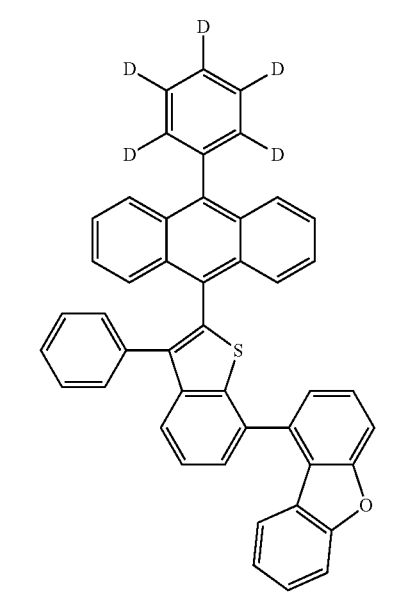
15
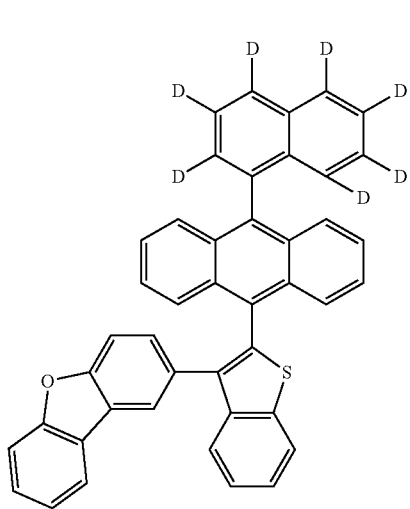

16
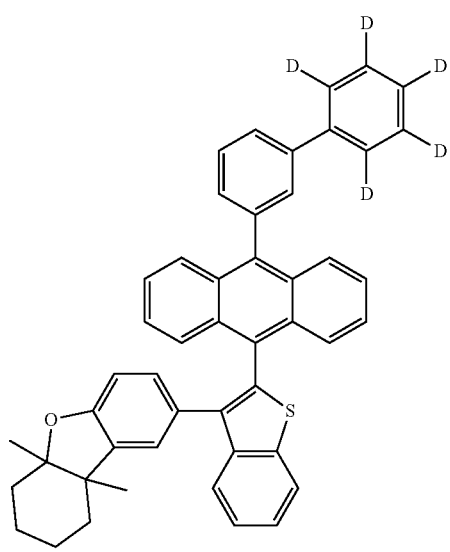
17
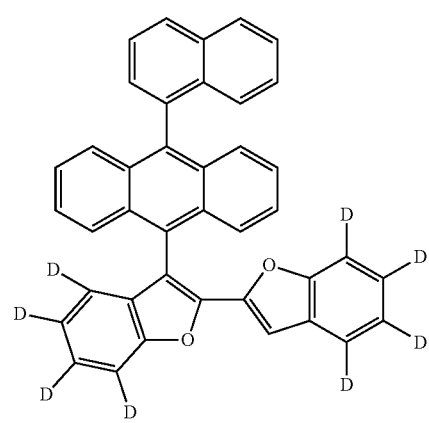
18
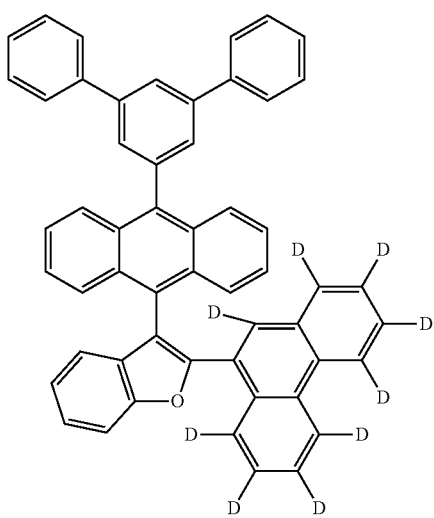
19
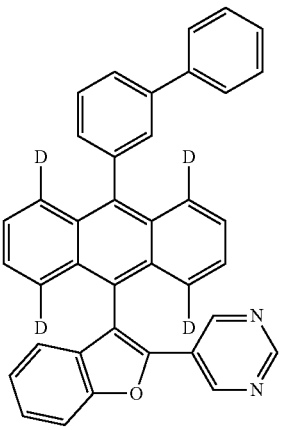
20
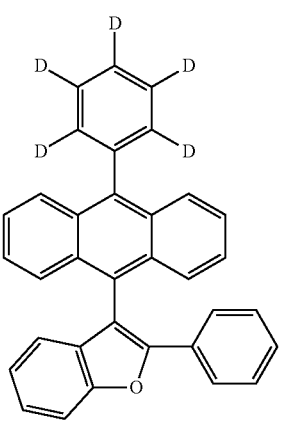
21
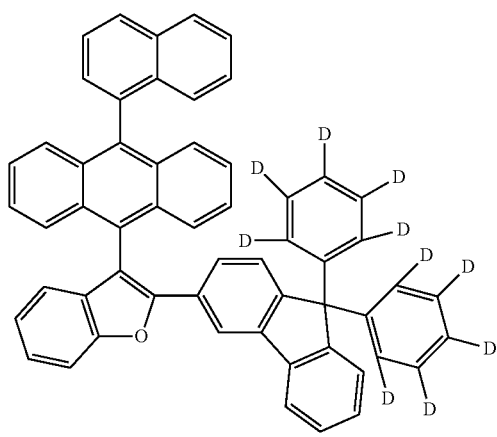

22
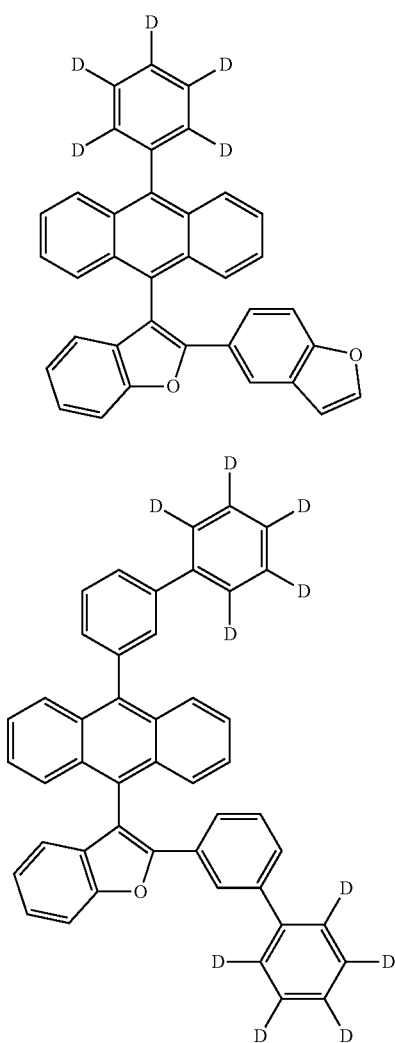
23
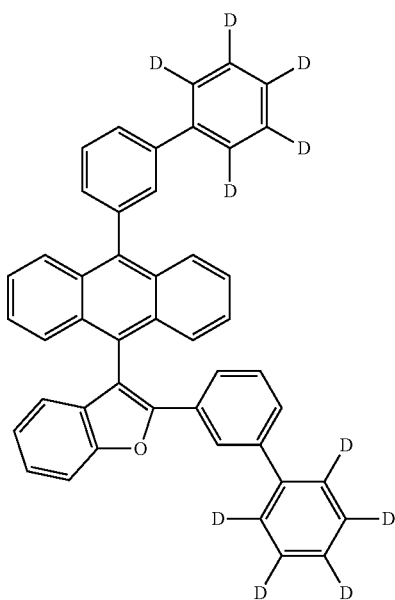
24
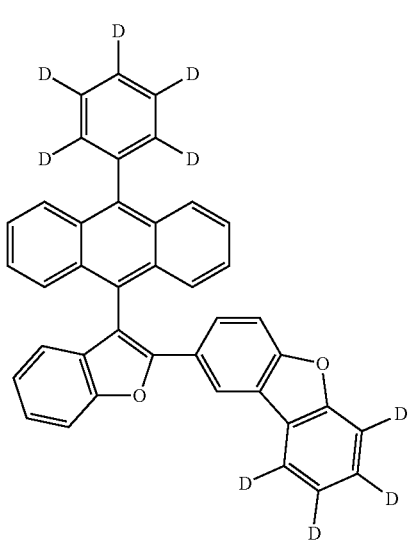
25
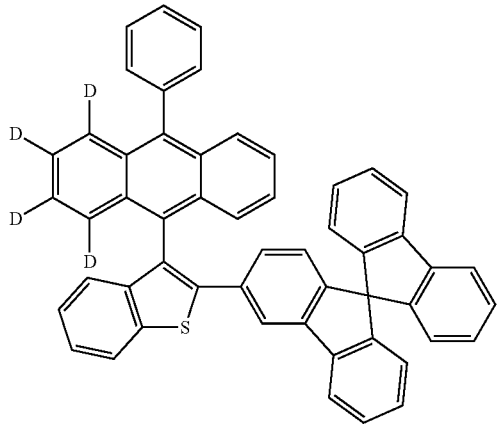
26
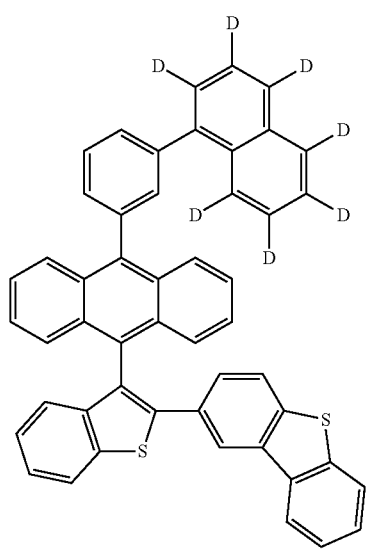
27
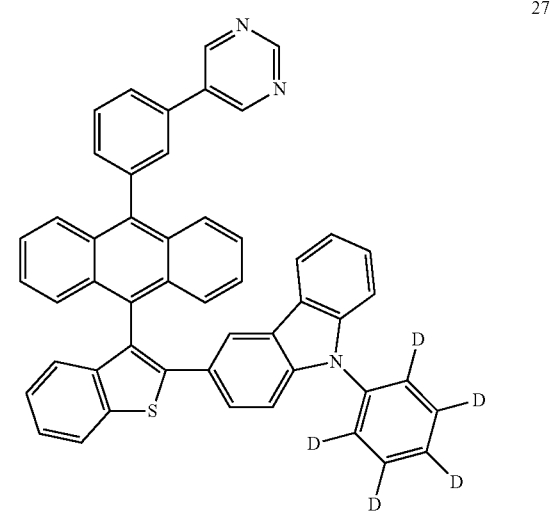

28
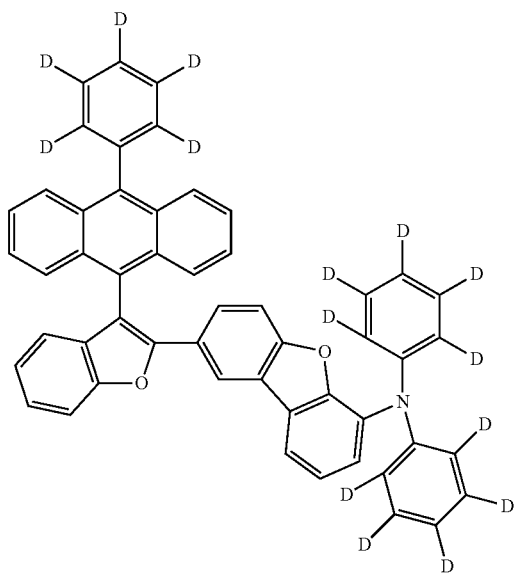
29
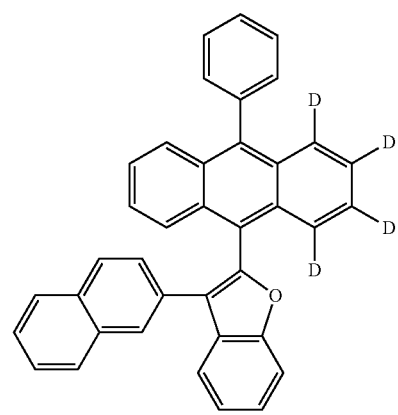
30
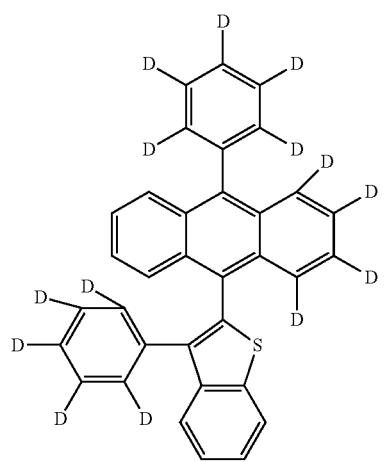
31
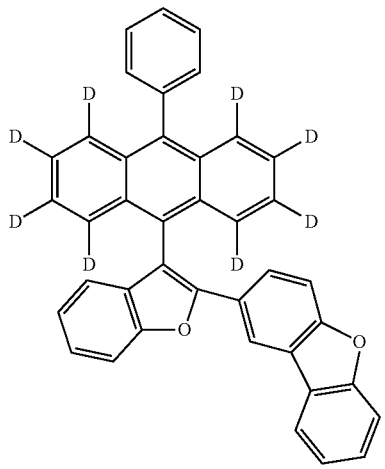
32
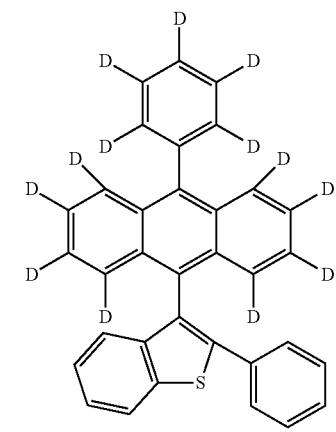
33
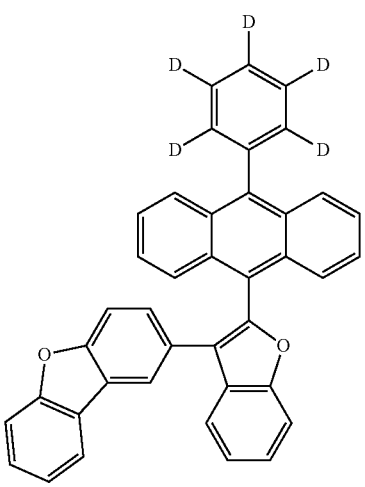

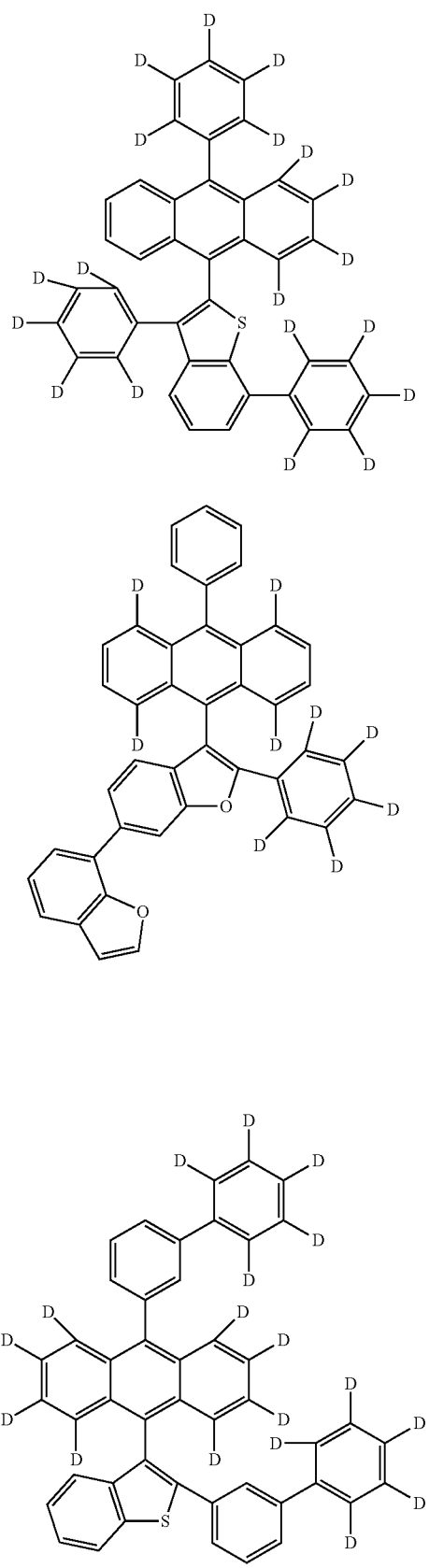
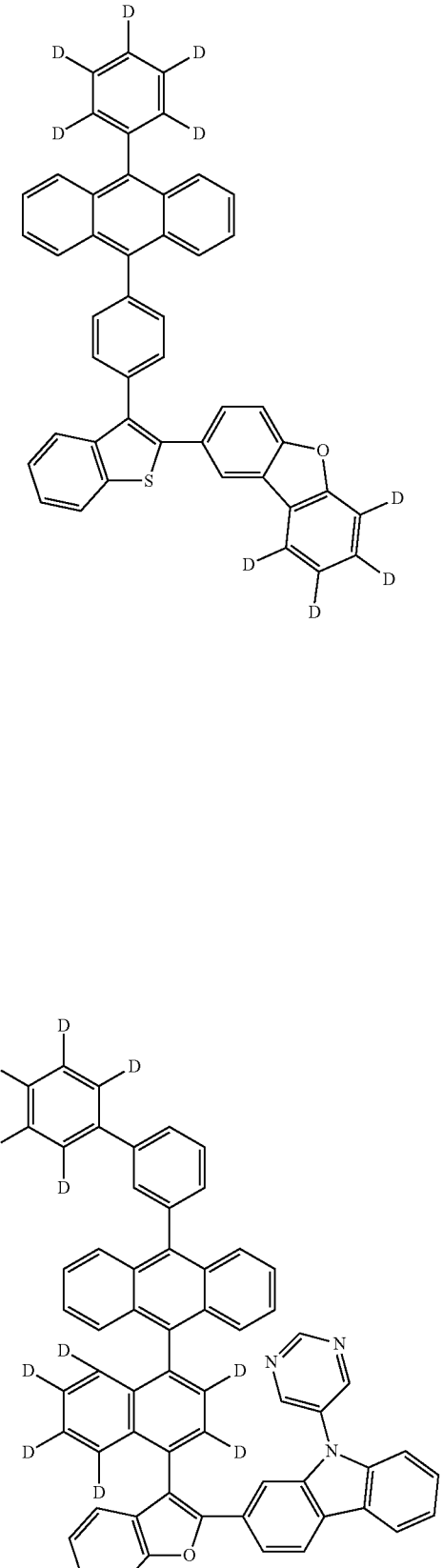

39
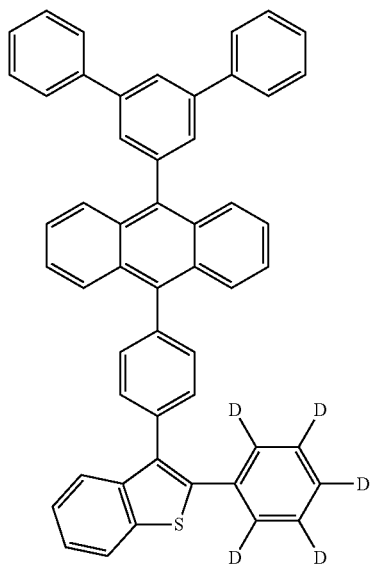
40
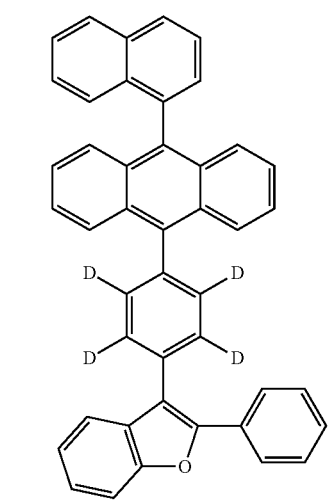
41
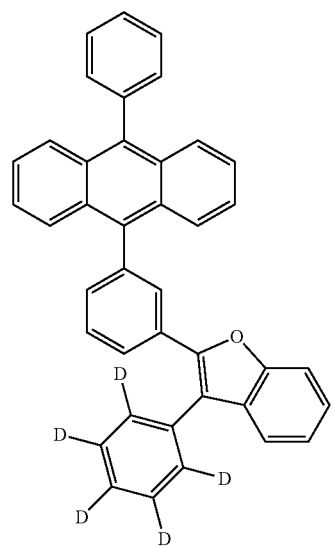
42
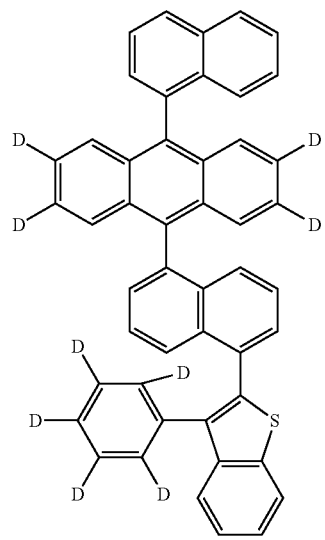
43
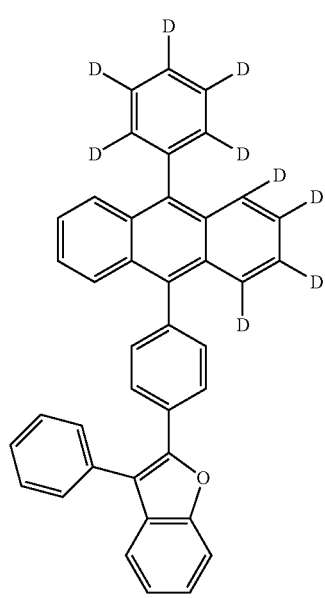

44
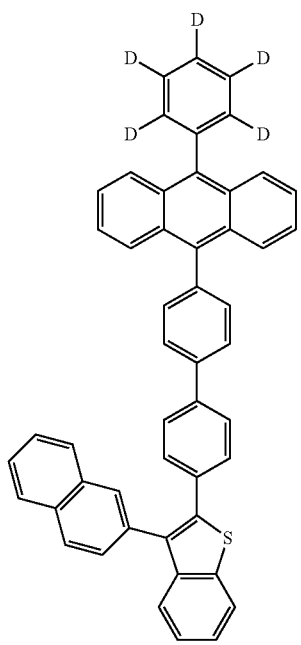
46
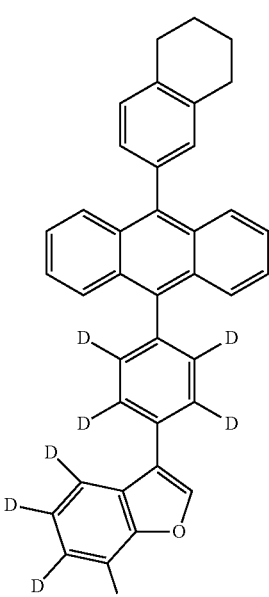
45
47
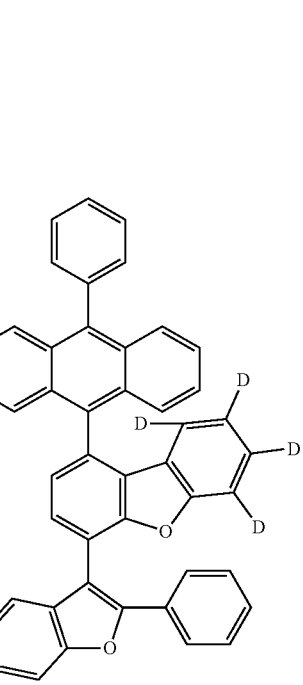

48
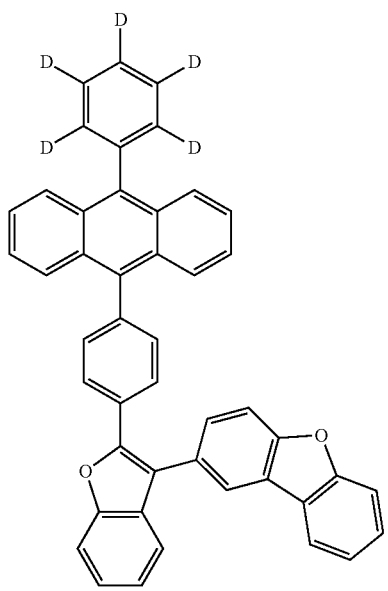
50
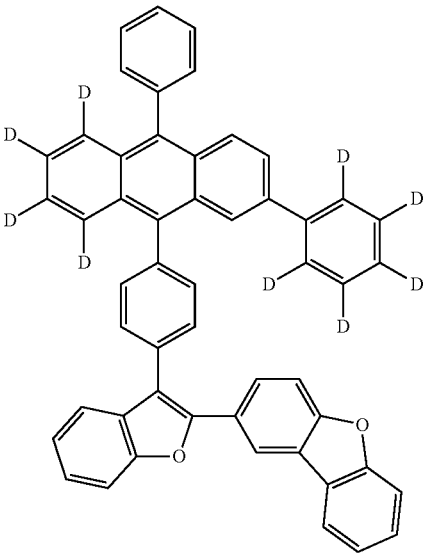
49
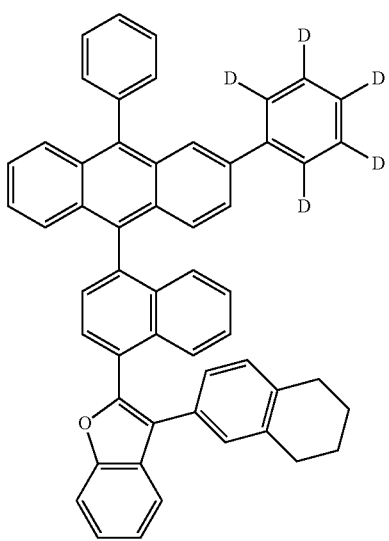
51
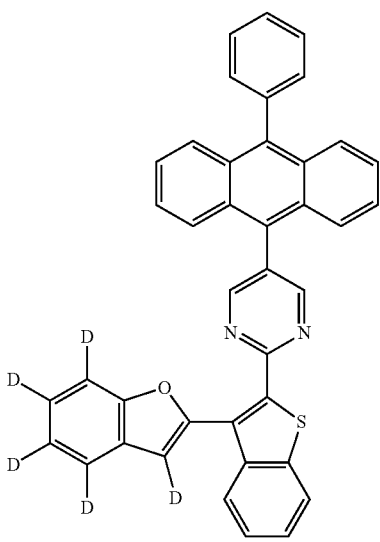

52
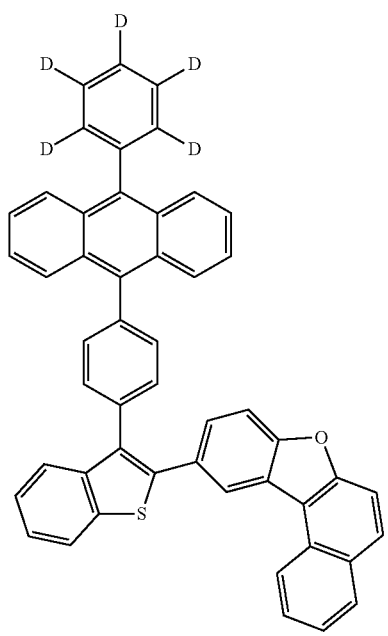
53
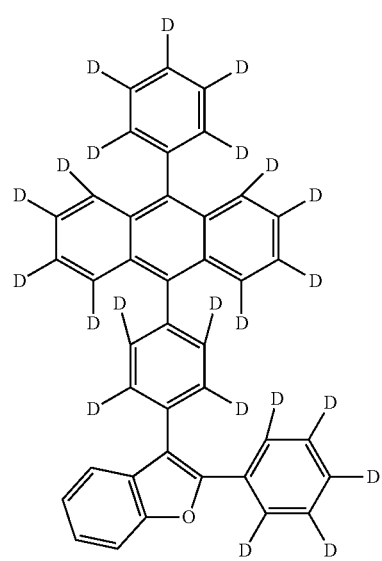
54
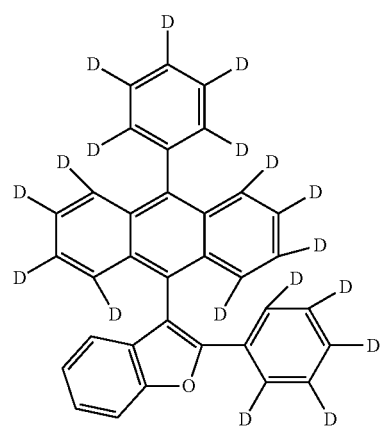
55
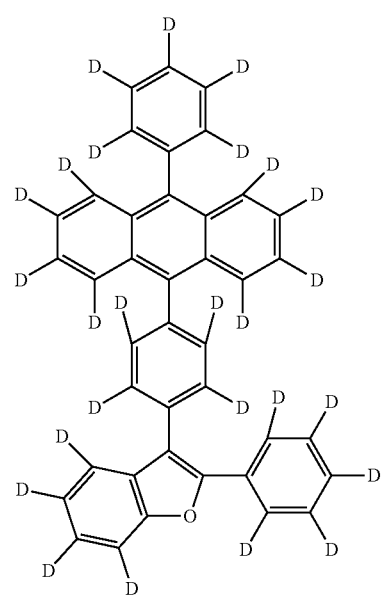
56
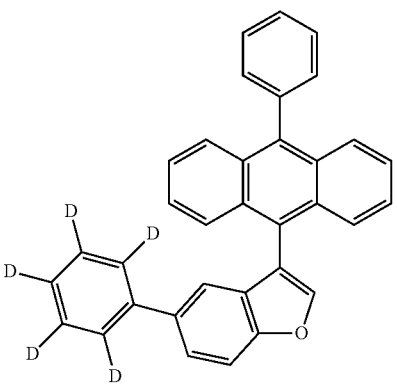
57
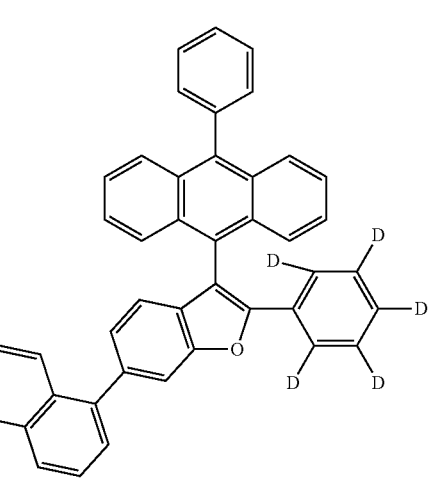

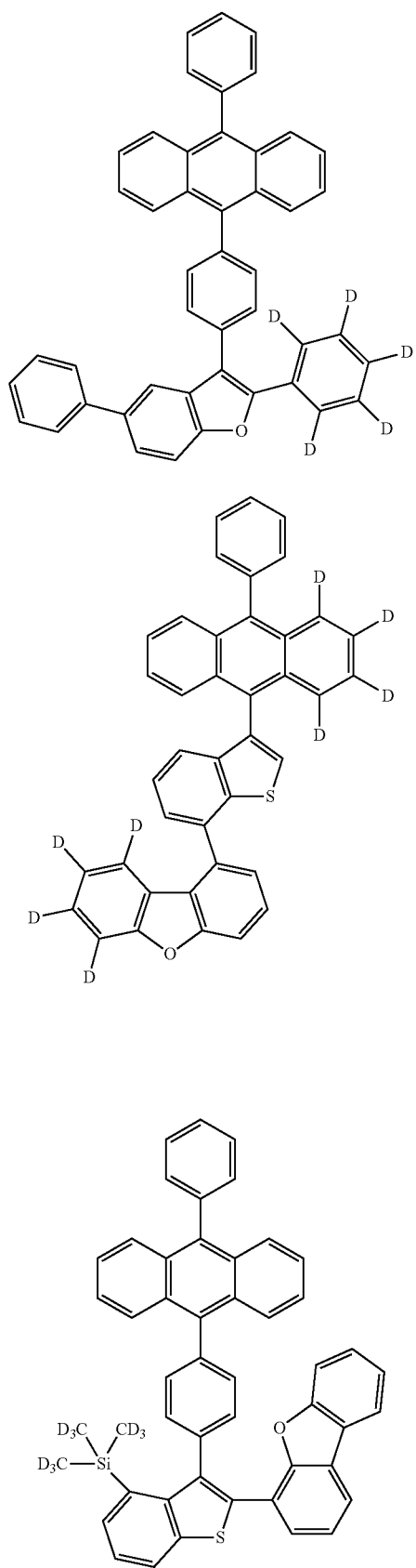
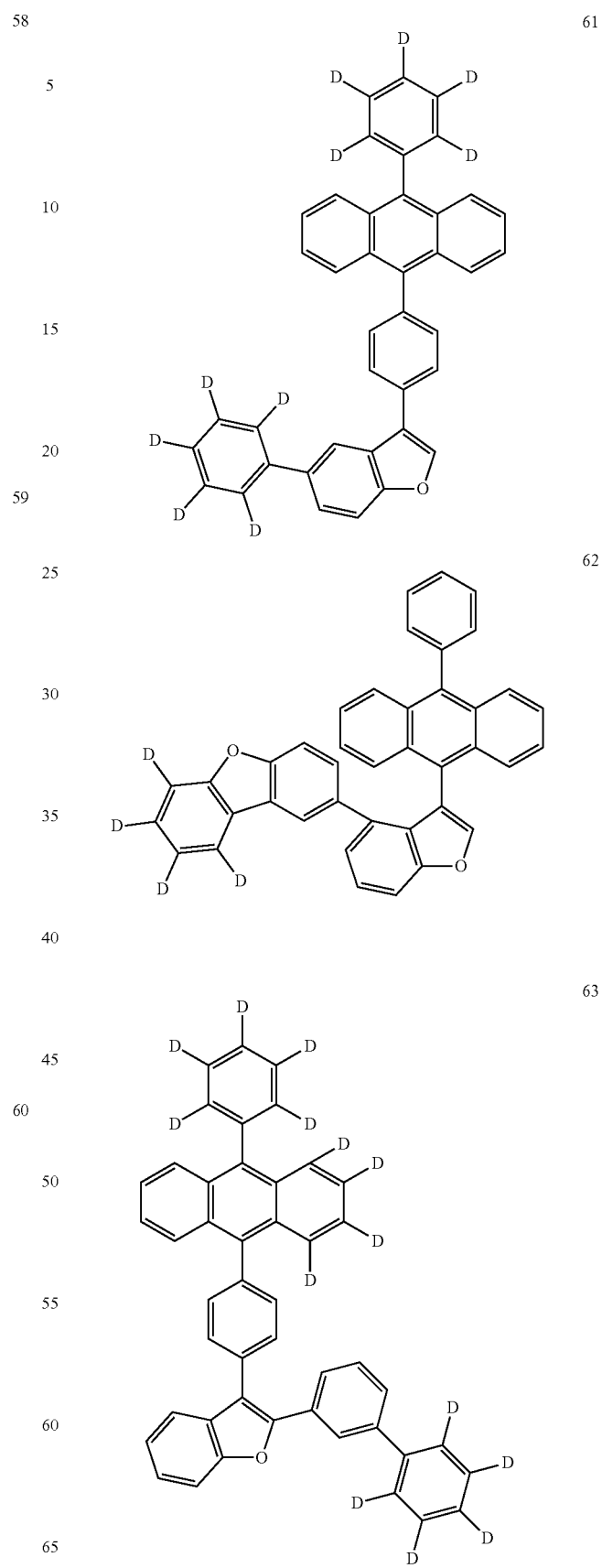

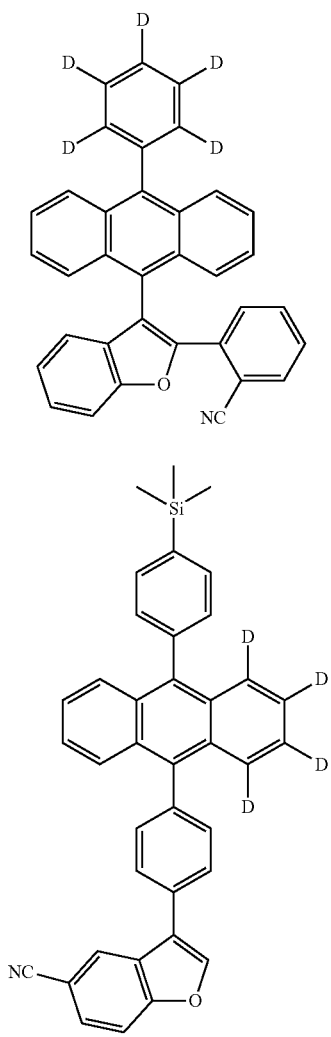
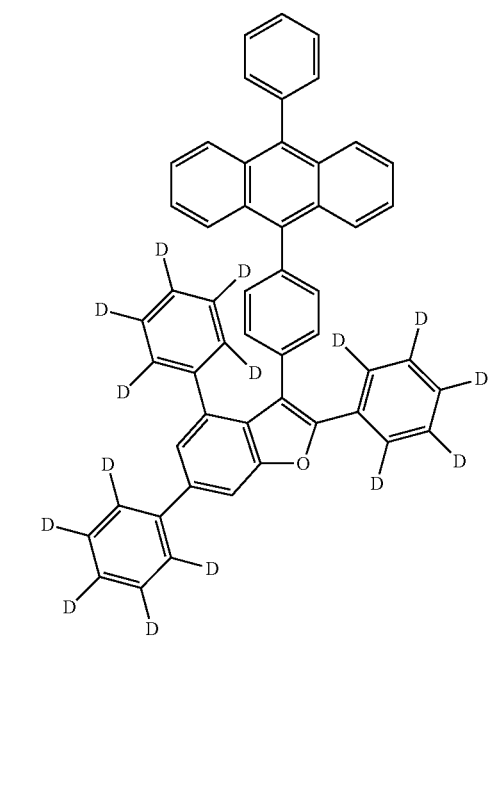
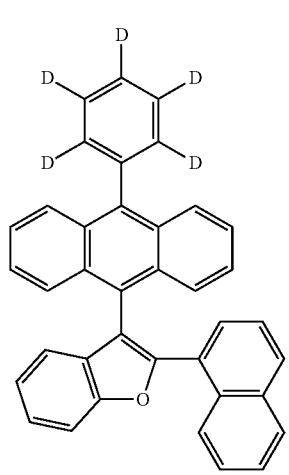
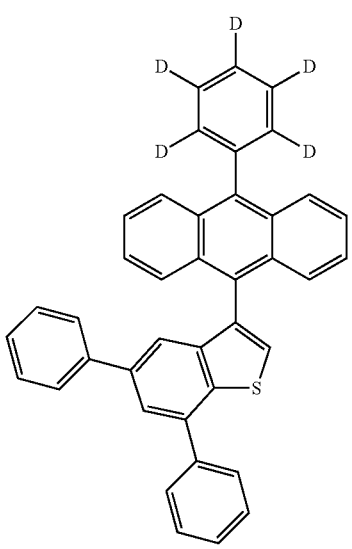

69
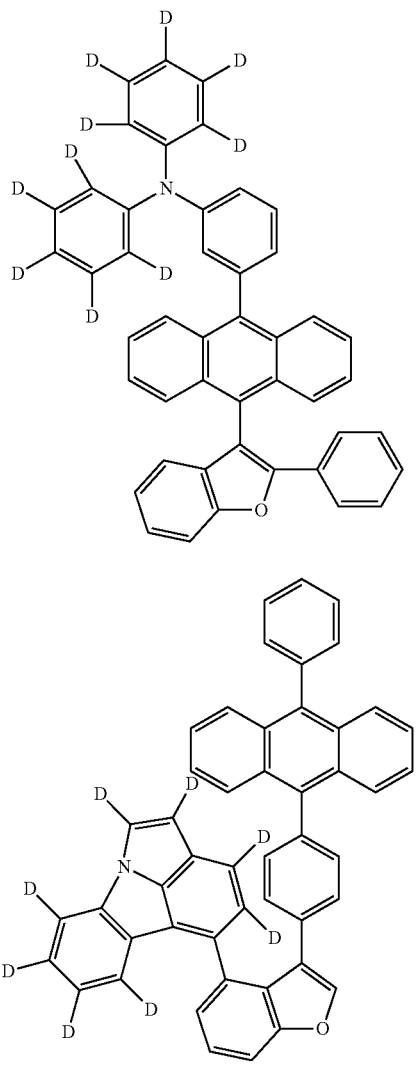
70
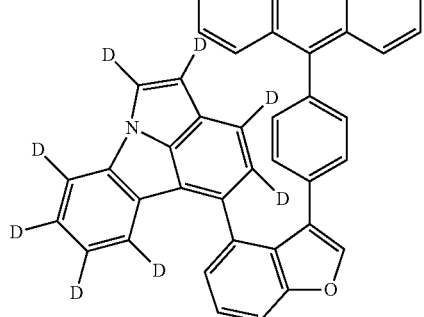
71
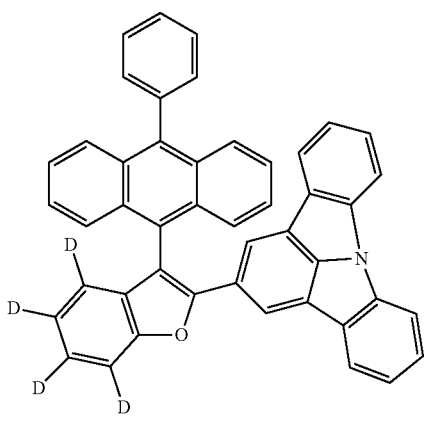
72
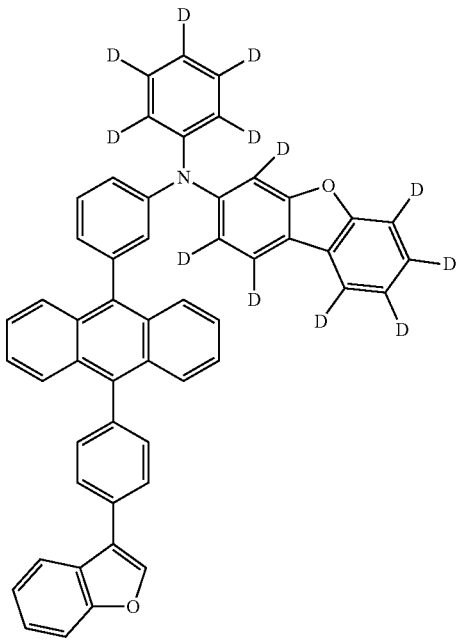
73
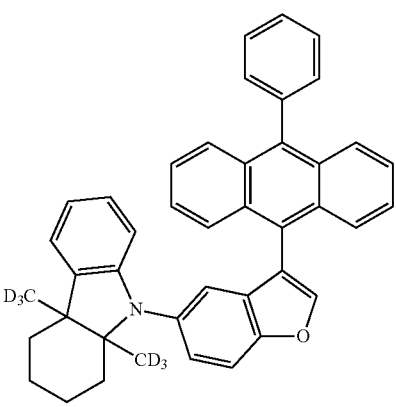

74
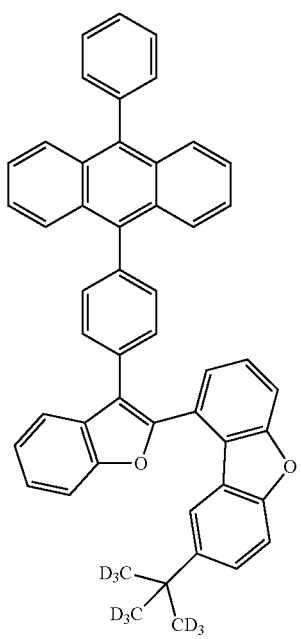
75
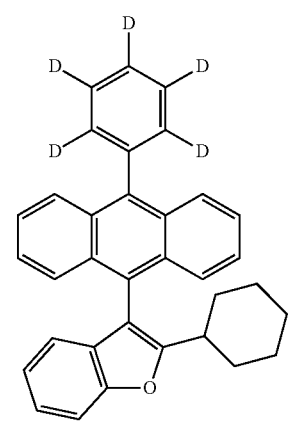
76
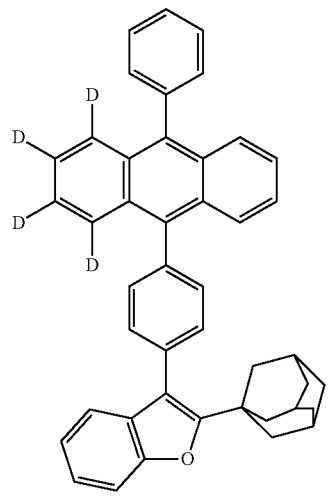
77
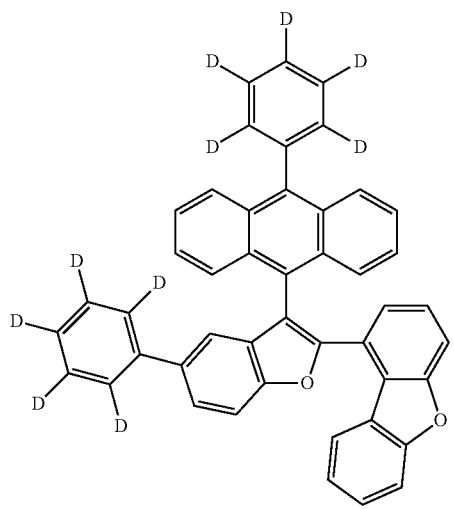
78
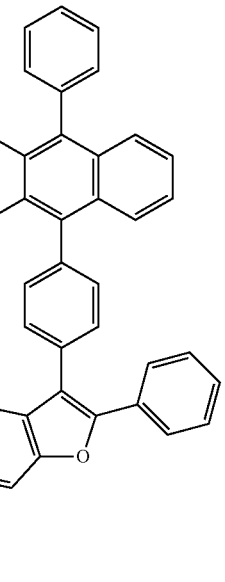
79
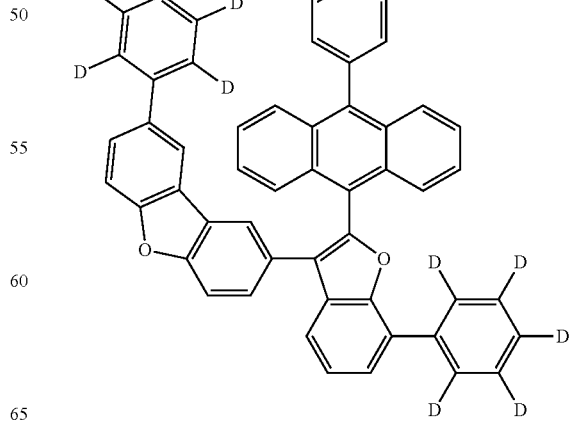

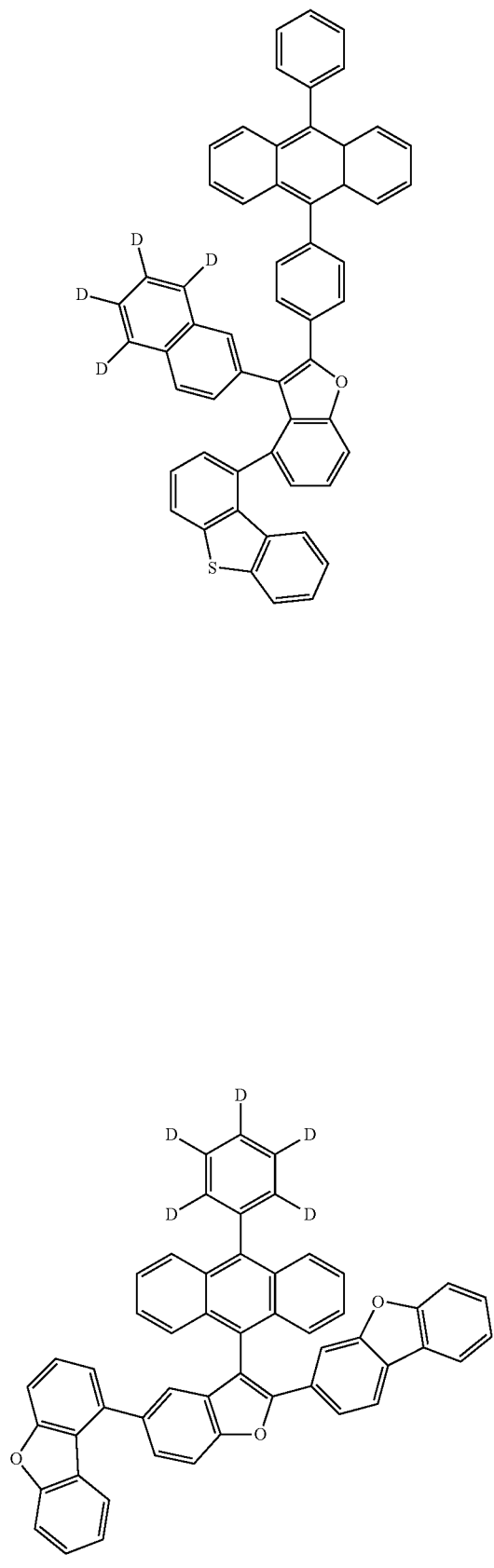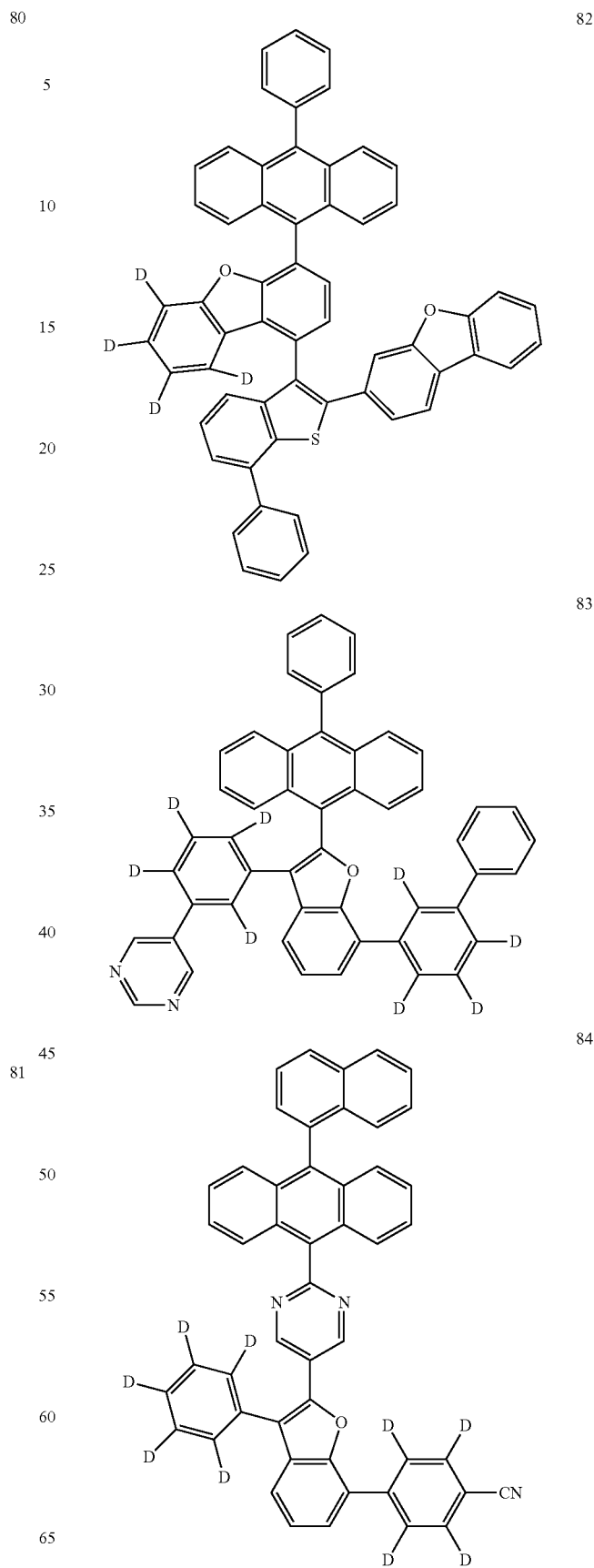

85
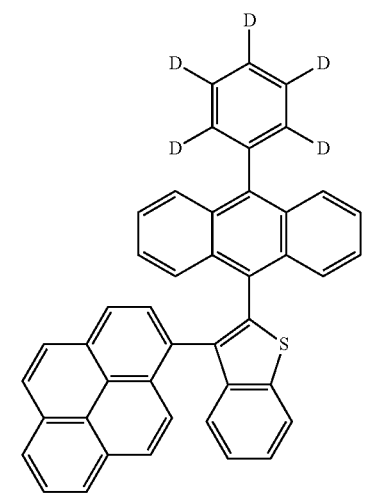
86
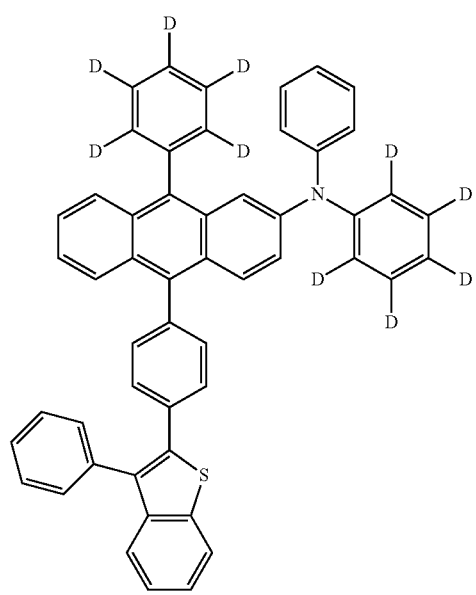
87
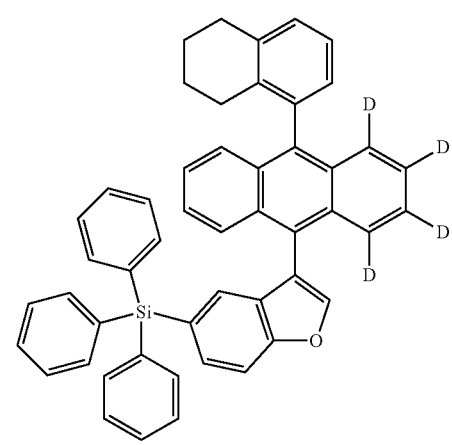
88
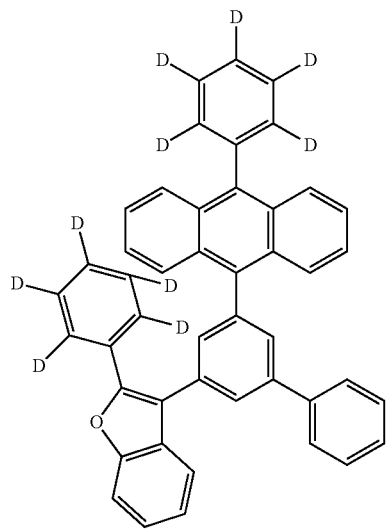
89
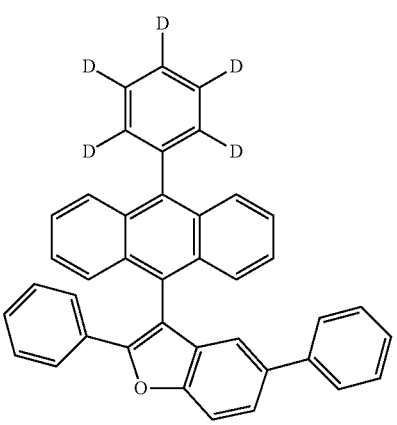
90
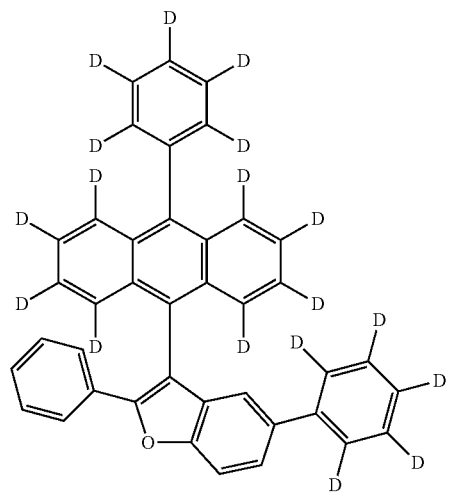

91
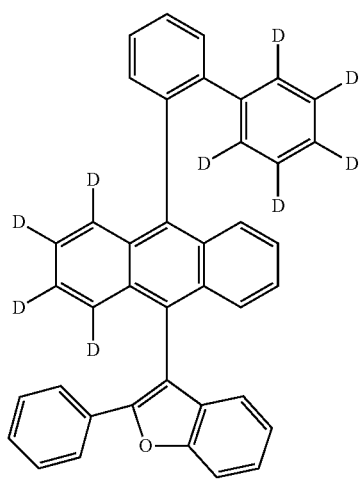
92
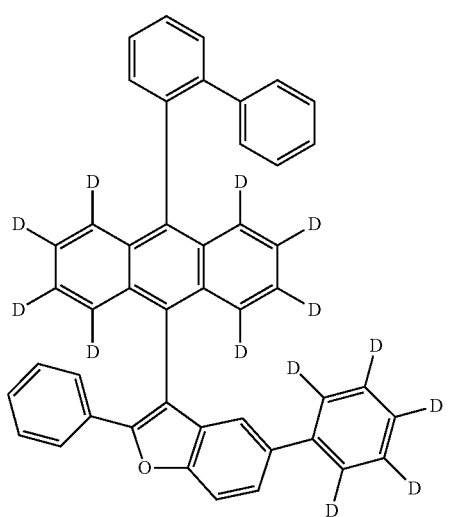
93
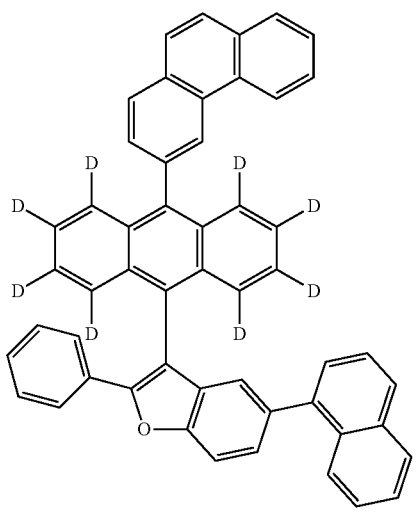
94
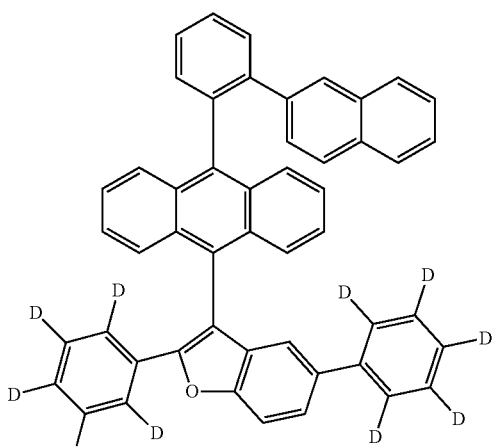
95
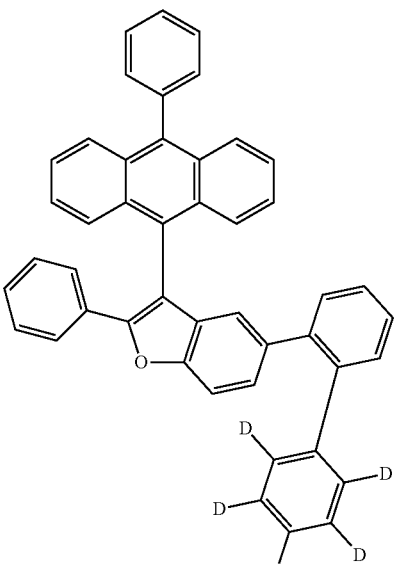

96
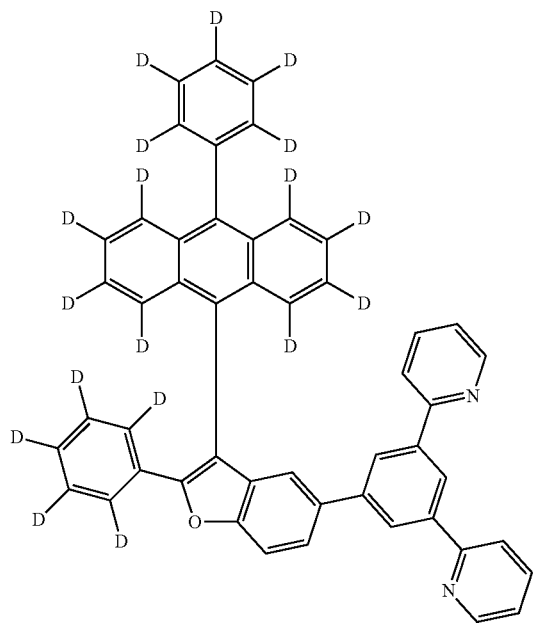
97
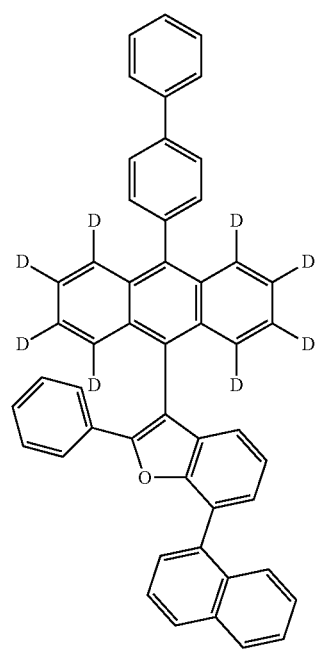
98
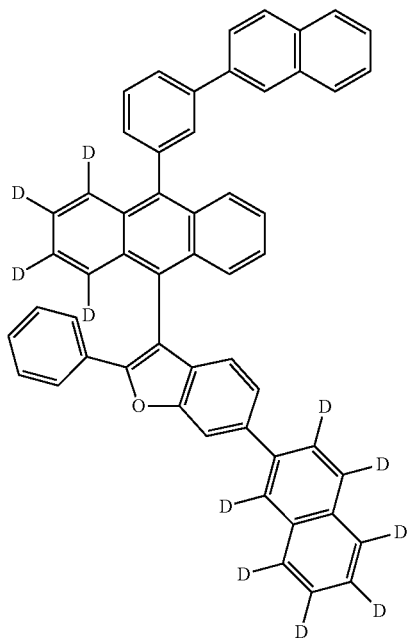
99
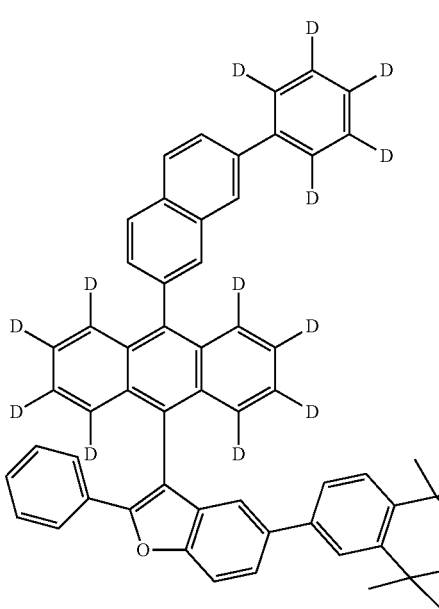

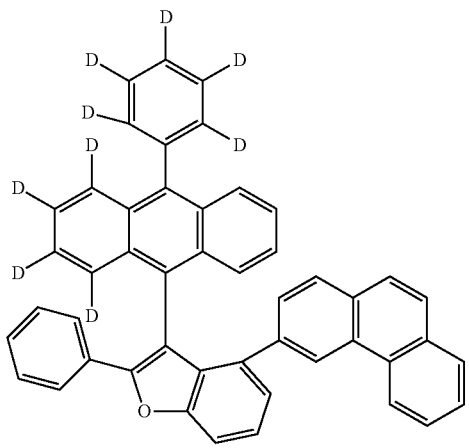

100

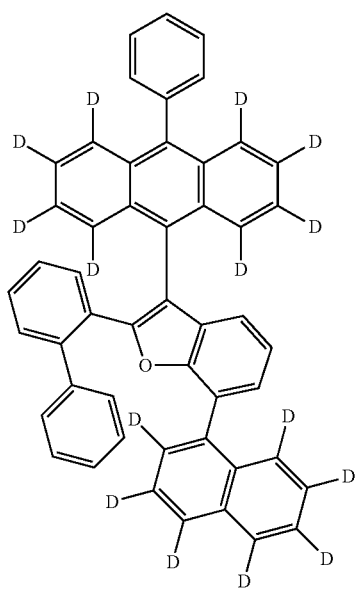

101

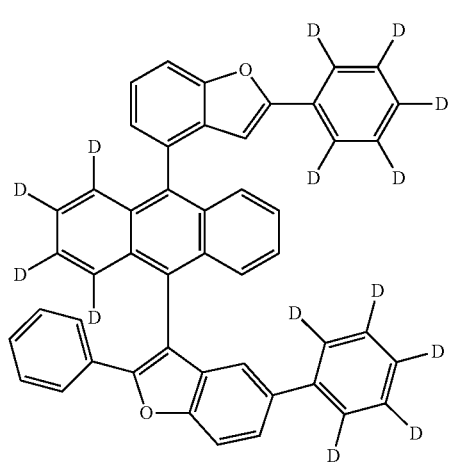

102

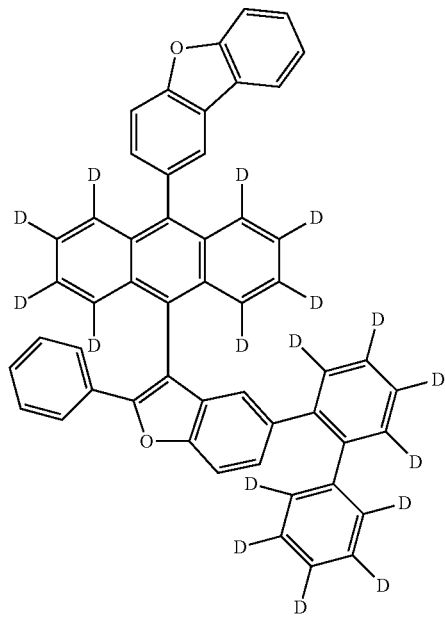

103

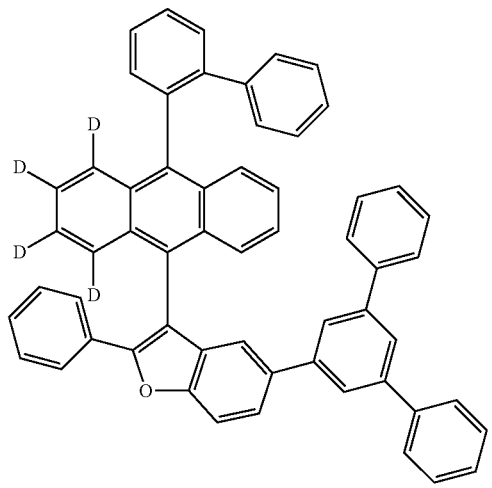

104

Another aspect of the present invention is directed to an organic electroluminescent device including a first electrode, a second electrode opposite to the first electrode, and one or more organic layers interposed between the first and second electrodes wherein one of the organic layers, preferably a light emitting layer includes the anthracene derivative represented by Formula A.

The light emitting layer is composed of a host and a dopant. The anthracene derivative represented by Formula A is used as the host. One or more host compounds other than the host compound represented by Formula A may be mixed or stacked in the light emitting layer.

According to one embodiment of the present invention, the organic electroluminescent device may further include a dopant compound in the light emitting layer.

As used herein, the expression "(an organic layer) includes one or more organic compounds" means that (the organic layer) includes one of the organic compounds belonging to the scope of the present invention or two or more different compounds belonging to the scope of the organic compounds.

The organic layers may include a hole injecting layer, a hole transport layer, a functional layer having functions of both hole injection and hole transport, a light emitting layer, an electron transport layer, and/or an electron injecting layer.

According to a more preferred embodiment of the present invention, one of the organic layers interposed between the first and second electrodes may be a light emitting layer. The light emitting layer may be composed of a host and a dopant. The light emitting layer may include, as a host, at least one of the anthracene derivatives that can be represented by Formula A.

The dopant compound used in the light emitting layer is represented by Formula D-1:

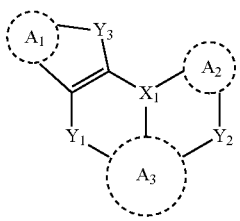

(D-1)

wherein $X_1$ is selected from B, P=O, and P=S, $Y_1$ to $Y_3$ are each independently selected from $NR_{41}$, $CR_{42}R_{43}$, O, S, Se, and $SiR_{44}R_{45}$, $R_{41}$ to $R_{45}$ are identical to or different from each other and are each independently selected from hydrogen, deuterium, substituted or unsubstituted $C_1$-$C_{30}$ alkyl, substituted or unsubstituted $C_6$-$C_{50}$ aryl, substituted or unsubstituted $C_3$-$C_{30}$ cycloalkyl, substituted or unsubstituted $C_3$-$C_{30}$ heterocycloalkyl, substituted or unsubstituted $C_2$-$C_{50}$ heteroaryl, substituted or unsubstituted $C_1$-$C_{30}$ alkoxy, substituted or unsubstituted $C_6$-$C_{30}$ aryloxy, substituted or unsubstituted $C_1$-$C_{30}$ alkylthioxy, substituted or unsubstituted $C_6$-$C_{30}$ arylthioxy, substituted or unsubstituted $C_1$-$C_{30}$ alkylamine, substituted or unsubstituted $C_6$-$C_{30}$ arylamine, substituted or unsubstituted $C_2$-$C_{30}$ heteroarylamine, substituted or unsubstituted $C_1$-$C_{30}$ alkylsilyl, substituted or unsubstituted $C_6$-$C_{30}$ arylsilyl, substituted or unsubstituted $C_3$-$C_{20}$ mixed aliphatic-aromatic cyclic groups, nitro, cyano, and halogen, with the proviso that each of $R_{41}$ to $R_{45}$ is optionally bonded to one or more of the rings $A_1$ to $A_3$ to form an alicyclic or aromatic monocyclic or polycyclic ring and that $R_{42}$ and $R_{43}$ together and $R_{44}$ and $R_{45}$ together optionally form an alicyclic or aromatic monocyclic or polycyclic ring, and $A_1$ to $A_3$ are each independently selected from substituted or unsubstituted $C_6$-$C_{50}$ aromatic hydrocarbon rings, substituted or unsubstituted $C_2$-$C_{50}$ heteroaromatic rings, substituted or unsubstituted $C_3$-$C_{30}$ aliphatic rings, and unsubstituted or unsubstituted $C_3$-$C_{30}$ mixed aliphatic-aromatic cyclic groups, with the proviso that the substituents of each of the rings $A_1$ to $A_3$ together optionally form an alicyclic or aromatic monocyclic or polycyclic ring, or Formula D-2:

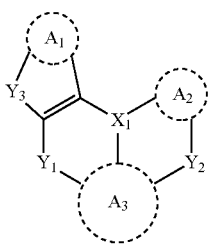

(D-2)

wherein $X_1$, $Y_1$ to $Y_3$, $R_{41}$ to $R_{45}$, and $A_1$ to $A_3$ are as defined in Formula D-1.

As used herein, the term "substituted" in the definition of $A_1$ to A3 and $R_{41}$ to $R_{45}$ indicates substitution with one or more substituents selected from deuterium, cyano, halogen, hydroxyl, nitro, $C_1$-$C_{24}$ alkyl, $C_1$-$C_{24}$ haloalkyl, $C_3$-$C_{30}$ cycloalkyl, $C_2$-$C_{24}$ alkenyl, $C_2$-$C_{24}$ alkynyl, $C_1$-$C_{24}$ heteroalkyl, $C_6$-$C_{30}$ aryl, $C_7$-$C_{30}$ arylalkyl, $C_7$-$C_{30}$ alkylaryl, $C_2$-$C_{30}$ heteroaryl, $C_2$-$C_{30}$ heteroarylalkyl, $C_1$-$C_{24}$ alkoxy, $C_1$-$C_{24}$ alkylamino, $C_6$-$C_{30}$ arylamino, $C_2$-$C_{30}$ heteroarylamino, $C_1$-$C_{24}$ alkylsilyl, $C_6$-$C_{30}$ arylsilyl, $C_6$-$C_{30}$ aryloxy, and $C_3$-$C_{30}$ mixed aliphatic-aromatic cyclic groups. The term "unsubstituted" in the same definition indicates having no substituent.

According to one embodiment of the present invention, the dopant compounds represented by Formulae D-1 and D-2 can be selected from the following compounds 101 to 210 but the scope of the present invention is not limited thereto:

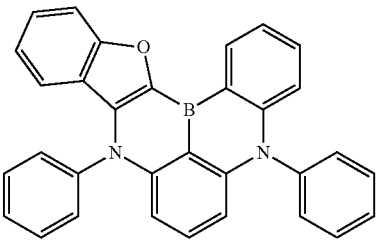

D-101

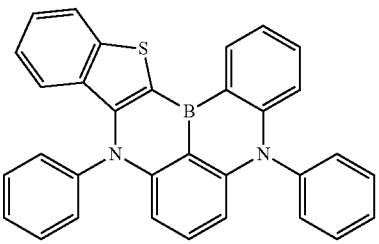

D-102

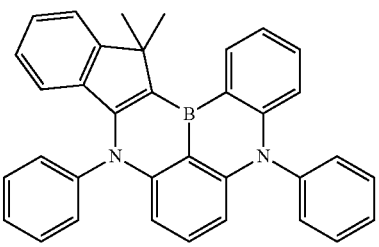

D-103

-continued
D-104
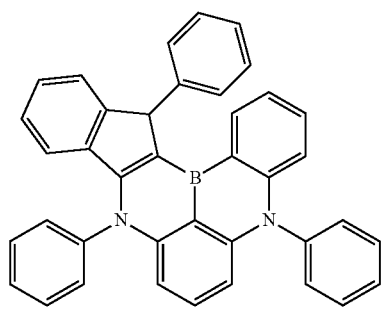
D-105
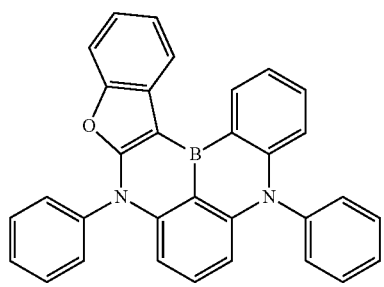
D-106
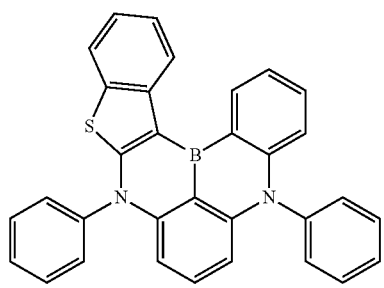
D-107
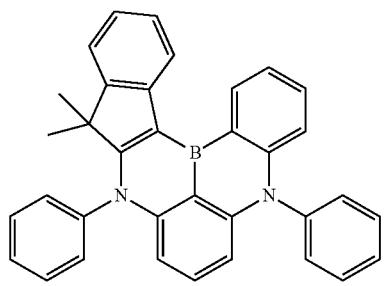
D-108
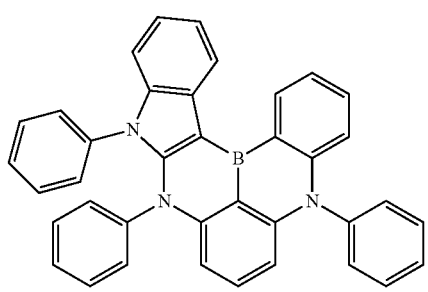
-continued
D-109
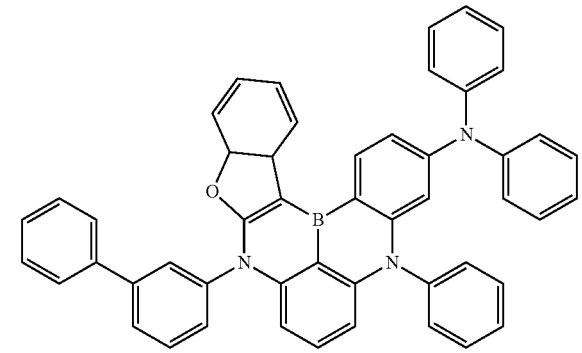
D-110
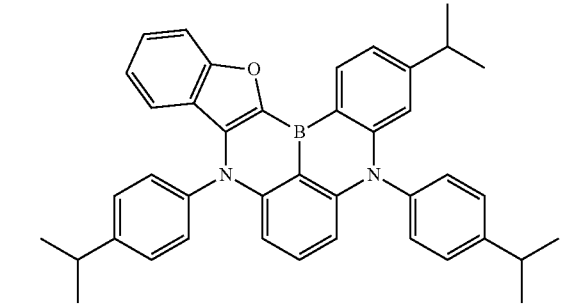
D-111
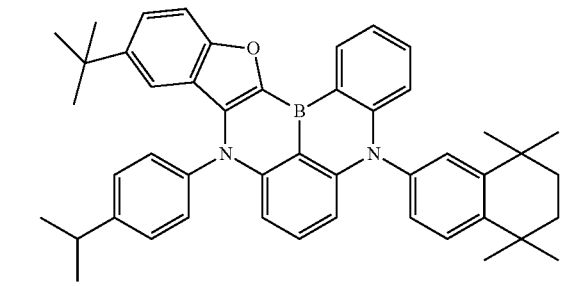
D-112
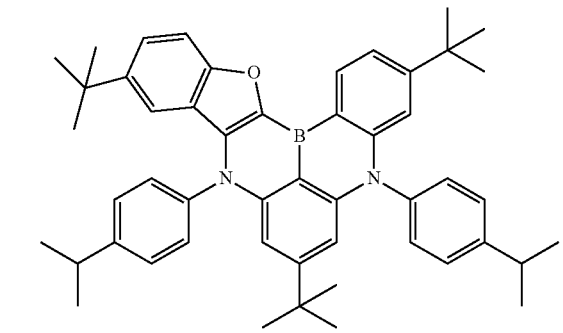

-continued
D-113
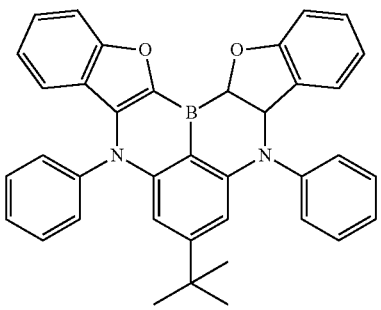
D-114
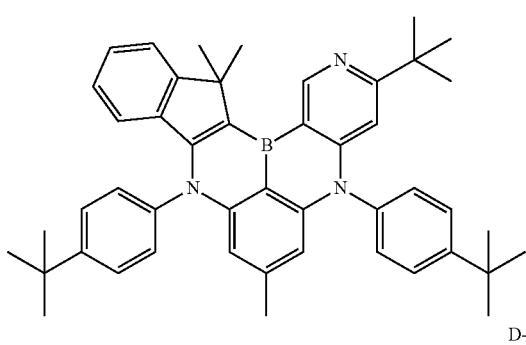
D-115
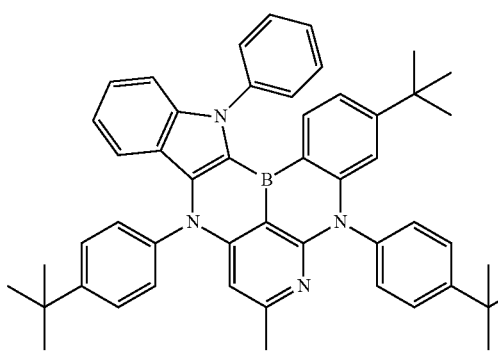
D-116
D-117
-continued
D-118
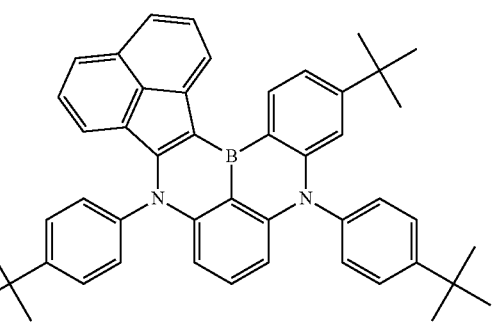
D-119
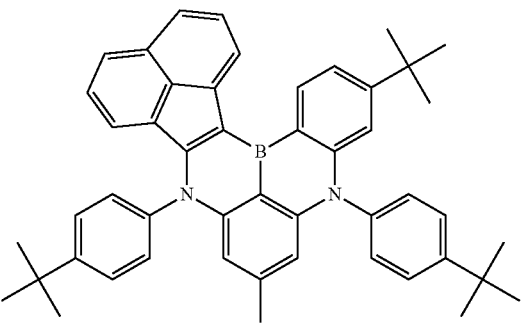
D-120
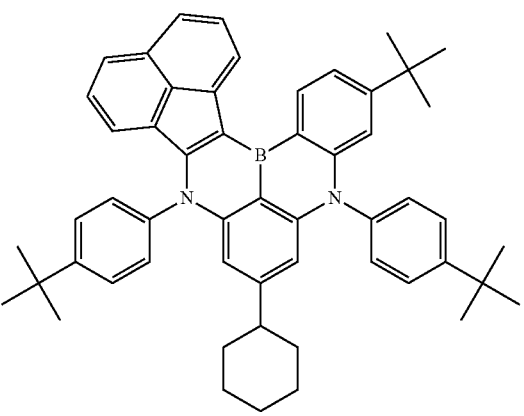
D-121
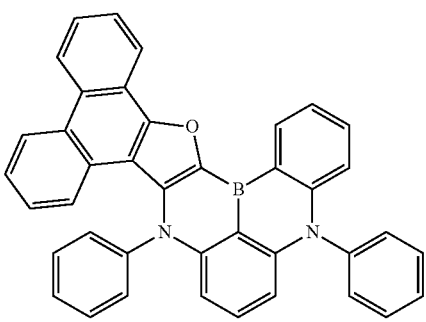

D-122
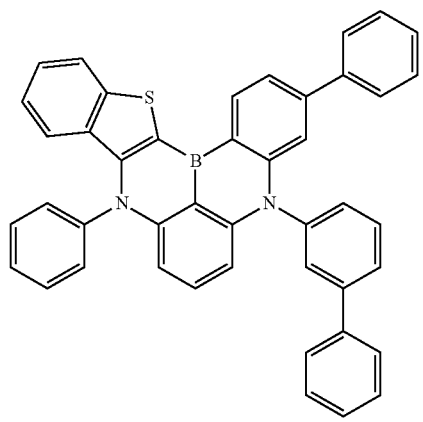
D-123
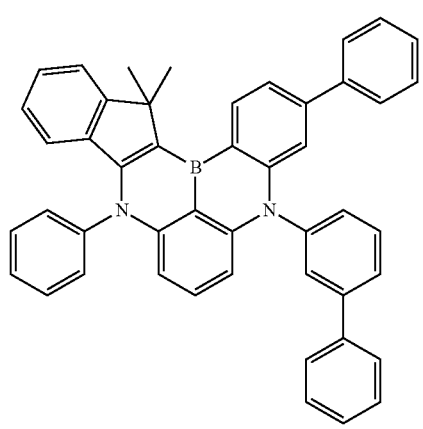
D-124
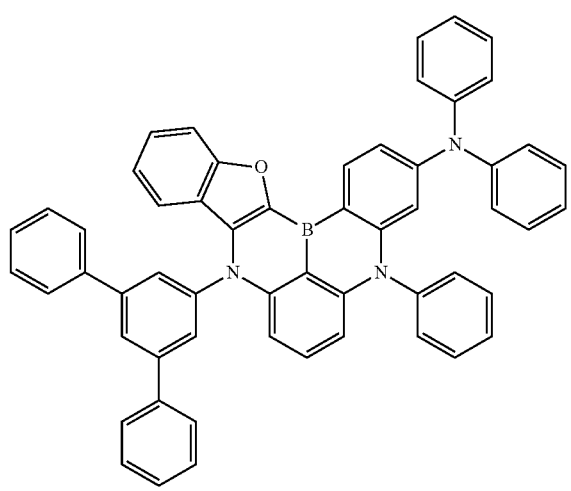
D-125
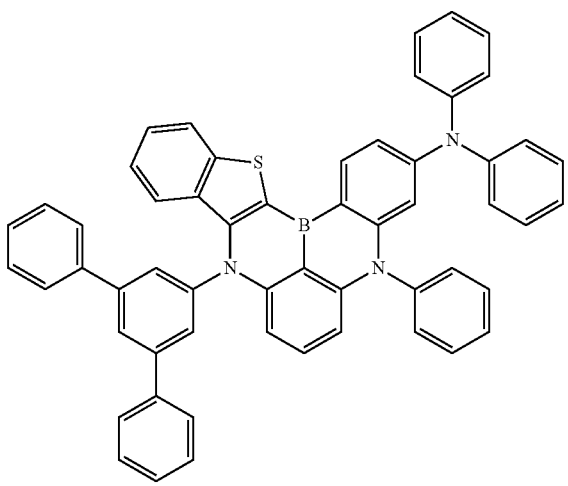
D-126
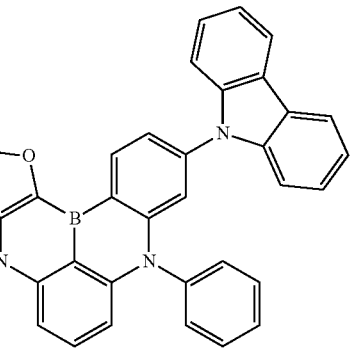
D-127

D-128
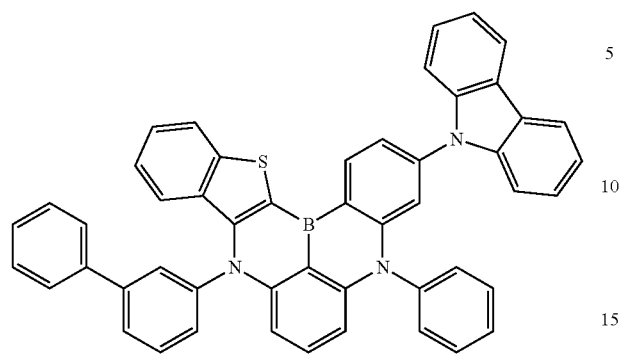
D-129
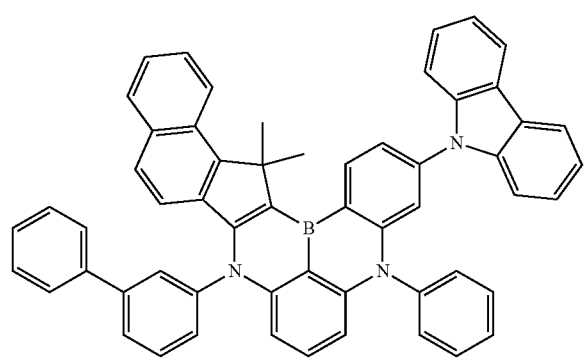
D-130
D-131
D-132
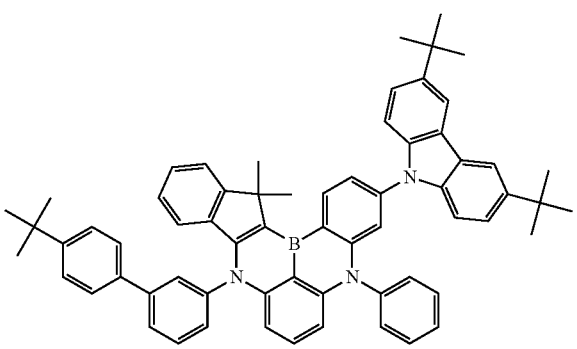
D-133
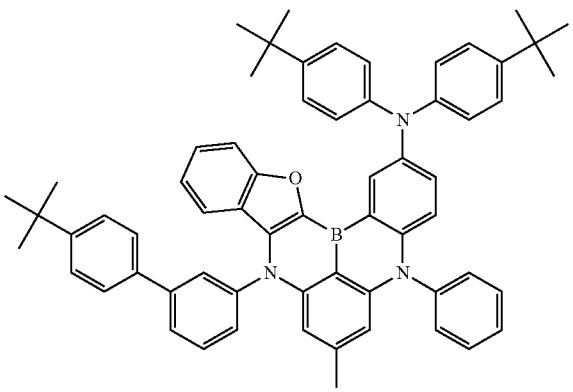
D-134
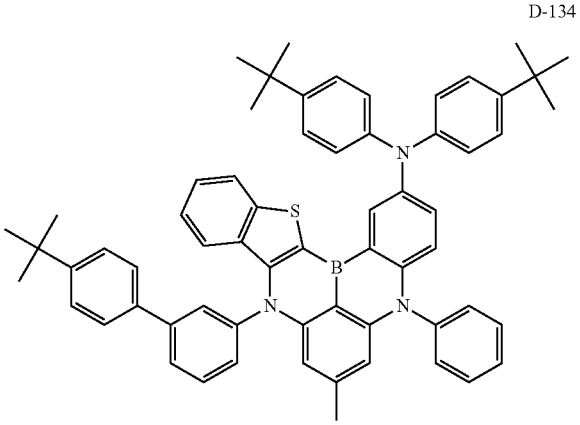
D-135
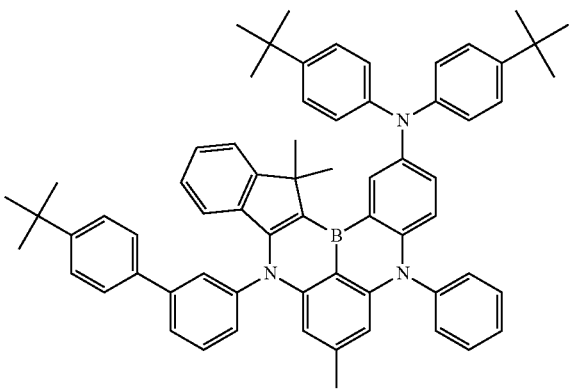

-continued
D-136
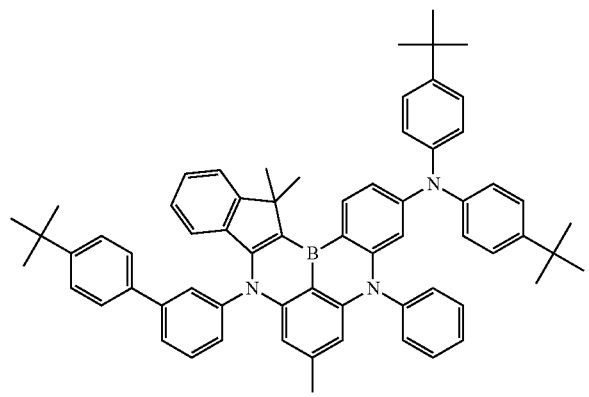
D-137
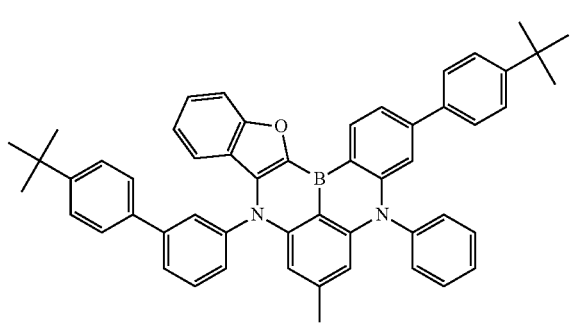
D-138
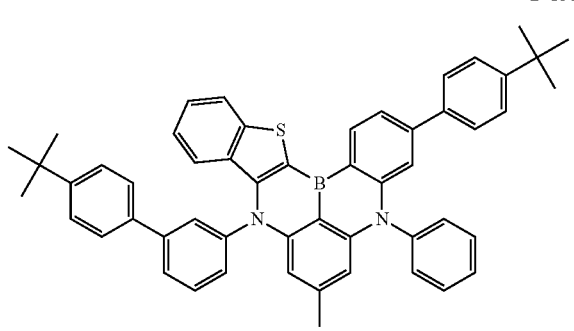
D-139
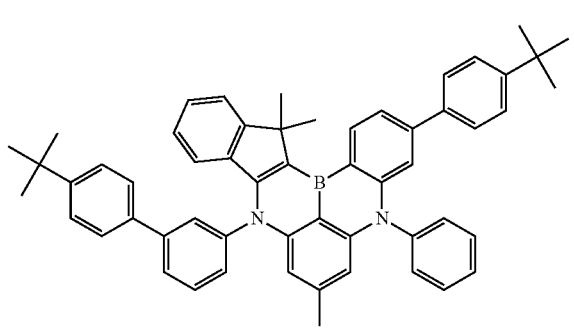
D-140
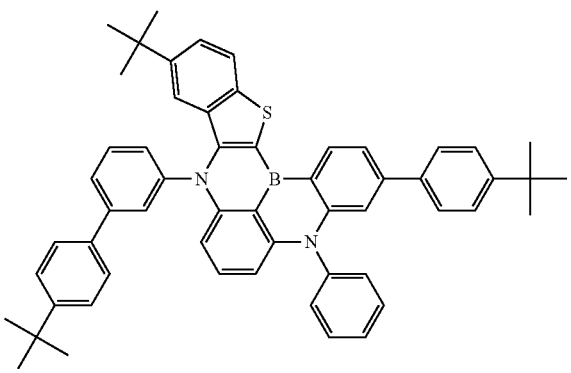
D-141
D-142
D-143
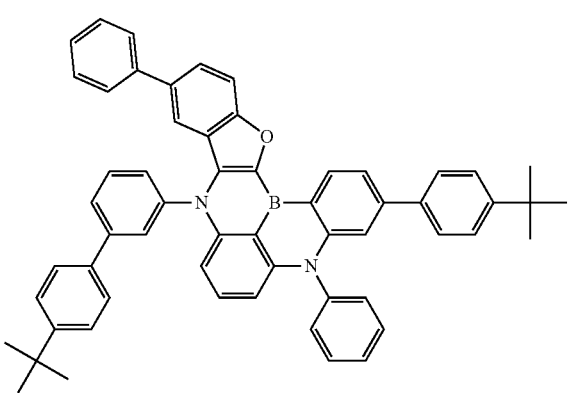

D-144
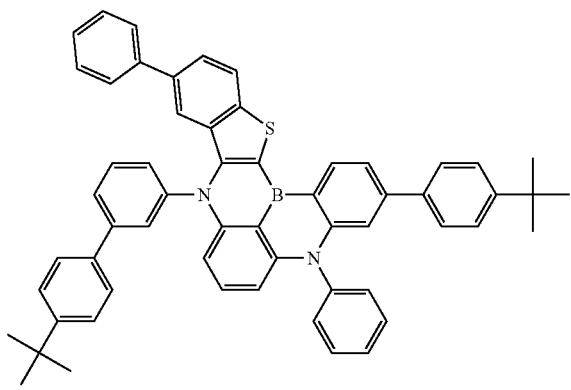
D-145
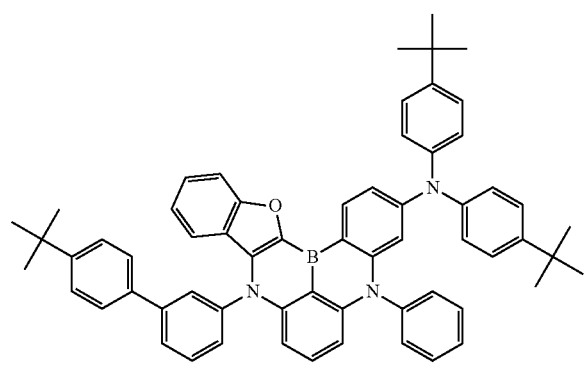
D-146
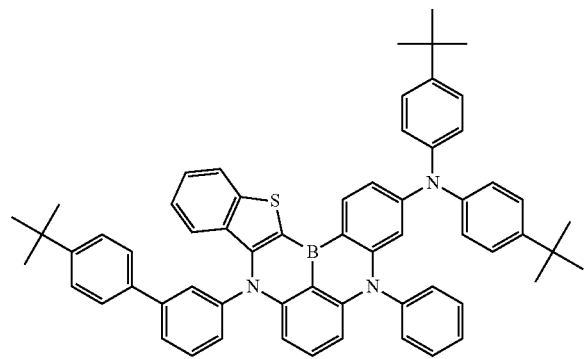
D-147
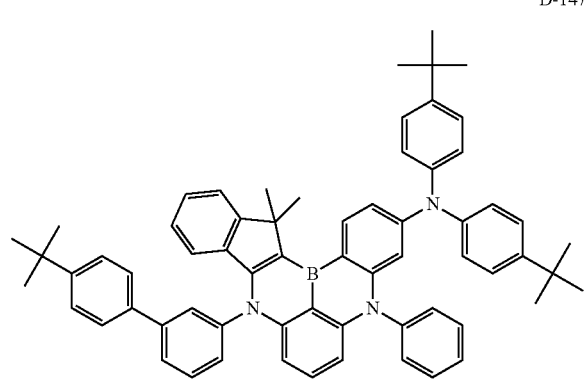
D-148
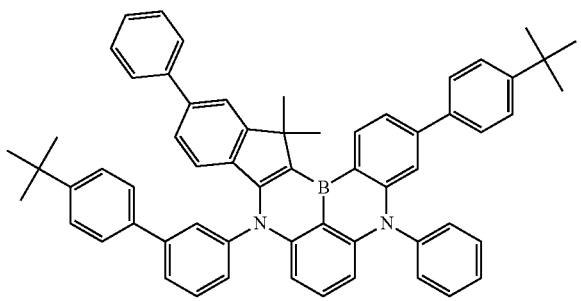
D-149
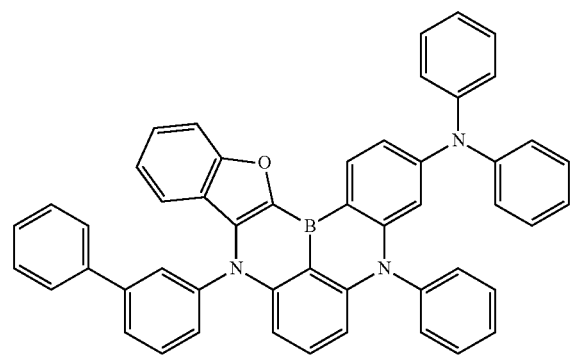
D-150
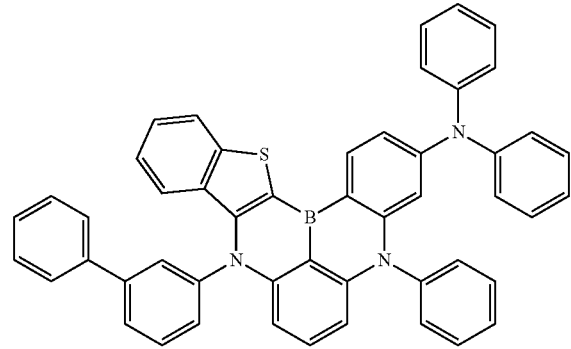
D-151
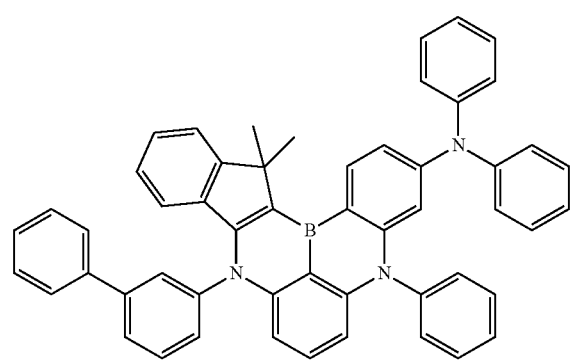

D-152
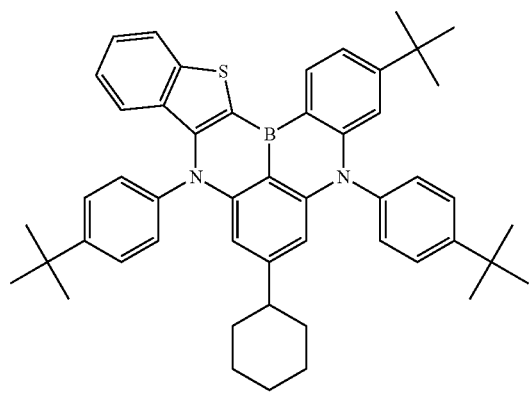
D-153
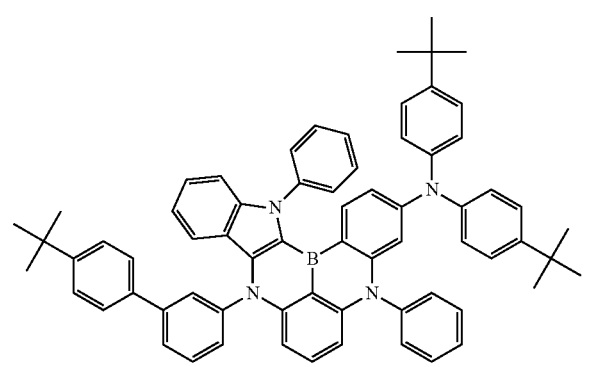
D-154
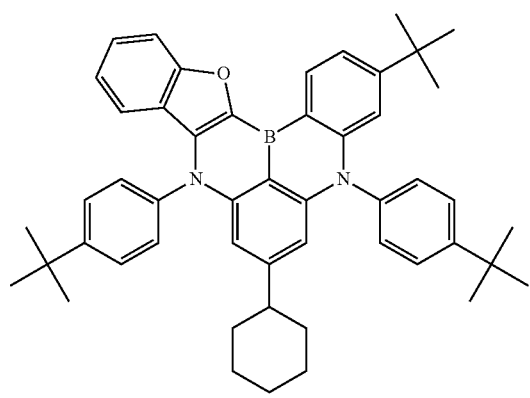
D-155
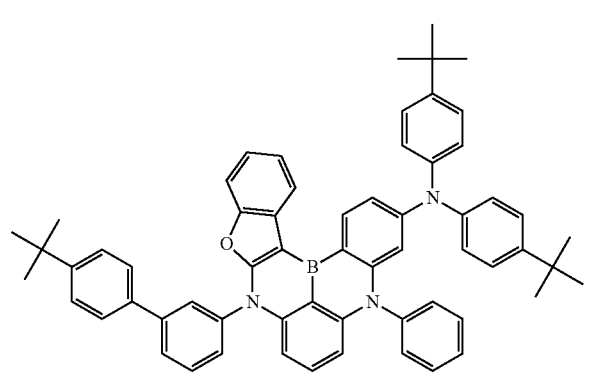
D-156
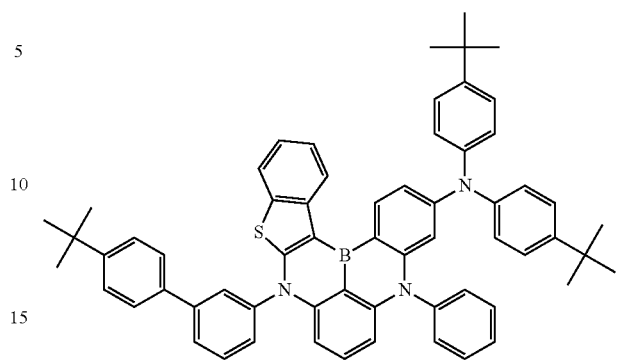
D-157
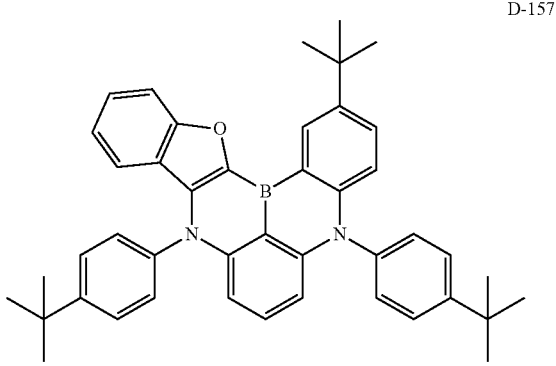
D-158
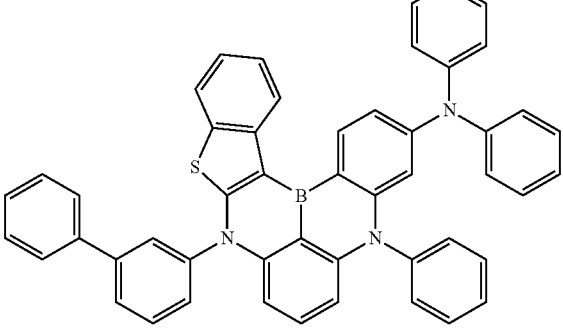
D-159
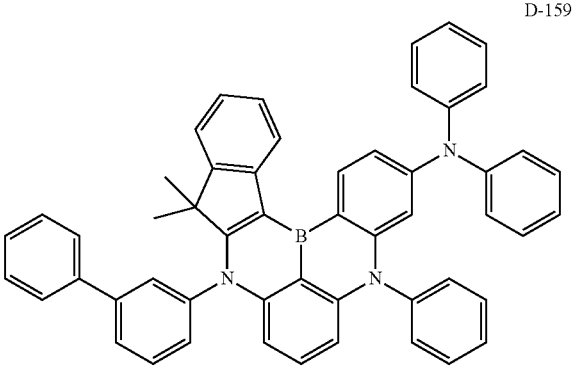

-continued
D-160
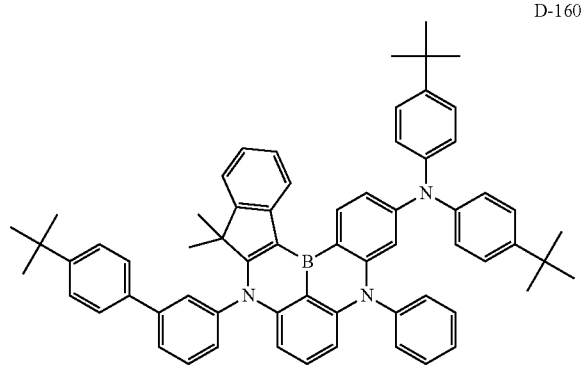
D-161
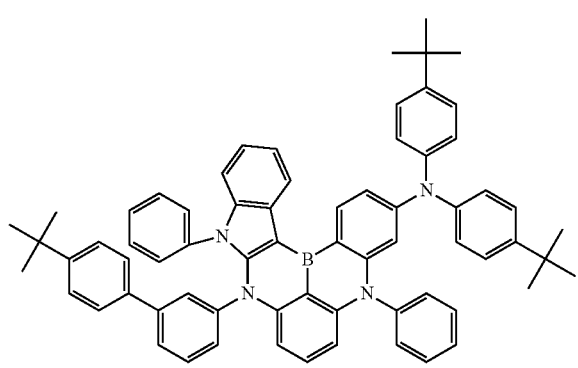
D-162
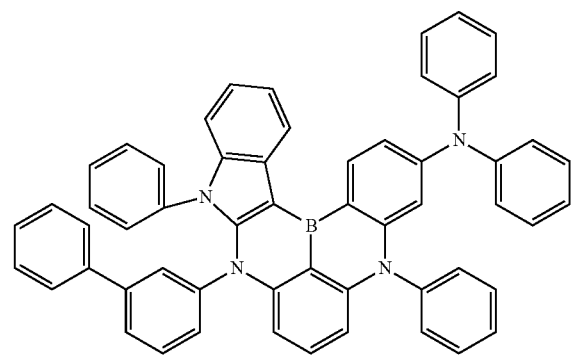
D-163
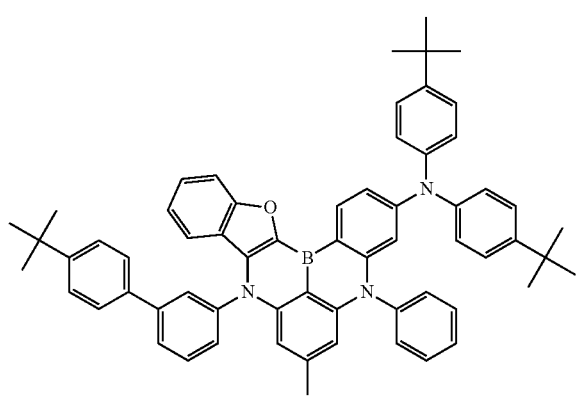
-continued
D-164
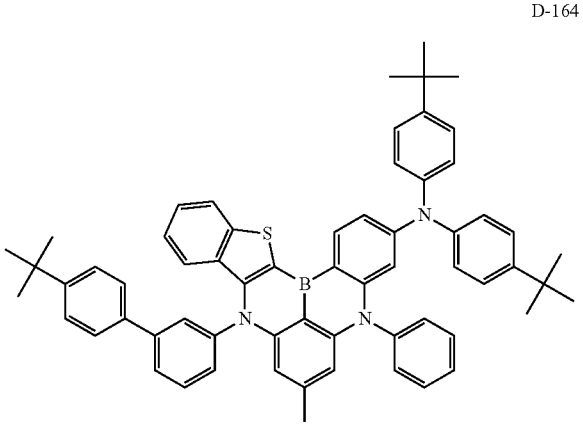
D-165
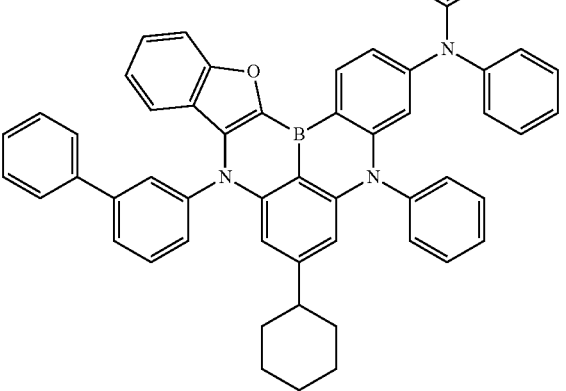
D-166
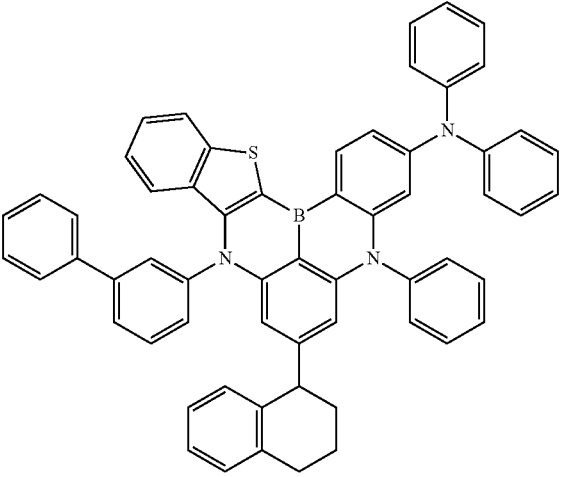

-continued
D-167
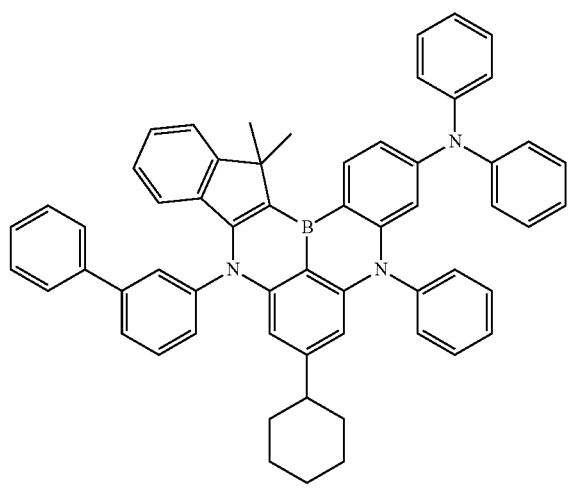
D-168
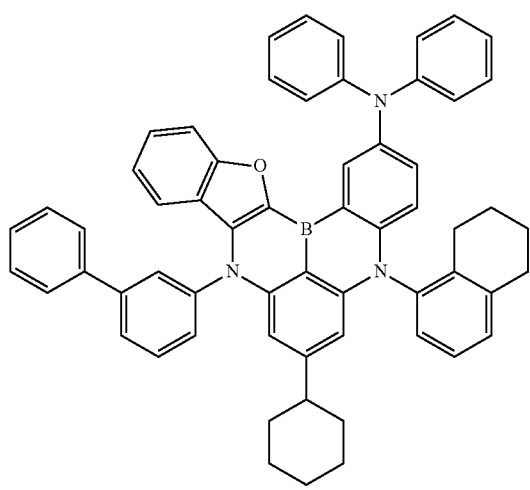
D-169
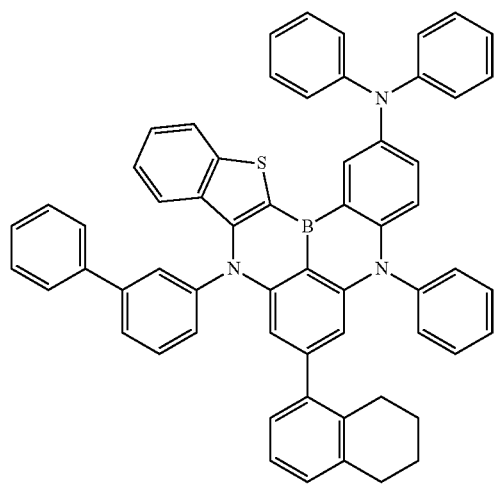
-continued
D-170
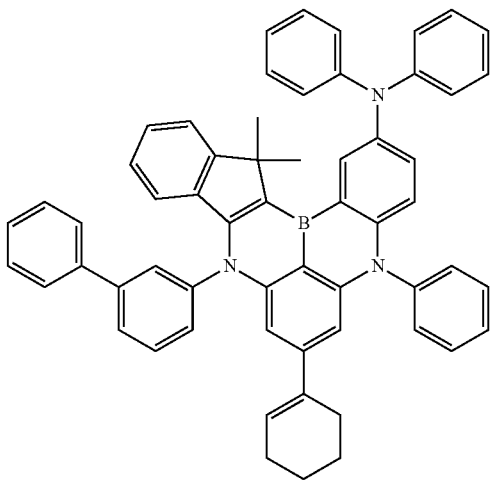
D-171
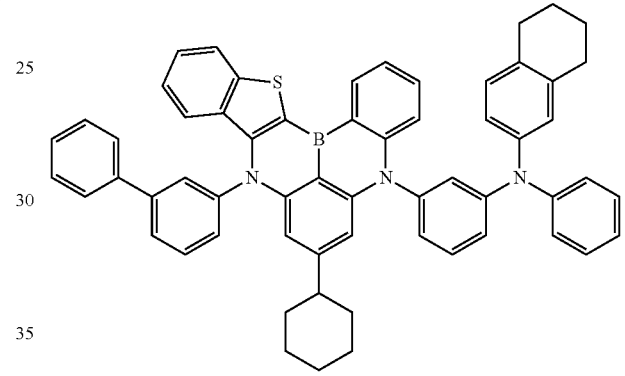
D-172
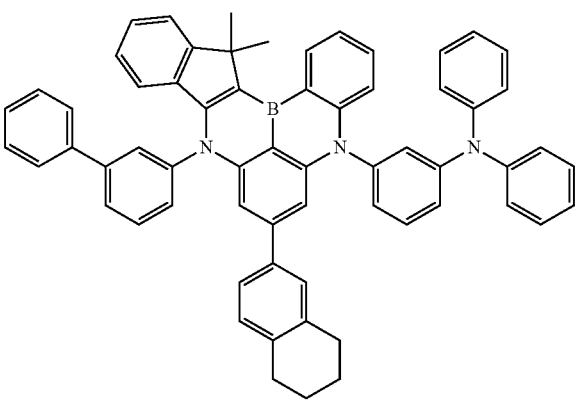

D-173
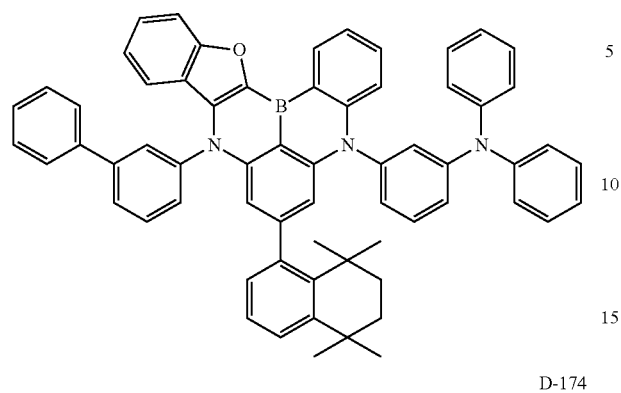
D-174
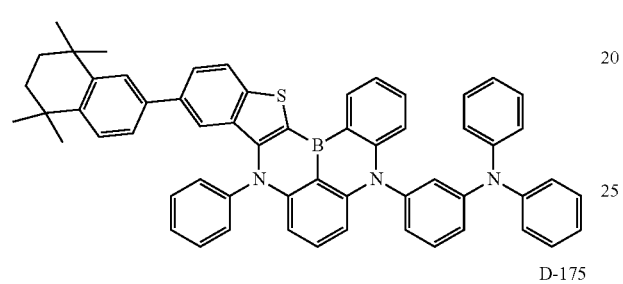
D-175
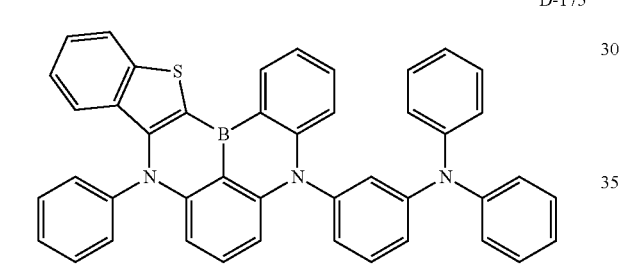
D-176
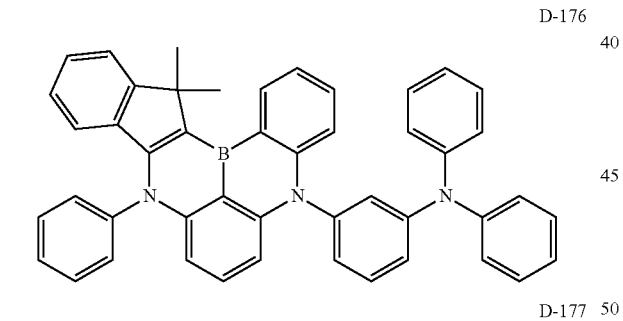
D-177
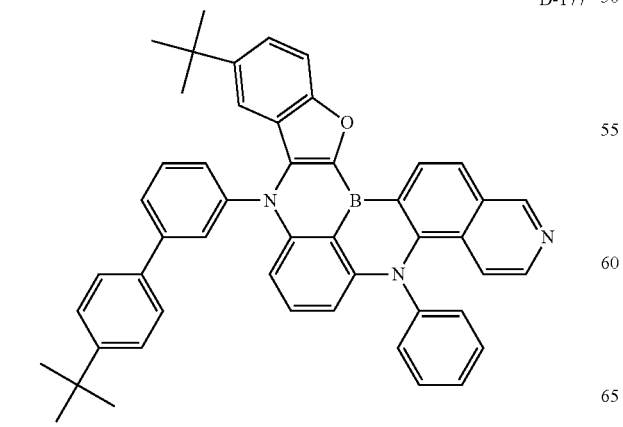
D-178
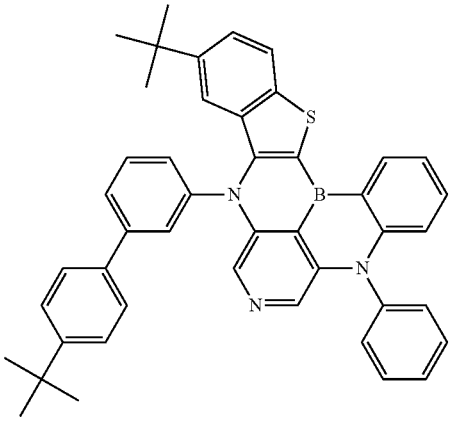
D-179
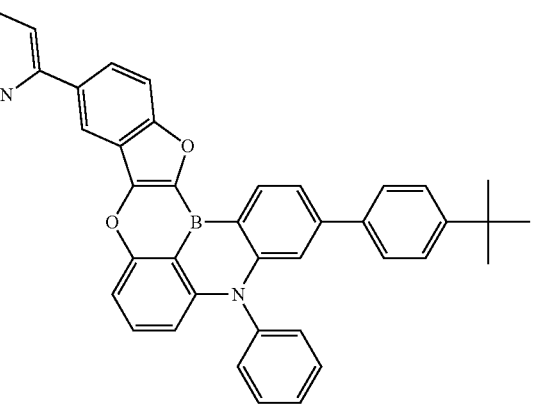
D-180
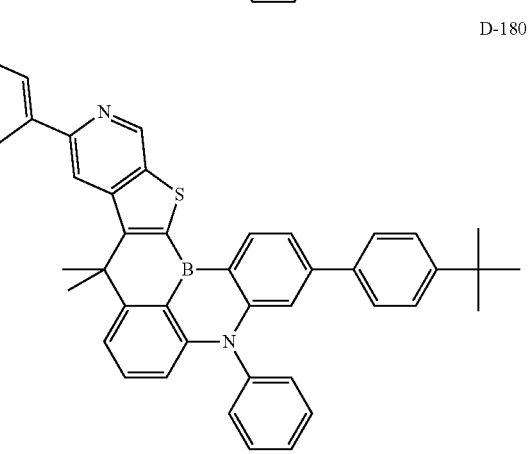
D-181
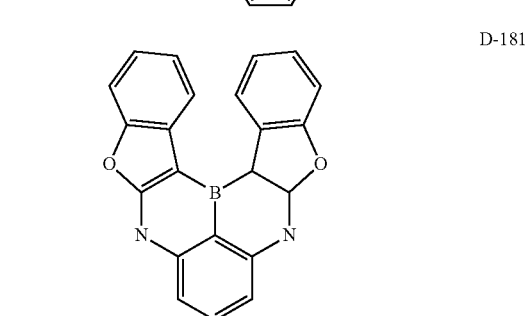

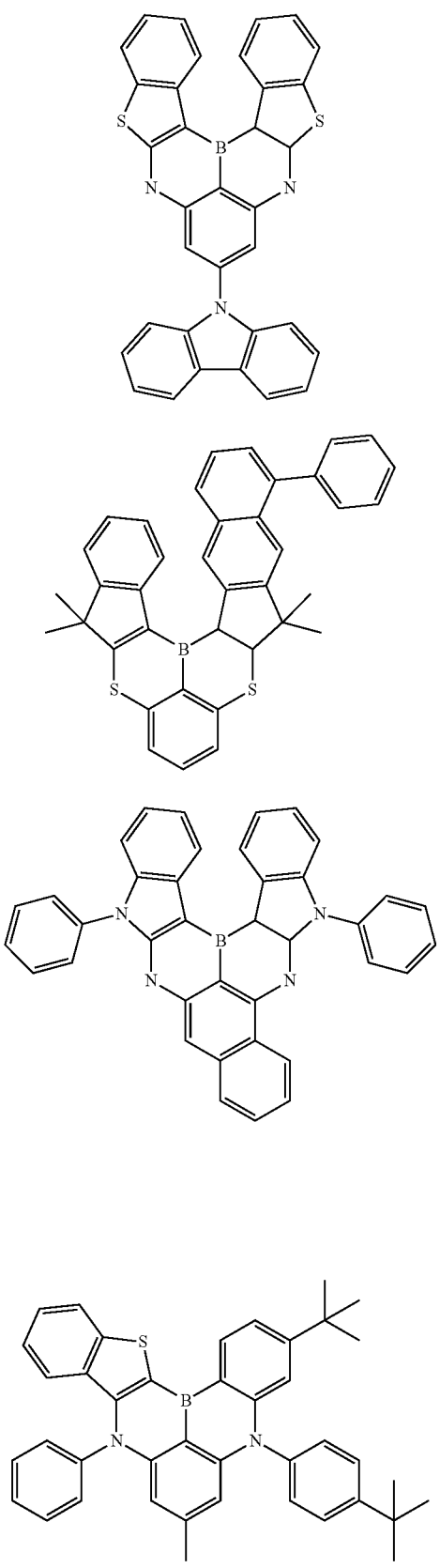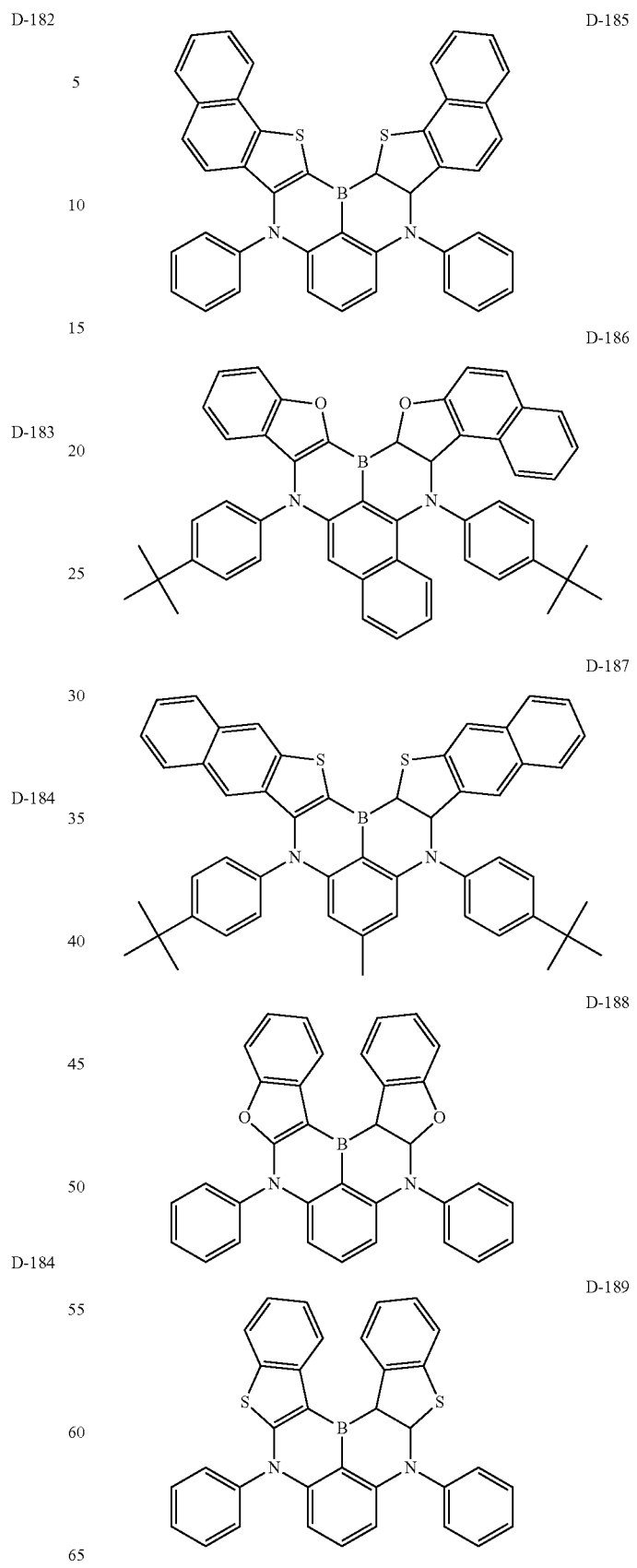

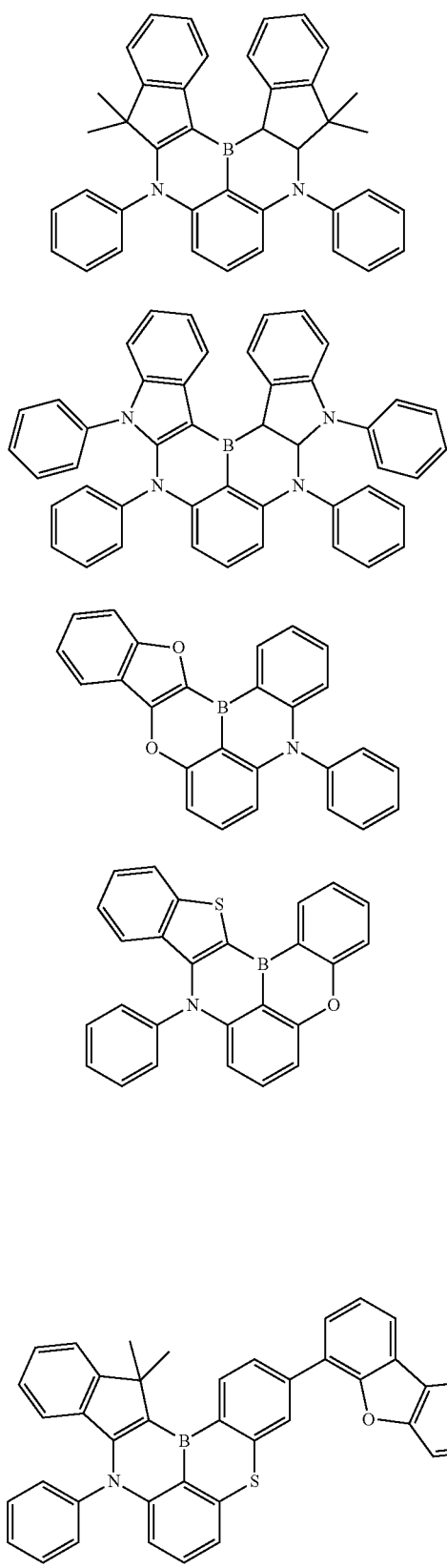
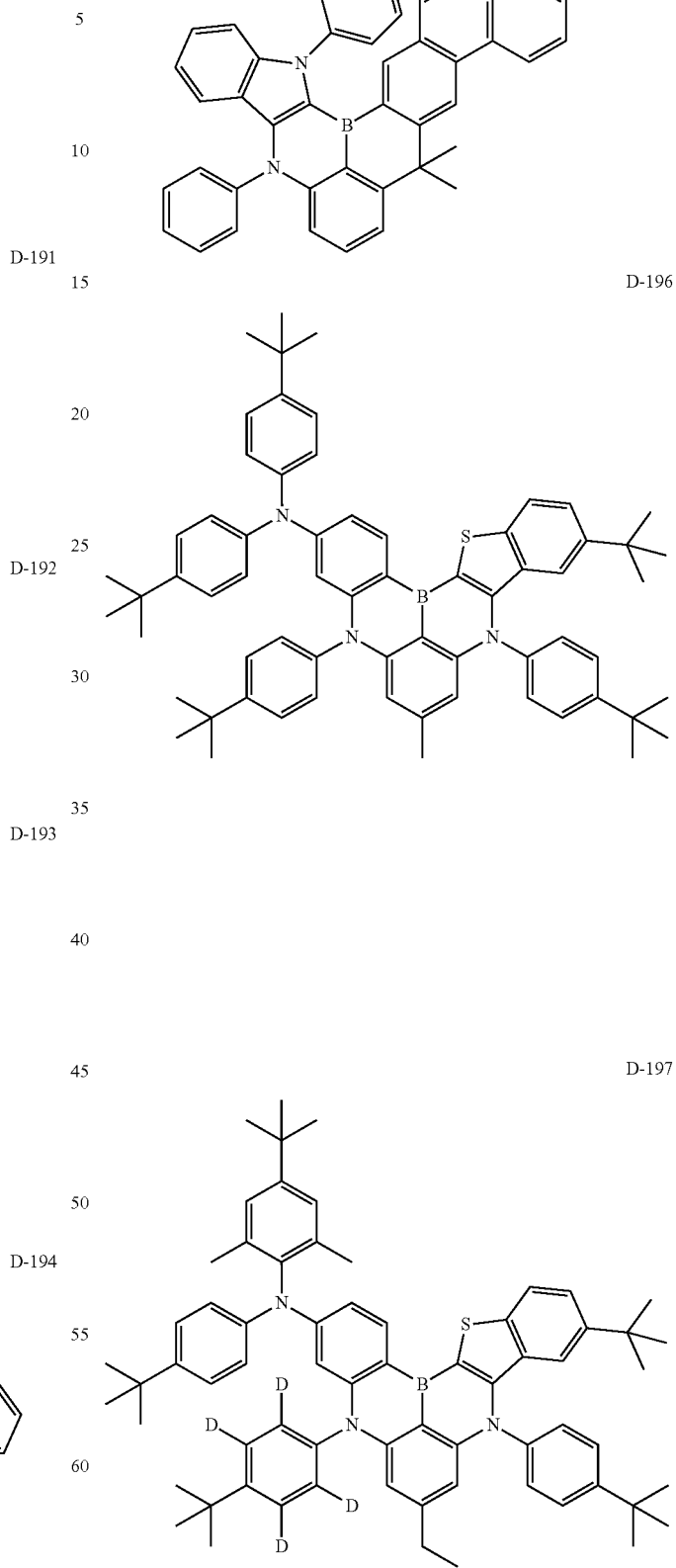

D-198
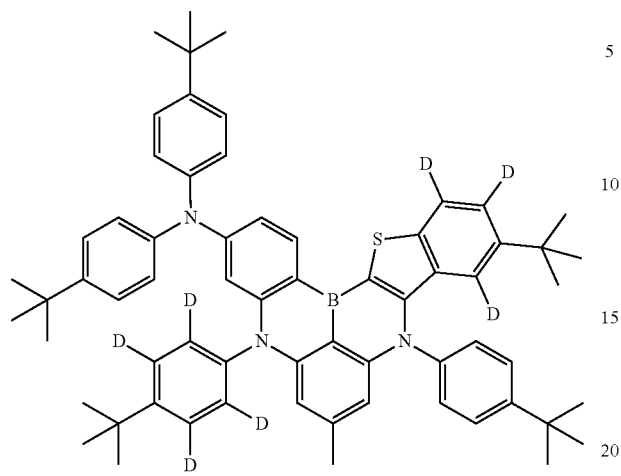
D-201
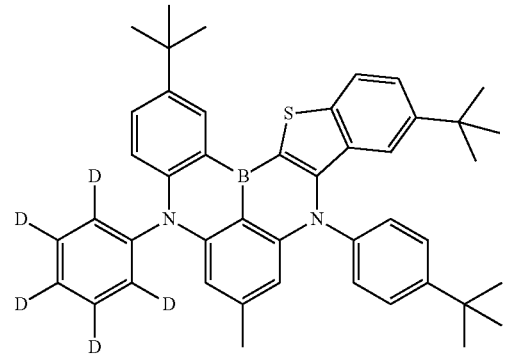
D-199
D-202
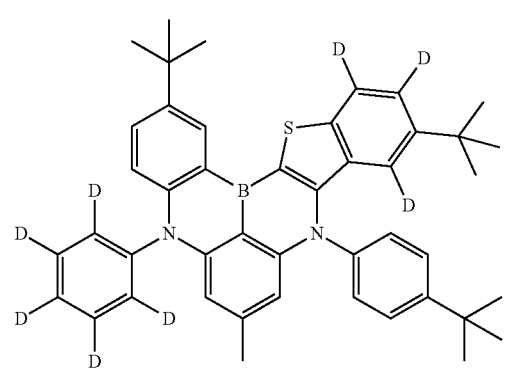
D-200
D-203
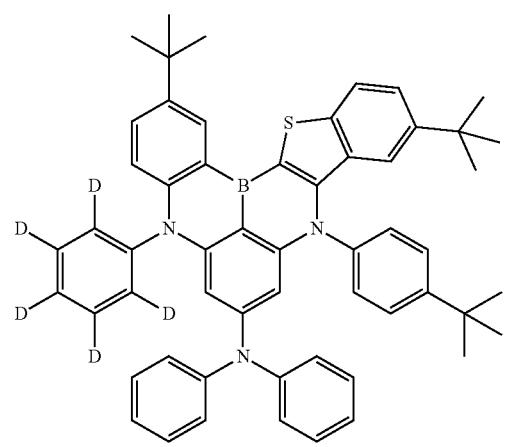
D-204
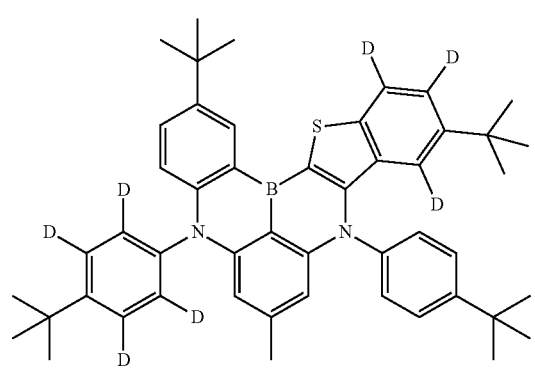
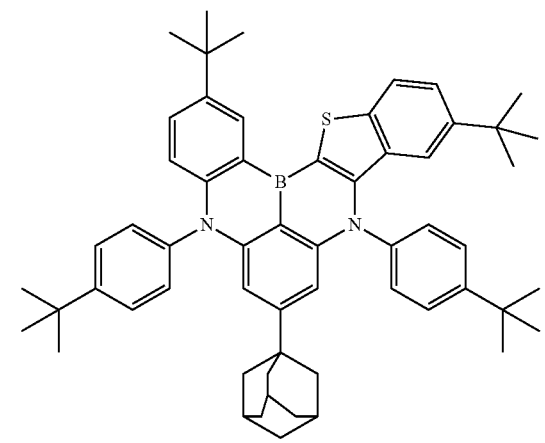

D-205

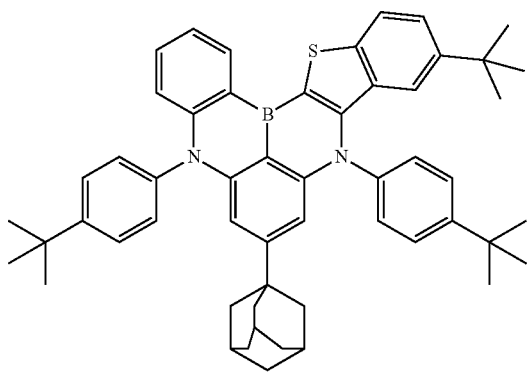

D-206

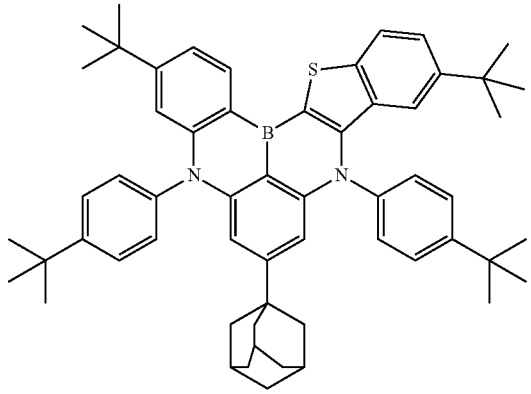

D-207

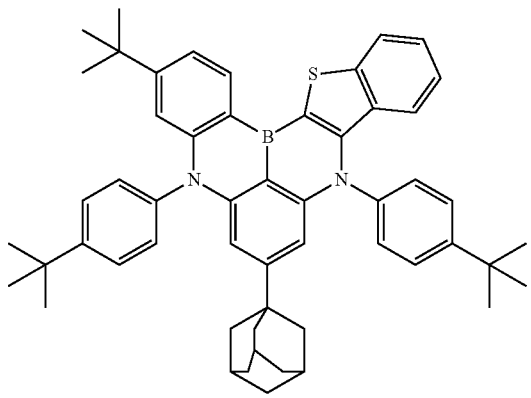

D-208

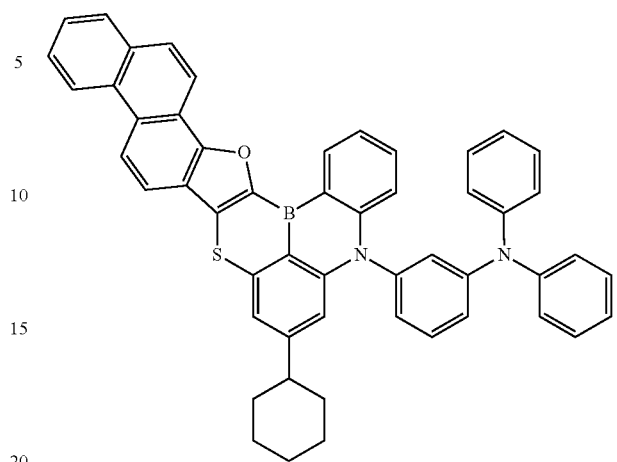

D-209

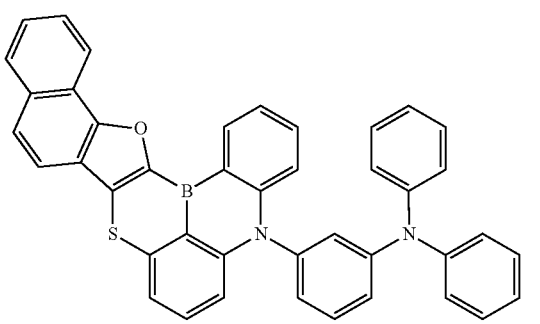

D-210

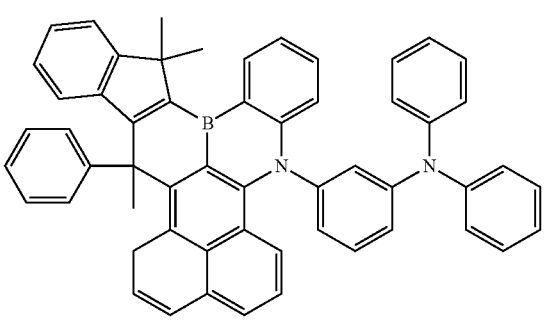

The content of the dopant in the light emitting layer is typically selected in the range of about 0.01 to about 20 parts by weight, based on about 100 parts by weight of the host, but is not limited thereto.

One or more dopant compounds other than the dopant compound represented by Formula D-1 or D-2 may be mixed or stacked in the light emitting layer of the organic electroluminescent device according to the present invention.

In conclusion, the light emitting layer of the organic electroluminescent device according to the present invention may include a mixture of the host represented by Formula A and one or more other host materials and the dopant represented by Formula D-1 or D-2 and one or more other dopant materials, which may optionally form a plurality of layers.

The organic layers of the organic electroluminescent device according to the present invention may form a monolayer structure. Alternatively, the organic layers may have a multilayer stack structure. For example, the organic layers may have a structure including a hole injecting layer, a hole transport layer, a hole blocking layer, a light emitting layer, an electron blocking layer, an electron transport layer, and an electron injecting layer but is not limited to this structure. The number of the organic layers is not limited and may be increased or decreased. Preferred structures of the organic layers of the organic electroluminescent device according to the present invention will be explained in more detail in the Examples section that follows.

A more detailed description will be given concerning exemplary embodiments of the organic electroluminescent device according to the present invention.

The organic electroluminescent device of the present invention includes an anode, a hole transport layer, a light emitting layer, an electron transport layer, and a cathode. The organic electroluminescent device of the present invention may optionally further include a hole injecting layer between the anode and the hole transport layer and an electron injecting layer between the electron transport layer and the cathode. If necessary, the organic electroluminescent device of the present invention may further include one or two intermediate layers such as a hole blocking layer or an electron blocking layer. The organic electroluminescent device of the present invention may further include one or more organic layers such as a capping layer that have various functions depending on the desired characteristics of the device.

A specific structure of the organic electroluminescent device according to one embodiment of the present invention, a method for fabricating the device, and materials for the organic layers are as follows.

First, an anode material is coated on a substrate to form an anode. The substrate may be any of those used in general electroluminescent devices. The substrate is preferably an organic substrate or a transparent plastic substrate that is excellent in transparency, surface smoothness, ease of handling, and waterproofness. A highly transparent and conductive metal oxide such as indium tin oxide (ITO), indium zinc oxide (IZO), tin oxide ($SnO_2$) or zinc oxide (ZnO) is used as the anode material.

A hole injecting material is coated on the anode by vacuum thermal evaporation or spin coating to form a hole injecting layer. Then, a hole transport material is coated on the hole injecting layer by vacuum thermal evaporation or spin coating to form a hole transport layer.

The hole injecting material is not specially limited so long as it is usually used in the art. Specific examples of such materials include 4,4',4''-tris(2-naphthylphenyl-phenylamino)triphenylamine (2-TNATA), N,N'-di(1-naphthyl)-N,N'-diphenylbenzidine (NPD), N,N'-diphenyl-N,N'-bis(3-methylphenyl)-1,1'-biphenyl-4,4'-diamine (TPD), and N,N'-diphenyl-N,N'-bis(4-(phenyl-m-tolylamino)phenyl)biphenyl-4,4'-diamine (DNTPD).

The hole transport material is not specially limited so long as it is commonly used in the art. Examples of such materials include N,N'-bis(3-methylphenyl)-N,N'-diphenyl-(1,1-biphenyl)-4,4'-diamine (TPD) and N,N'-di(naphthalen-1-yl)-N,N'-diphenylbenzidine (α-NPD).

Subsequently, a hole auxiliary layer and a light emitting layer are sequentially laminated on the hole transport layer. A hole blocking layer may be optionally formed on the light emitting layer by vacuum thermal evaporation or spin coating. The hole blocking layer is formed as a thin film and blocks holes from entering a cathode through the organic light emitting layer. This role of the hole blocking layer prevents the lifetime and efficiency of the device from deteriorating. A material having a very low highest occupied molecular orbital (HOMO) energy level is used for the hole blocking layer. The hole blocking material is not particularly limited so long as it can transport electrons and has a higher ionization potential than the light emitting compound. Representative examples of suitable hole blocking materials include BAlq, BCP, and TPBI.

Examples of materials for the hole blocking layer include, but are not limited to, BAlq, BCP, Bphen, TPBI, NTAZ, $BeBq_2$, OXD-7, and Liq.

An electron transport layer is deposited on the hole blocking layer by vacuum thermal evaporation or spin coating, and an electron injecting layer is formed thereon. A cathode metal is deposited on the electron injecting layer by vacuum thermal evaporation to form a cathode, completing the fabrication of the organic electroluminescent device.

For example, lithium (Li), magnesium (Mg), aluminum (Al), aluminum-lithium (Al—Li), calcium (Ca), magnesium-indium (Mg—In) or magnesium-silver (Mg—Ag) may be used as the metal for the formation of the cathode. The organic electroluminescent device may be of top emission type. In this case, a transmissive material such as ITO or IZO may be used to form the cathode.

A material for the electron transport layer functions to stably transport electrons injected from the cathode. The electron transport material may be any of those known in the art and examples thereof include, but are not limited to, quinoline derivatives, particularly tris(8-quinolinolate)aluminum (Alq3), TAZ, Balq, beryllium bis(benzoquinolin-10-olate (Bebq2), and oxadiazole derivatives such as PBD, BMD, and BND.

Each of the organic layers can be formed by a monomolecular deposition or solution process. According to the monomolecular deposition process, the material for each layer is evaporated into a thin film under heat and vacuum or reduced pressure.

According to the solution process, the material for each layer is mixed with a suitable solvent, and then the mixture is formed into a thin film by a suitable method, such as ink-jet printing, roll-to-roll coating, screen printing, spray coating, dip coating or spin coating.

The organic electroluminescent device of the present invention may further include a light emitting layer composed of a material that emits blue, green or red light light in the wavelength range of 380 nm to 800 nm. That is, the organic electroluminescent device of the present invention may include a plurality of light emitting layers. The blue, green or red light emitting material for the additional light emitting layer may be a fluorescent or phosphorescent material.

The organic electroluminescent device of the present invention can be used in a display or lighting system selected from flat panel displays, flexible displays, monochromatic flat panel lighting systems, white flat panel lighting systems, flexible monochromatic lighting systems, flexible white lighting systems, displays for automotive applications, displays for virtual reality, and displays for augmented reality.

The present invention will be explained more specifically with reference to the following examples. However, it will be obvious to those skilled in the art that these examples are in no way intended to limit the scope of the invention.

SYNTHESIS EXAMPLE 1. SYNTHESIS OF COMPOUND 43

Synthesis Example 1-1. Synthesis of Intermediate 1-a

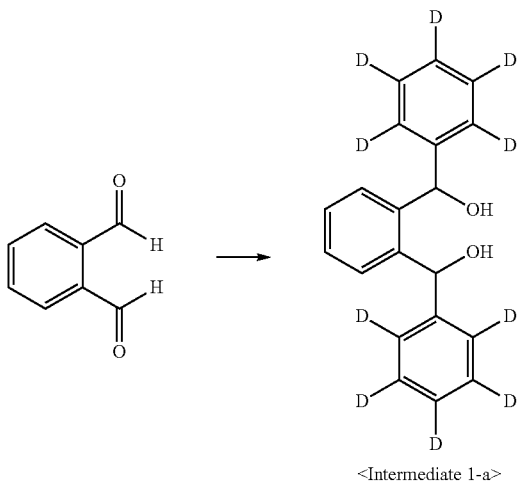 [SMILES: O=Cc1ccccc1C=O ; [2H]c1c([2H])c([2H])c(C(O)c2ccccc2C(O)c2c([2H])c([2H])c([2H])c([2H])c2[2H])c([2H])c1[2H]]

<Intermediate 1-a>

Bromobenzene(d5) (60.4 g, 0.373 mol) and 480 mL of tetrahydrofuran were cooled to −78° C. and stirred in a 2 L reactor. To the cold solution was added dropwise n-butyllithium (223.6 mL, 0.357 mol). The mixture was stirred at the same temperature for 1 h. To the resulting reaction solution was added dropwise a solution of o-phthalaldehyde (20 g, 0.149 mol) in 100 mL of tetrahydrofuran, followed by stirring at room temperature. The reaction was quenched with 200 mL of an aqueous ammonium chloride solution. The reaction solution was extracted with ethyl acetate, concentrated under reduced pressure, and purified by column chromatography to afford Intermediate 1-a (40 g, 89%).

Synthesis Example 1-2: Synthesis of Intermediate 1-b

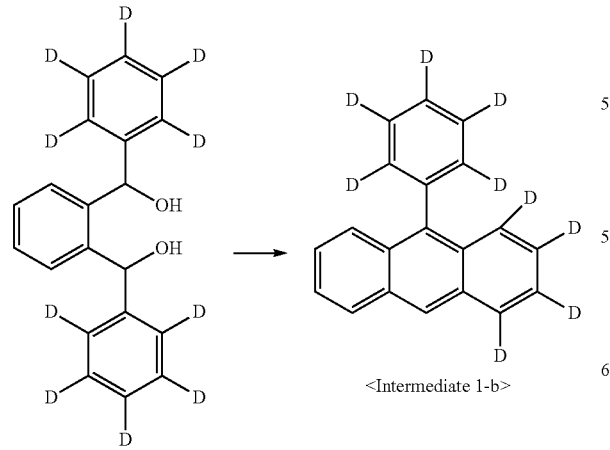

<Intermediate 1-b>

Intermediate 1-a (40 g, 0.133 mol) was dissolved in 200 mL of acetic acid and stirred in a 500 mL reactor. To the solution was added dropwise 2 mL of hydrogen bromide. The mixture was stirred at 80° C. for 2 h. After completion of the reaction, the reaction solution was cooled to room temperature. The reaction solution was slowly poured into a beaker containing 500 mL of distilled water, followed by stirring. The resulting solid was filtered, washed with distilled water, and purified by column chromatography to afford Intermediate 1-b (13 g, 37%).

Synthesis Example 1-3: Synthesis of Intermediate 1-c

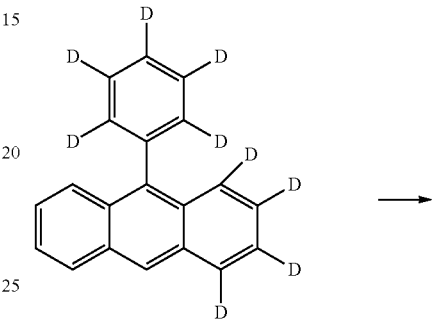

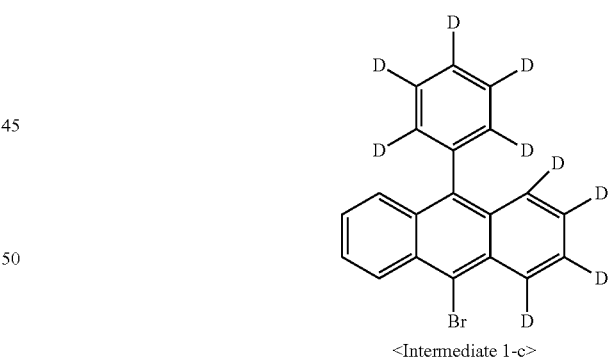

<Intermediate 1-c>

Intermediate 1-b (13.0 g, 0.049 mol) was dissolved in 130 mL of N,N-dimethylamide in a 500 mL reactor. The solution was stirred at room temperature. To the solution was added dropwise a solution of N-bromosuccinimide (10.54 g, 0.059 mol) in 40 mL of N,N-dimethylamide. The completion of the reaction was confirmed by thin layer chromatography. The reaction solution was poured into a beaker containing 500 mL of distilled water, followed by stirring. The resulting solid was filtered, washed with distilled water, and purified by column chromatography to afford Intermediate 1-c (14 g, 83%).

Synthesis Example 1-4: Synthesis of Intermediate 1-d

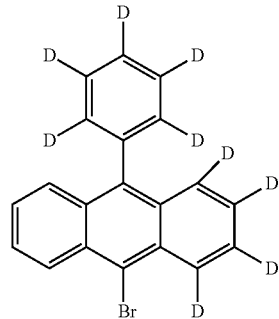

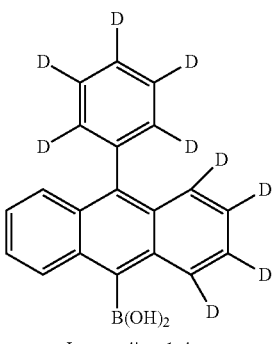

<Intermediate 1-d>

Intermediate 1-c (50 g, 0.146 mol) were dissolved in 500 mL of tetrahydrofuran in a 500 mL reactor. The solution was cooled to −78° C. and n-butyllithium (100 mL, 0.161 mol) was added dropwise thereto. The mixture was stirred for 5 h. To the mixture was added trimethyl borate (18 mL, 0.161 mol), followed by stirring at room temperature overnight. After completion of the reaction, the reaction mixture was acidified with 2 N hydrochloric acid and recrystallized to yield Intermediate 1-d (25 g, 56%).

Synthesis Example 1-5: Synthesis of Intermediate 1-e

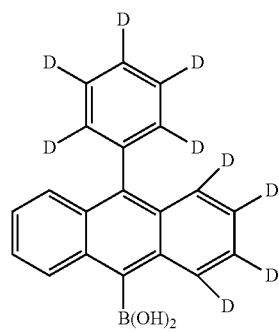 + 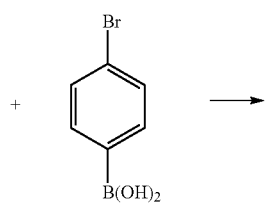 

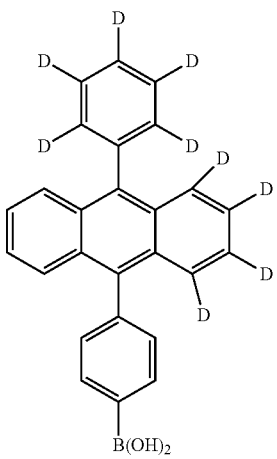

<Intermediate 1-e>

Intermediate 1-d (30 g, 0.098 mol), (4-bromophenyl)boronic acid (23.5 g, 0.117 mol), palladium acetate (0.4 g, 0.002 mol), potassium carbonate (27 g, 0.195 mol), and Sphos (1.6 g, 0.004 mol) were placed in a 500 mL reactor, and 200 mL of toluene, 90 mL of ethanol, and 60 mL of distilled water were added thereto. The temperature of the reactor was raised to 90° C., followed by stirring overnight. After completion of the reaction, the temperature of the reactor was lowered to room temperature. The reaction mixture was extracted with methanol. The organic layer was separated, concentrated under reduced pressure, purified by column chromatography, and recrystallized from toluene and acetone to yield Intermediate 1-e (12 g, 32%).

Synthesis Example 1-6: Synthesis of Compound 43

83

-continued

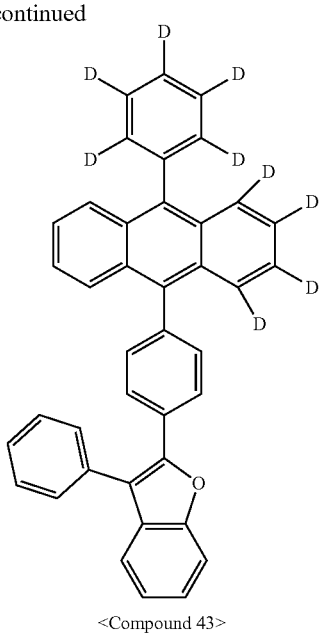

<Compound 43>

Compound 43 (yield 30%) was synthesized in the same manner as in Synthesis Example 1-5, except that Intermediate 1-e and 2-bromo-3-phenylbenzofuran were used instead of Intermediate 1-d and (4-bromophenyl)boronic acid, respectively.

MS (MALDI-TOF): m/z 531.25 [M$^+$]

SYNTHESIS EXAMPLE 2. SYNTHESIS OF COMPOUND 56

Synthesis Example 2-1: Synthesis of Intermediate 2-a

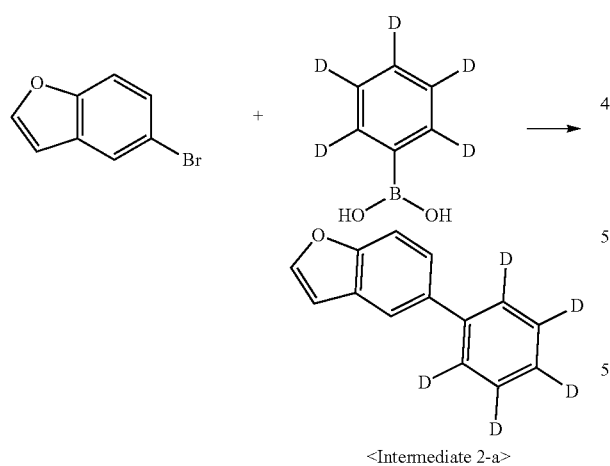

<Intermediate 2-a>

5-Bromobenzofuran (30 g, 0.152 mol), (phenyl-d5)boronic acid (23.2 g, 0.183 mol), tetrakis(triphenylphosphine)palladium(0) (5.3 g, 0.005 mol), potassium carbonate (42.1 g, 0.305 mol), 300 mL of THF, and 120 mL of distilled water were placed in a 500 mL reactor. The mixture was stirred under reflux for 12 h. After completion of the reaction, the reaction solution was allowed to stand for layer separation.

84

The organic layer was concentrated under reduced pressure and purified by column chromatography to afford Intermediate 2-a (21.2 g, 70%).

Synthesis Example 2-2: Synthesis of Intermediate 2-b

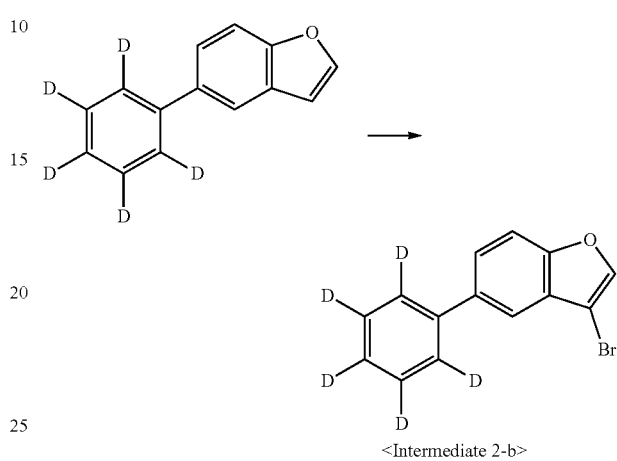

<Intermediate 2-b>

Intermediate 2-a (21.2 g, 0.106 mol) and dichloromethane were placed in a 500 mL reactor. The mixture was cooled to −10° C. and bromine was added thereto. The resulting mixture was stirred for 1 h. To the reaction mixture was added an aqueous sodium thiosulfate solution, followed by stirring. The mixture was allowed to stand for layer separation. The organic layer was concentrated under reduced pressure, added with ethanol, cooled to −10° C., and added with an ethanolic solution of potassium hydroxide. The mixture was heated to reflux for 4 h. After completion of the reaction, the reaction solution was allowed to stand for layer separation. The organic layer was concentrated under reduced pressure and purified by column chromatography to afford Intermediate 2-b (20 g, 70%).

Synthesis Example 2-3: Synthesis of Compound 56

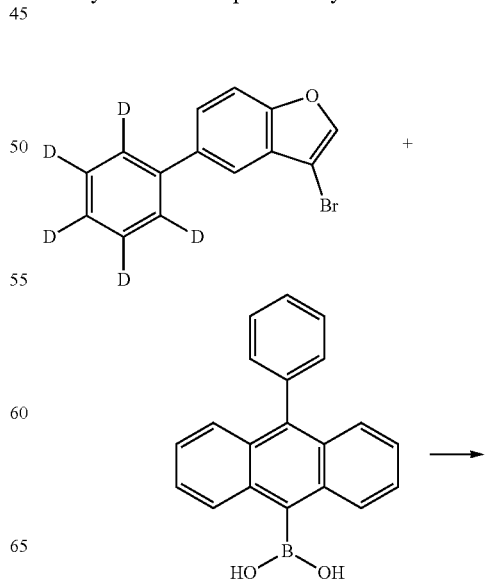

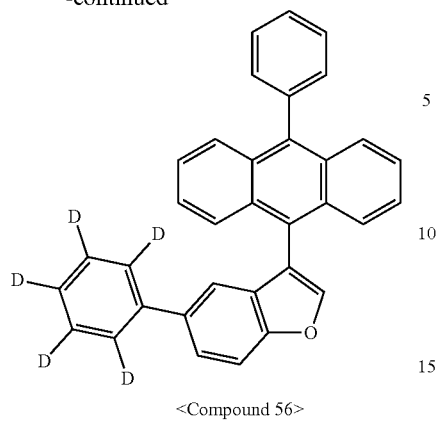

<Compound 56>

Intermediate 2-b (20 g, 0.072 mol), 10-phenyl-anthracene-9-boronic acid (25.7 g, 0.086 mol), tetrakis(triphenylphosphine)palladium(0) (2.5 g, 0.002 mol), potassium carbonate (29.8 g, 0.216 mol), 140 mL of toluene, 60 mL of ethanol, and 60 mL of distilled water were refluxed for 12 h. After completion of the reaction, the reaction solution was allowed to stand for layer separation. The organic layer was concentrated under reduced pressure, purified by column chromatography, and recrystallized to give Compound 56 (10 g, 32%).

MS (MALDI-TOF): m/z 451.20 [M$^+$]

SYNTHESIS EXAMPLE 3. SYNTHESIS OF COMPOUND 58

Synthesis Example 3-1: Synthesis of Intermediate 3-a

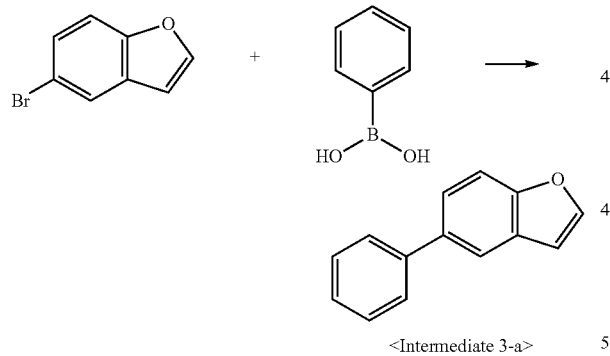

<Intermediate 3-a>

Intermediate 3-a (yield 77%) was synthesized in the same manner as in Synthesis Example 2-1, except that phenylboronic acid was used instead of (phenyl-d5)boronic acid.

Synthesis Example 3-2: Synthesis of Intermediate 3-b

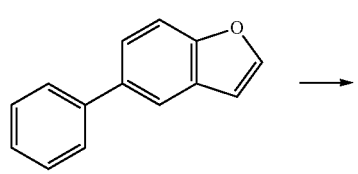

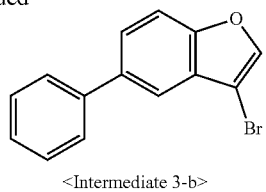

<Intermediate 3-b>

Intermediate 3-b (yield 70%) was synthesized in the same manner as in Synthesis Example 2-2, except that Intermediate 3-a was used instead of Intermediate 2-a.

Synthesis Example 3-3: Synthesis of Intermediate 3-c

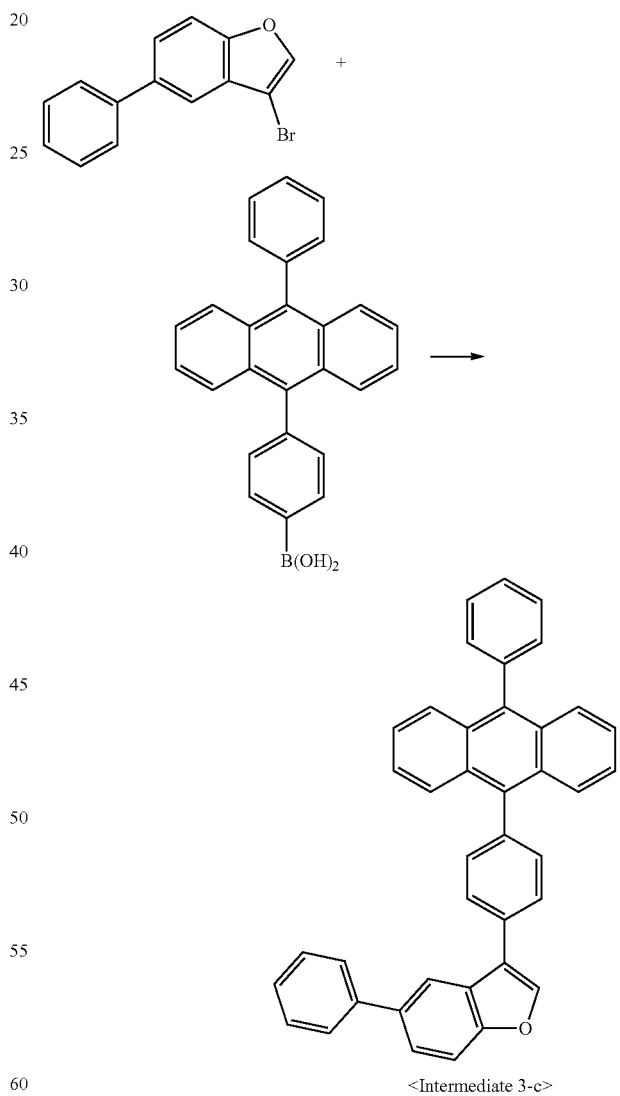

<Intermediate 3-c>

Intermediate 3-c (yield 74%) was synthesized in the same manner as in Synthesis Example 2-3, except that Intermediate 3-b and 4-(10-phenyl-9-anthryl)phenylboronic acid were used instead of Intermediate 2-b and 10-phenyl-anthracene-9-boronic acid, respectively.

Synthesis Example 3-4: Synthesis of Intermediate 3-d

Synthesis Example 3-5: Synthesis of Compound 58

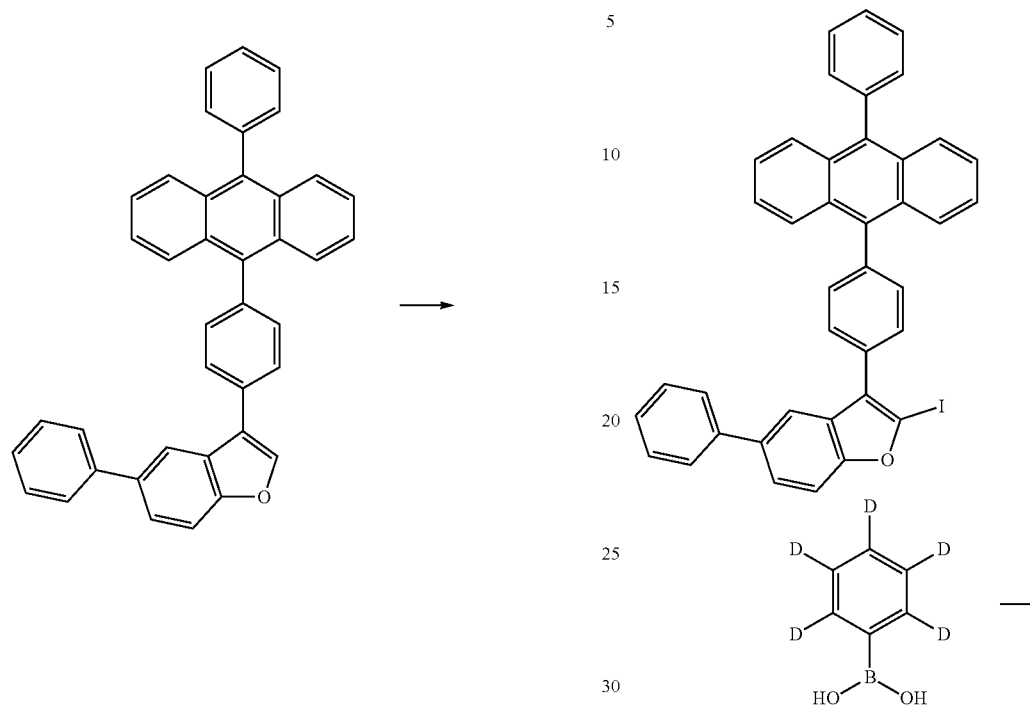

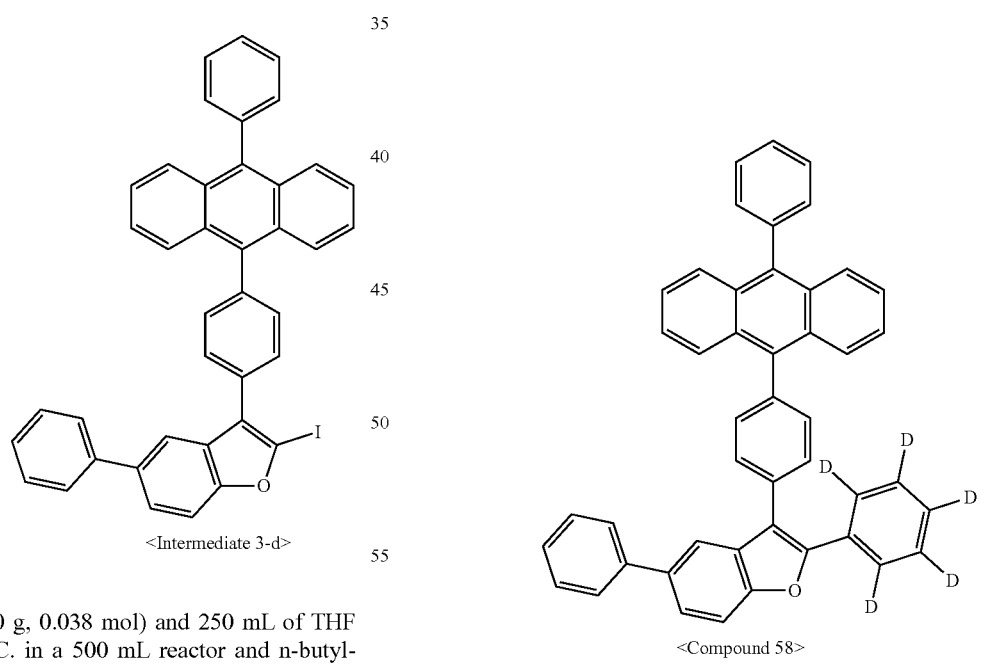

<Compound 58>

Intermediate 3-c (20 g, 0.038 mol) and 250 mL of THF were cooled to −50° C. in a 500 mL reactor and n-butyl-lithium (1.6 M) was added thereto. After 1 h, iodine was slowly added. The temperature was gradually raised to room temperature. To the mixture was added an aqueous sodium thiosulfate solution at room temperature. The resulting mixture was allowed to stand for layer separation. The organic layer was concentrated under reduced pressure and purified by column chromatography to afford Intermediate 3-d (16 g, 65%).

Compound 58 (yield 50%) was synthesized in the same manner as in Synthesis Example 2-3, except that Intermediate 3-d and (phenyl-d5)boronic acid were used instead of Intermediate 2-b and 10-phenyl-anthracene-9-boronic acid, respectively.

MS (MALDI-TOF): m/z 603.26 [M$^+$]

89

SYNTHESIS EXAMPLE 4. SYNTHESIS OF COMPOUND 61

Synthesis Example 4-1: Synthesis of Intermediate 4-a

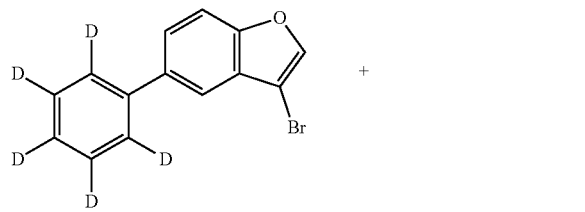

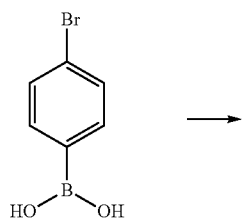

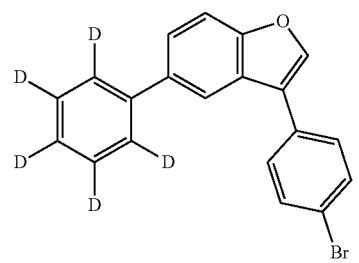

<Intermediate 4-a>

Intermediate 4-a (yield 71%) was synthesized in the same manner as in Synthesis Example 2-3, except that 4-bromophenylboronic acid was used instead of 10-phenyl-anthracene-9-boronic acid.

Synthesis Example 4-2: Synthesis of Compound 61

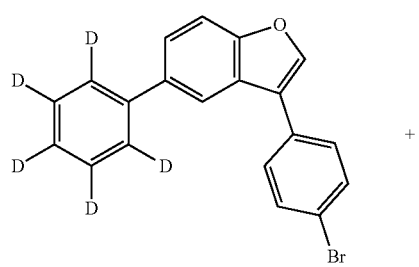

90

-continued

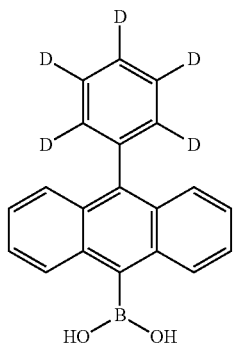

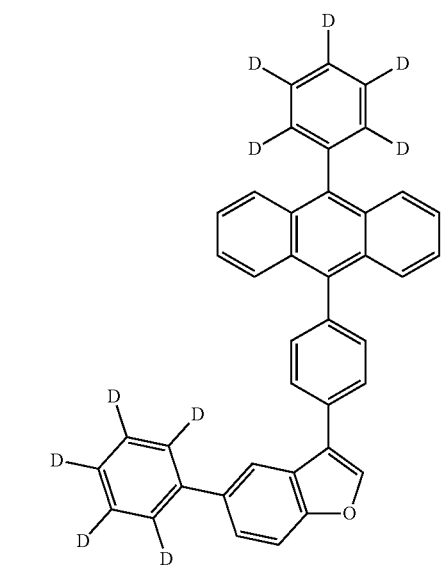

<Compound 61>

Compound 61 (yield 30%) was synthesized in the same manner as in Synthesis Example 2-3, except that Intermediate 4-a and 10-phenyl (d5)-anthracene-9-boronic acid were used instead of Intermediate 2-b and 10-phenyl-anthracene-9-boronic acid, respectively.

MS (MALDI-TOF): m/z 532.26 [M$^+$]

SYNTHESIS EXAMPLE 5. SYNTHESIS OF COMPOUND 66

Synthesis Example 5-1: Synthesis of Compound 66

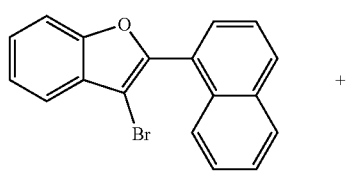

-continued

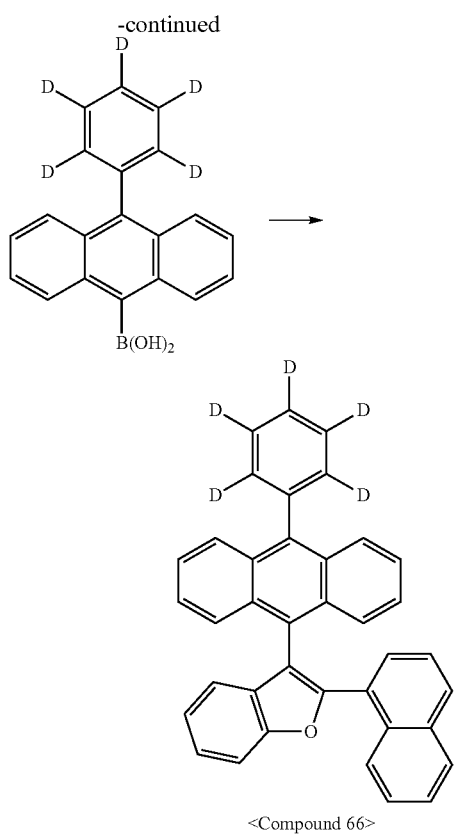
<Compound 66>

Compound 66 (yield 30%) was synthesized in the same manner as in Synthesis Example 2-3, except that 3-bromo-2-naphthalen-1-yl benzofuran and 10-phenyl(d5)-anthracene-9-boronic acid were used instead of Intermediate 2-b and 10-phenyl-anthracene-9-boronic acid, respectively.

MS (MALDI-TOF): m/z 501.21 [M$^+$]

SYNTHESIS EXAMPLE 6. SYNTHESIS OF COMPOUND 14

Synthesis Example 6-1: Synthesis of Intermediate 6-a

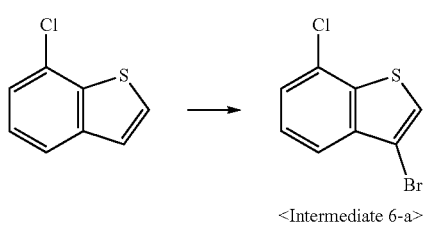 [SMILES: Clc1cccc2ccsc12 ; Clc1cccc2c(Br)csc12]
<Intermediate 6-a>

7-Chlorobenzo[b]thiophene (30 g, 0.178 mol) and DMF were stirred in a 500 mL reactor and NBS was added thereto. The mixture was refluxed with stirring for 6 h. Distilled water was added to the reaction solution. The resulting mixture was allowed to stand for layer separation. The organic layer was concentrated under reduced pressure and purified by column chromatography to afford Intermediate 6-a (27 g, 62%).

Synthesis Example 6-2: Synthesis of Intermediate 6-b

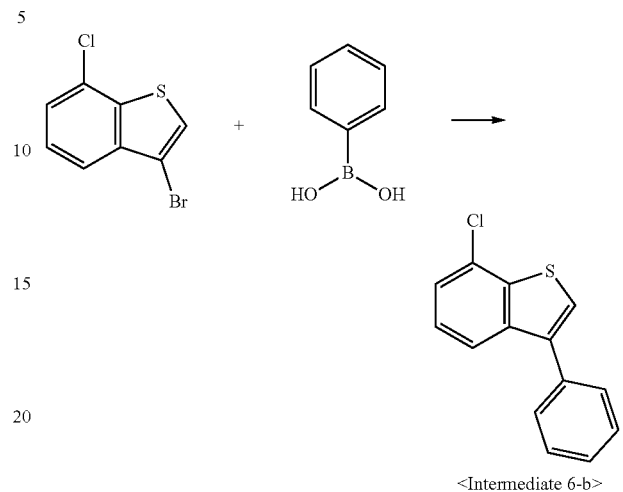
<Intermediate 6-b>

Intermediate 6-b (yield 70%) was synthesized in the same manner as in Synthesis Example 2-1, except that Intermediate 6-a and phenylboronic acid were used instead of 5-bromobenzofuran and (phenyl-d5)boronic acid, respectively.

Synthesis Example 6-3: Synthesis of Intermediate 6-c

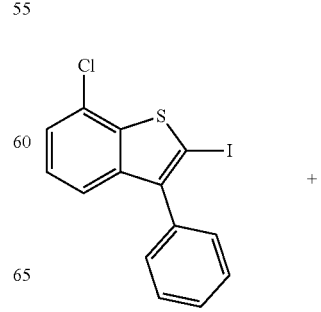
<Intermediate 6-c>

Intermediate 6-c (yield 70%) was synthesized in the same manner as in Synthesis Example 3-4, except that Intermediate 6-b was used instead of Intermediate 3-c.

Synthesis Example 6-4: Synthesis of Intermediate 6-d

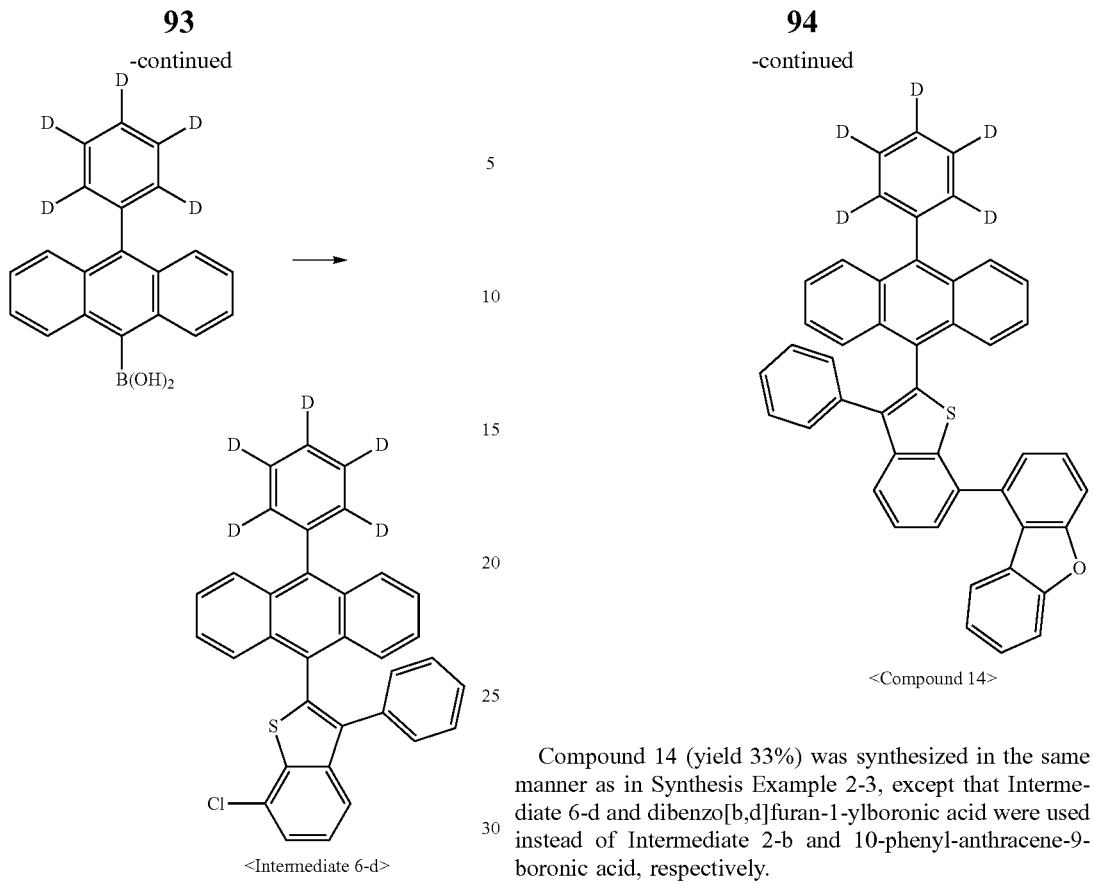

<Intermediate 6-d>

Intermediate 6-d (yield 68%) was synthesized in the same manner as in Synthesis Example 2-3, except that Intermediate 6-c and 10-phenyl(d5)-anthracene-9-boronic acid were used instead of Intermediate 2-b and 10-phenyl-anthracene-9-boronic acid, respectively.

Synthesis Example 6-5: Synthesis of Compound 14

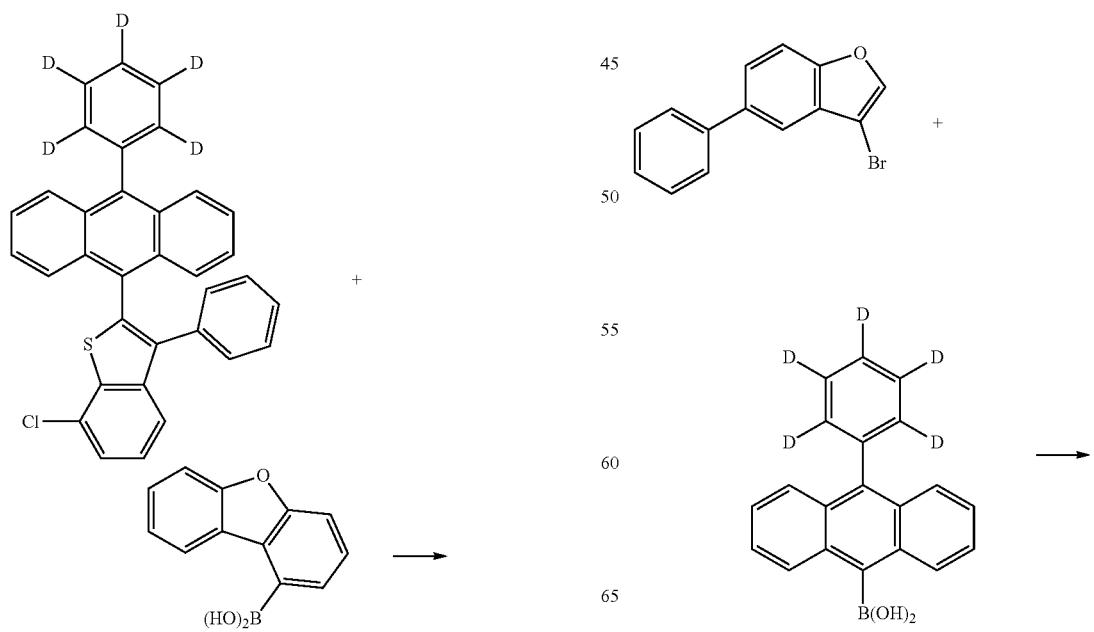

<Compound 14>

Compound 14 (yield 33%) was synthesized in the same manner as in Synthesis Example 2-3, except that Intermediate 6-d and dibenzo[b,d]furan-1-ylboronic acid were used instead of Intermediate 2-b and 10-phenyl-anthracene-9-boronic acid, respectively.

MS (MALDI-TOF): m/z 633.22 [M$^+$]

SYNTHESIS EXAMPLE 7. SYNTHESIS OF COMPOUND 89

Synthesis Example 7-1: Synthesis of Intermediate 7-a

95

-continued

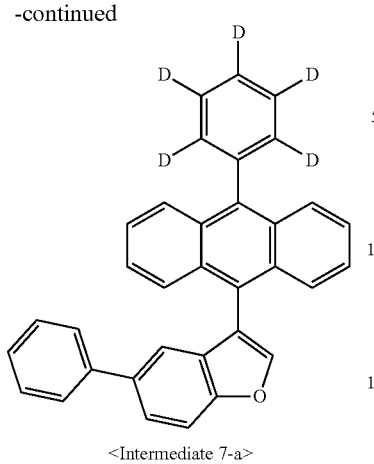

<Intermediate 7-a>

Intermediate 7-a (yield 70%) was synthesized in the same manner as in Synthesis Example 3-3, except that 10-(phenyl-d5)-anthracene-9-boronic acid was used instead of 4-(10-phenyl-9-anthryl)phenylboronic acid.

Synthesis Example 7-2: Synthesis of Intermediate 7-b

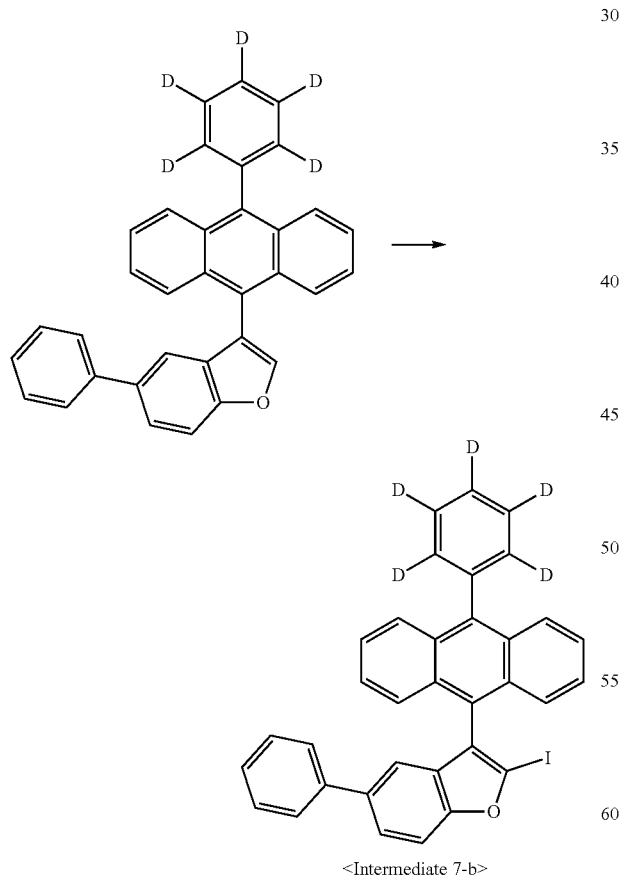

<Intermediate 7-b>

Intermediate 7-b (yield 63%) was synthesized in the same manner as in Synthesis Example 3-4, except that Intermediate 7-a was used instead of Intermediate 3-c.

96

Synthesis Example 7-3: Synthesis of Compound 89

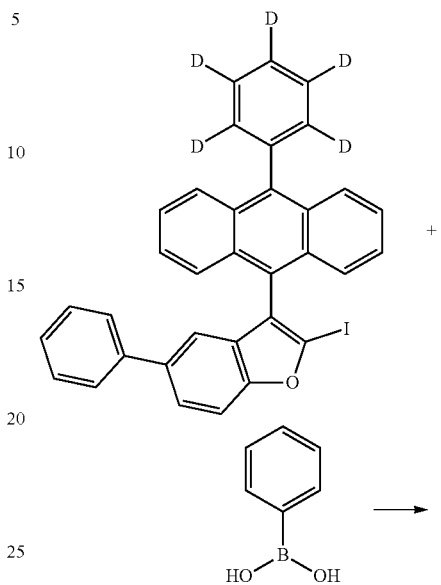

<Compound 89>

Compound 89 (yield 51%) was synthesized in the same manner as in Synthesis Example 3-5, except that Intermediate 7-b and phenylboronic acid were used instead of Intermediate 3-d and (phenyl-d5)boronic acid, respectively.

MS (MALDI-TOF): m/z 527.23 [M$^+$]

SYNTHESIS EXAMPLE 8. SYNTHESIS OF COMPOUND 90

Synthesis Example 8-1: Synthesis of Intermediate 8-a

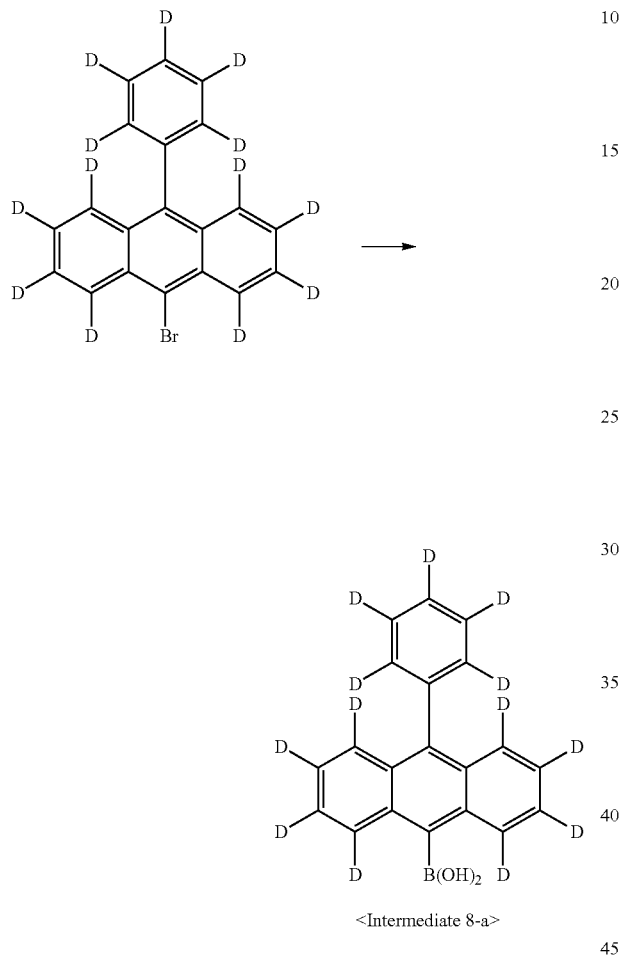

<Intermediate 8-a>

Intermediate 8-a (yield 55%) was synthesized in the same manner as in Synthesis Example 1-4, except that (anthracene-d8)-9-bromo-10-(phenyl-d5) was used instead of Intermediate 1-c.

Synthesis Example 8-2: Synthesis of Intermediate 8-b

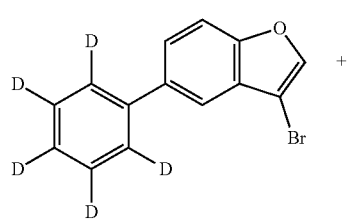

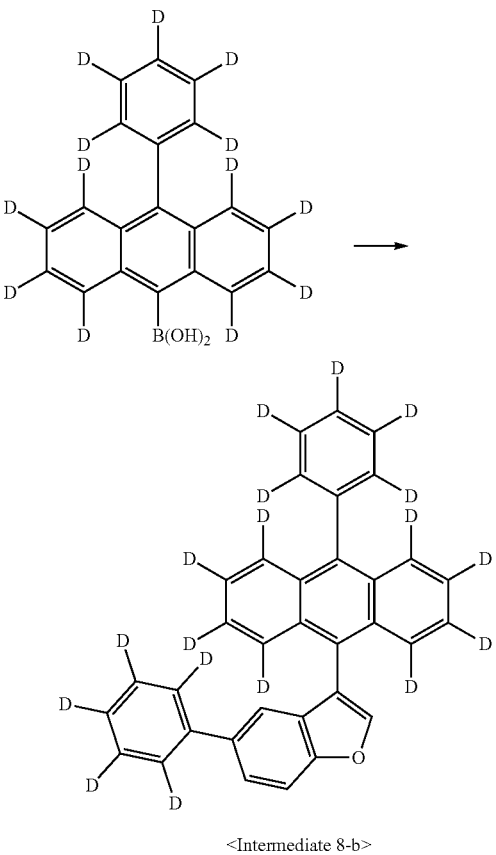

<Intermediate 8-b>

Intermediate 8-b (yield 55%) was synthesized in the same manner as in Synthesis Example 2-3, except that Intermediate 8-a was used instead of 10-phenyl-anthracene-9-boronic acid.

Synthesis Example 8-3: Synthesis of Intermediate 8-c

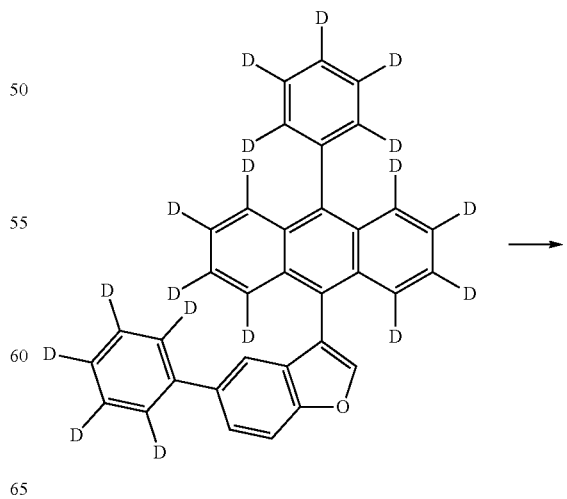

-continued

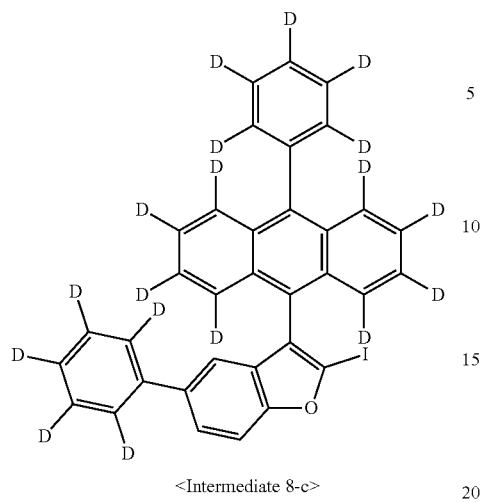

<Intermediate 8-c>

Intermediate 8-c (yield 67%) was synthesized in the same manner as in Synthesis Example 3-4, except that Intermediate 8-b was used instead of Intermediate 3-c.

Synthesis Example 8-4: Synthesis of Compound 90

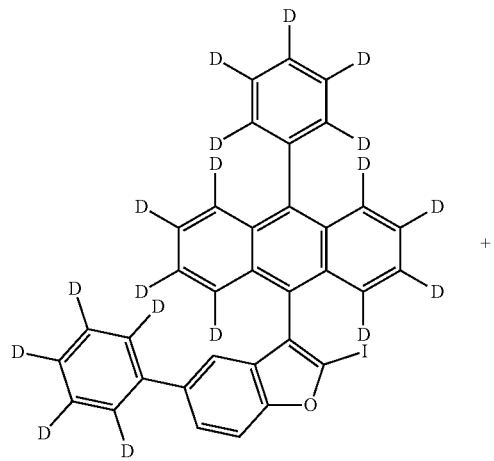

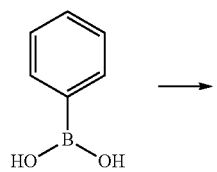

-continued

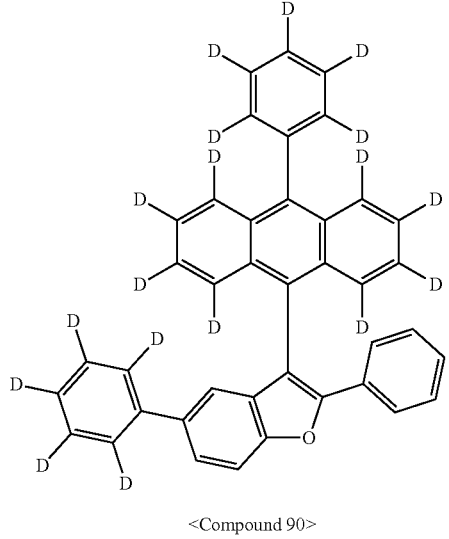

<Compound 90>

Compound 90 (yield 47%) was synthesized in the same manner as in Synthesis Example 7-3, except that Intermediate 8-c was used instead of Intermediate 7-b.

MS (MALDI-TOF): m/z 540.31 [M$^+$]

SYNTHESIS EXAMPLE 9. SYNTHESIS OF COMPOUND 91

Synthesis Example 9-1: Synthesis of Intermediate 9-a

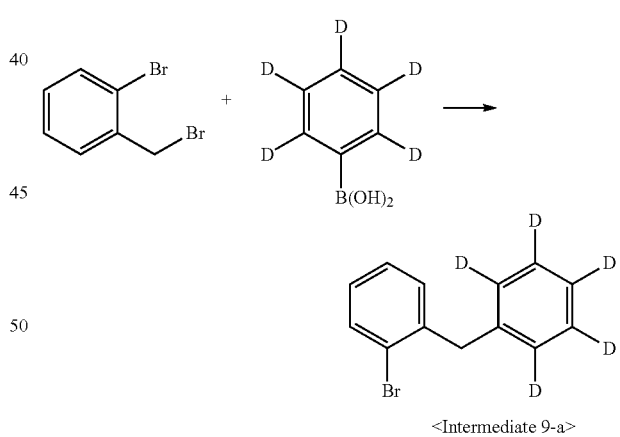

<Intermediate 9-a>

Bromobenzyl bromide (20 g, 0.08 mol), (phenyl-d5) boronic acid (10 g, 0.078 mol), sodium carbonate (10 g, 0.1 mol), and tetrakis(triphenylphosphine)palladium(0) (1.8 g, 0.002 mol) were placed in a 500 mL reactor. The mixture was heated to reflux at 50° C. After 1 h, distilled water was added to the reaction solution, followed by stirring. The resulting mixture was allowed to stand for layer separation. The organic layer was filtered, washed with toluene, and concentrated under reduced pressure. Thereafter, the concentrate was purified by column chromatography to afford Intermediate 9-a (16 g, 82%).

Synthesis Example 9-2: Synthesis of Intermediate 9-b

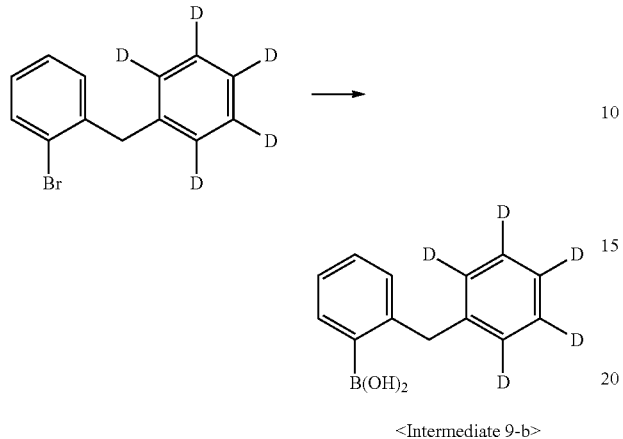

<Intermediate 9-b>

Intermediate 9-a (20 g, 0.08 mol) and 200 mL of THF were cooled to −78° C. in a 500 mL reactor and n-butyllithium (1.6 M) was added thereto. To the mixture was slowly added trimethyl borate. The temperature was gradually raised to room temperature. To the resulting mixture was added a 2 M aqueous HCl solution, followed by stirring for 20 min. The reaction mixture was allowed to stand for layer separation. The organic layer was washed with distilled water, concentrated, and recrystallized from THF and heptane to afford Intermediate 9-b (11 g, 63%).

Synthesis Example 9-3: Synthesis of Intermediate 9-c

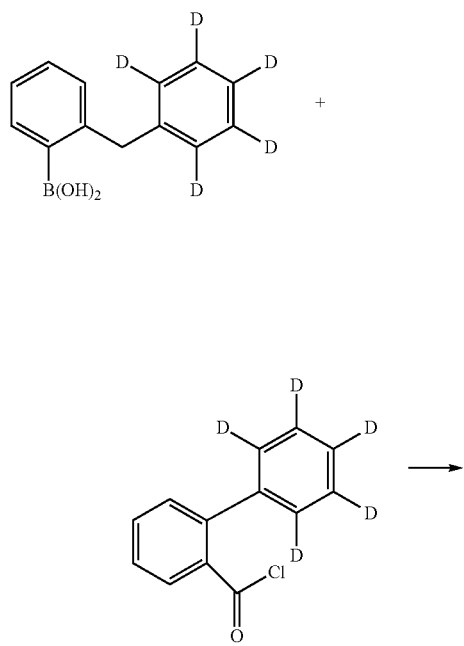

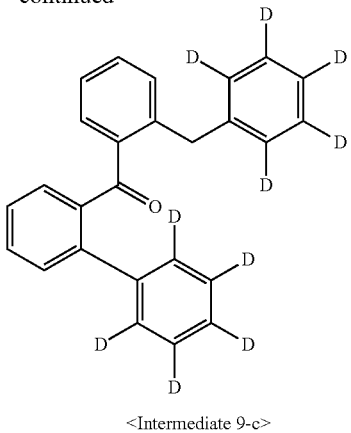

<Intermediate 9-c>

Intermediate 9-b (15 g, 0.07 mol), cesium carbonate (34 g, 0.1 mol), tetrakis(triphenylphosphine)palladium(0) (2.4 g, 0.002 mol), and 150 mL of toluene were stirred in a 500 mL reactor. After dropwise addition of 1,1'-(biphenyl-d5)-2-carbonyl chloride (20 g, 0.09 mol), the mixture was heated to reflux at 110° C. After 2 h, toluene and distilled water were added to the reaction solution, followed by stirring. The mixture was allowed to stand for layer separation. The organic layer was concentrated under reduced pressure and purified by column chromatography to afford Intermediate 9-c (14 g, 57%).

Synthesis Example 9-4: Synthesis of Intermediate 9-d

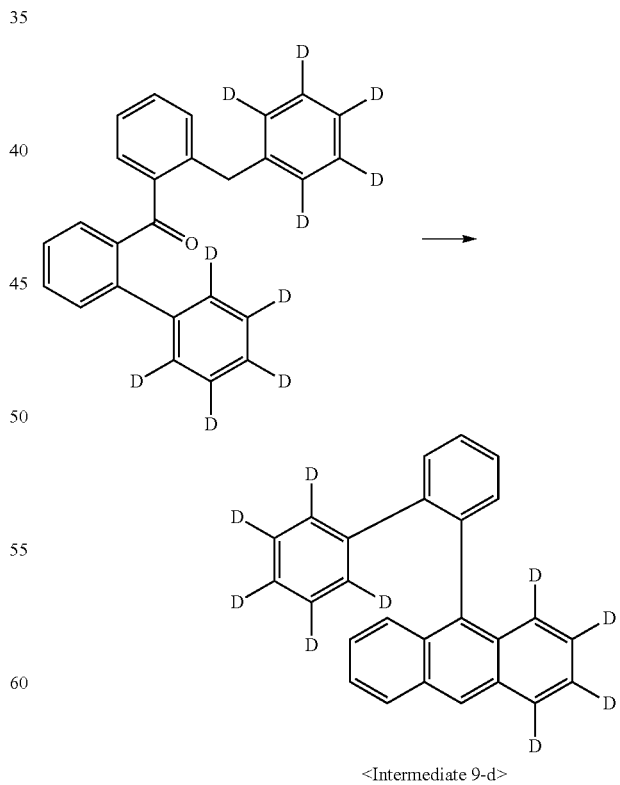

<Intermediate 9-d>

Intermediate 9-c (20 g, 0.06 mol), In(OTf)$_3$ (3.1 g, 0.006 mol), and 120 mL of dichlorobenzene were heated to reflux at 110° C. in a 500 mL reactor. After 24 h, the reaction solution was filtered through Celite at 50° C. and washed with MC. The organic layer was concentrated under reduced pressure and purified by column chromatography. Subsequent recrystallization afforded Intermediate 9-d (8 g, 43%).

Synthesis Example 9-5: Synthesis of Intermediate 9-e

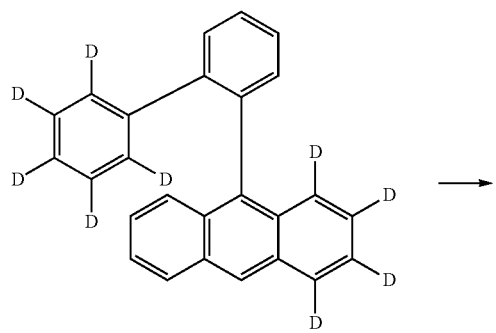

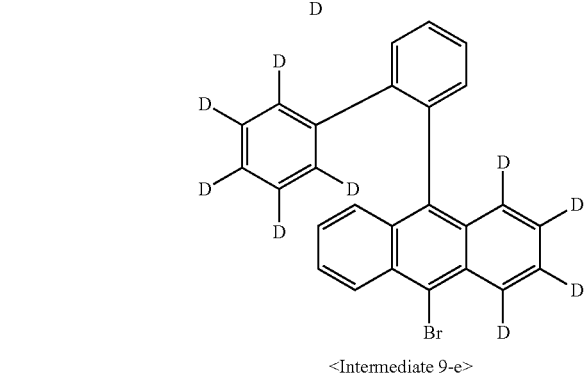

<Intermediate 9-e>

Intermediate 9-d (30 g, 0.09 mol) and 300 mL of DMF were stirred in a 500 mL reactor. Thereafter, the mixture was cooled to 0° C. and NBS (16 g, 0.09 mol) was added thereto. The temperature was raised to room temperature. After 3 h stirring, to the resulting mixture was added distilled water. Stirring was continued. The reaction mixture was filtered, washed, purified by column chromatography, and recrystallized from methanol to afford Intermediate 9-e (33 g, 89%).

Synthesis Example 9-6: Synthesis of Intermediate 9-f

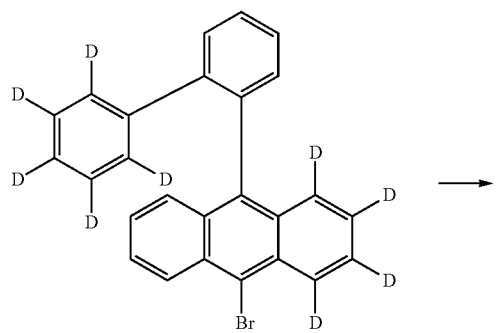

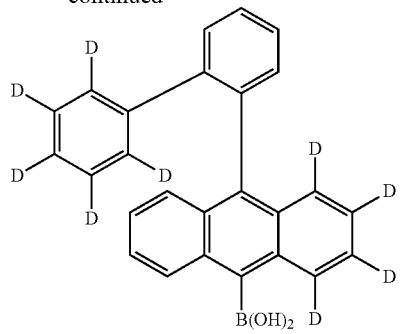

<Intermediate 9-f>

Intermediate 9-f (yield 53%) was synthesized in the same manner as in Synthesis Example 1-4, except that Intermediate 9-e was used instead of Intermediate 1-c.

Synthesis Example 9-7: Synthesis of Compound 91

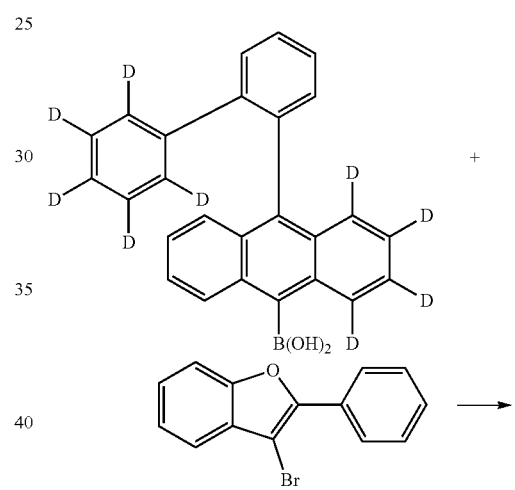

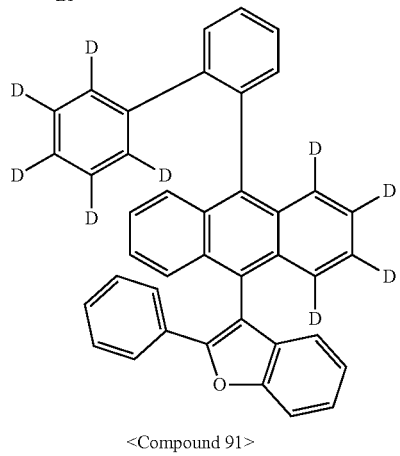

<Compound 91>

Compound 91 (yield 52%) was synthesized in the same manner as in Synthesis Example 1-5, except that Intermediate 9-f and 3-bromo-2-phenylbenzofuran were used instead of Intermediate 1-d and (4-bromophenyl)boronic acid, respectively.

MS (MALDI-TOF): m/z 531.25 [M$^+$]

SYNTHESIS EXAMPLE 10. SYNTHESIS OF COMPOUND 92

Synthesis Example 10-1: Synthesis of Intermediate 10-a

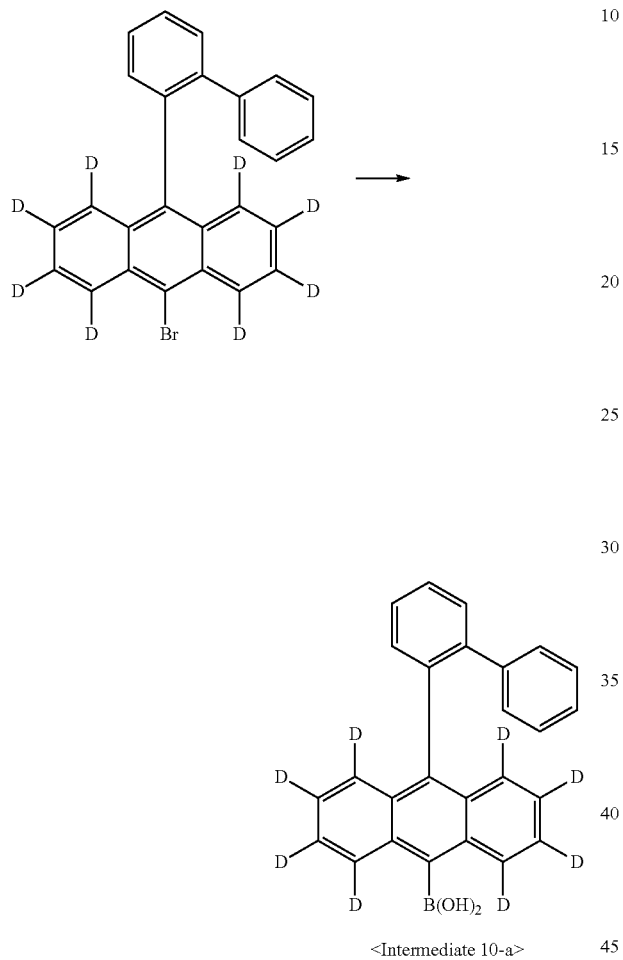

<Intermediate 10-a>

Intermediate 10-a (yield 52%) was synthesized in the same manner as in Synthesis Example 2-3, except that (anthracene-d8)-9-bromo-10-(1,1-biphenyl) was used instead of Intermediate 1-c.

Synthesis Example 10-2: Synthesis of Intermediate 10-b

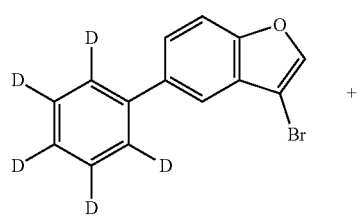

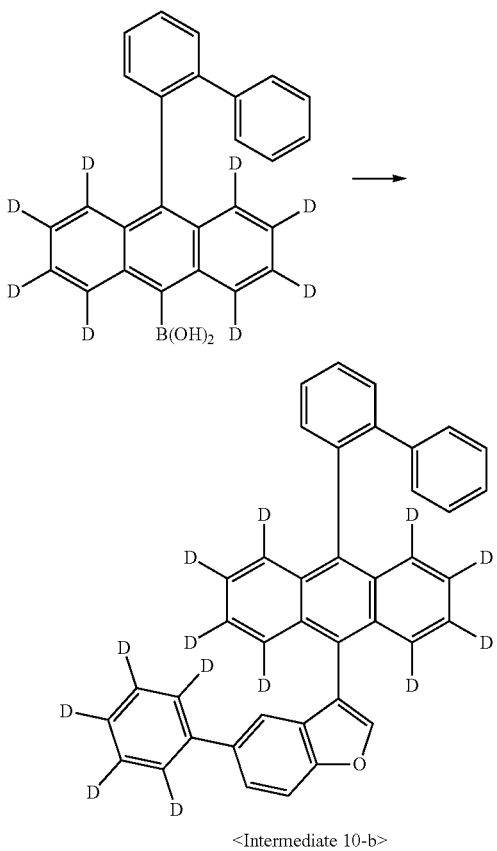

<Intermediate 10-b>

Intermediate 10-b (yield 54%) was synthesized in the same manner as in Synthesis Example 2-3, except that Intermediate 10-a was used instead of 10-phenyl-anthracene-9-boronic acid.

Synthesis Example 10-3: Synthesis of Intermediate 10-c

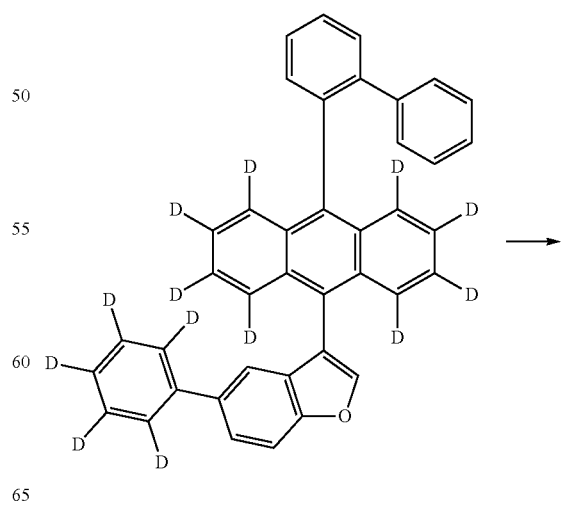

107
-continued

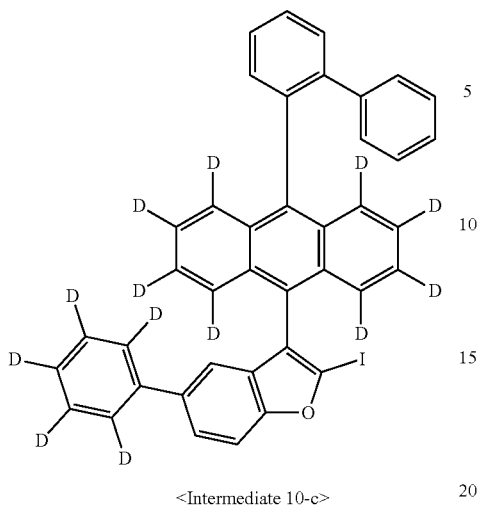

<Intermediate 10-c>

Intermediate 10-c (yield 64%) was synthesized in the same manner as in Synthesis Example 3-4, except that Intermediate 10-b was used instead of Intermediate 3-c.

Synthesis Example 10-4: Synthesis of Compound 92

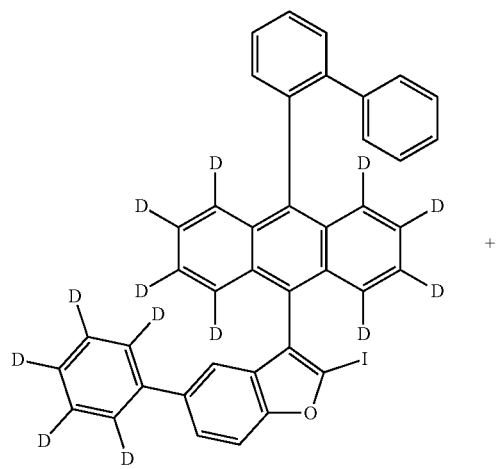

+

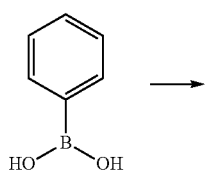

108
-continued

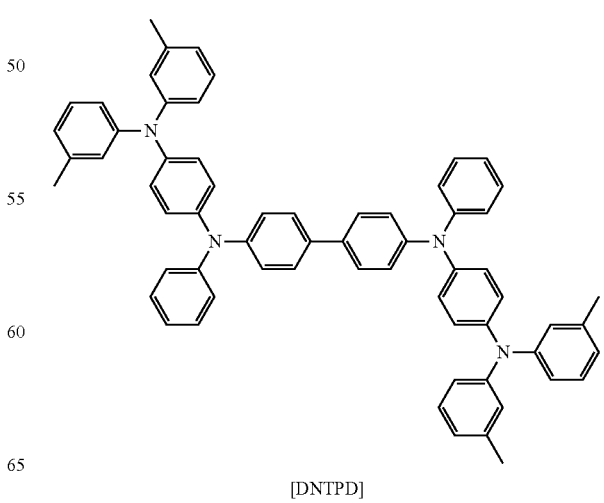

<Compound 92>

Compound 92 (yield 45%) was synthesized in the same manner as in Synthesis Example 7-3, except that Intermediate 8-c was used instead of Intermediate 7-b.
MS (MALDI-TOF): m/z 611.31 [M$^+$]

Examples 1 to 10: Fabrication of Organic Electroluminescent Devices

ITO glass was patterned to have a light emitting area of 2 mm×2 mm, followed by cleaning. After the cleaned ITO glass was mounted in a vacuum chamber, the base pressure was adjusted to $1\times10^{-7}$ torr. DNTPD (700 Å) and α-NPD (300 Å) were deposited in this order on the ITO glass. A mixture of the inventive host compound and the dopant compound shown in Table 1 was used to form a 300 Å thick light emitting layer. Thereafter, the compound of Formula E-1 and the compound of Formula E-2 were used in a ratio of 1:1 to form a 300 Å thick electron transport layer on the light emitting layer. The compound of Formula E-2 was used to form a 10 Å thick electron injecting layer on the electron transport layer. Al was deposited on the electron injecting layer to form a 1000 Å thick Al electrode, completing the fabrication of an organic electroluminescent device. The luminescent properties of the organic electroluminescent device were measured at 10 mA/cm$^2$.

[DNTPD]

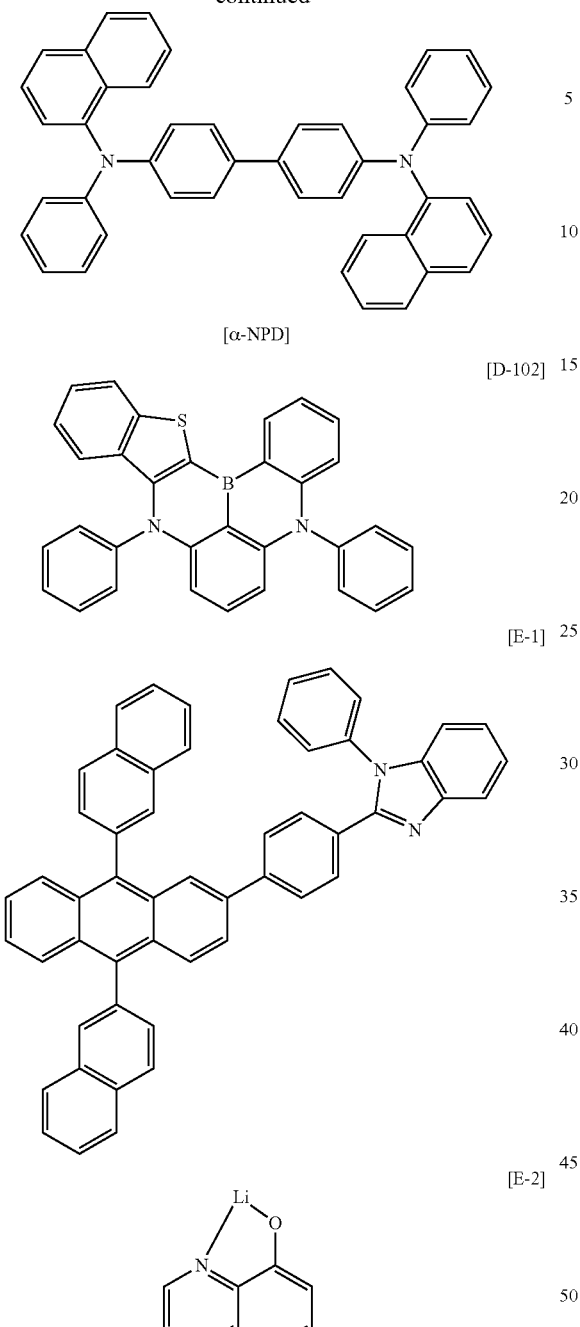
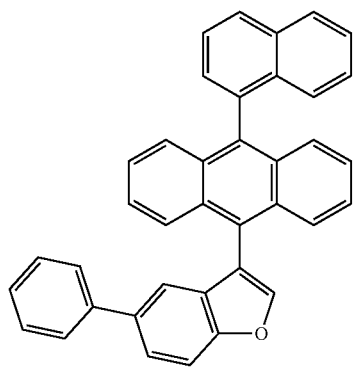
[BH1]
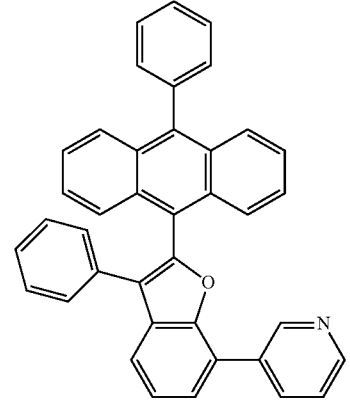
[BH2]
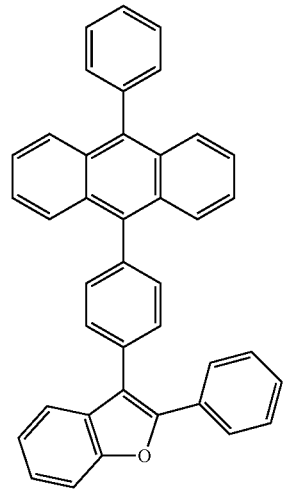
[BH3]
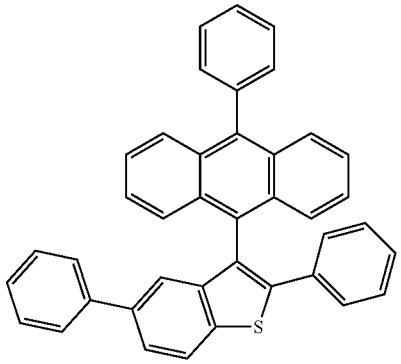
[BH4]
Comparative Examples 1 to 6
Organic electroluminescent devices were fabricated in the same manner as in Examples 1-10, except that BH1, BH2, BH3, BH4, BH5 or BH6 was used instead of the host compound. The luminescent properties of the organic electroluminescent devices were measured at 10 mA/cm². The structures of BH1, BH2, BH3, BH4, BH5, and BH6 are as follow:

-continued

[BH5]

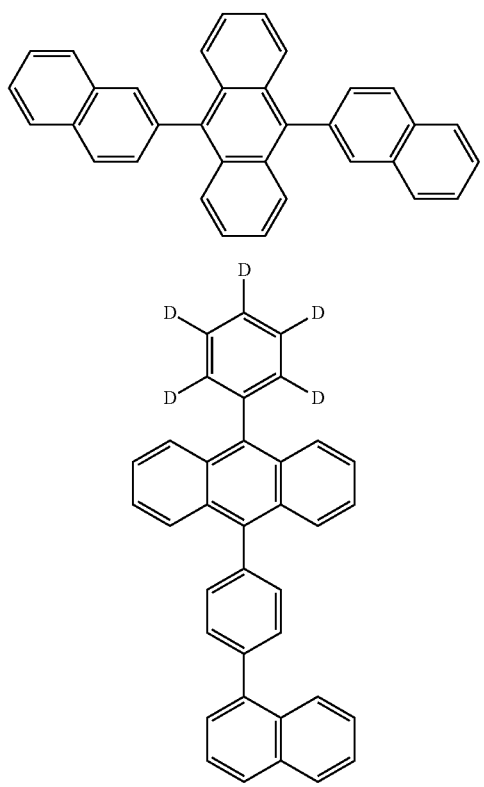

[BH6]

TABLE 1

| Example No. | Host | Dopant | Current density (mA/cm²) | Voltage (V) | Lifetime (T97, hr) |
|---|---|---|---|---|---|
| Example 1 | 14 | D-102 | 10 | 3.5 | 73 |
| Example 2 | 43 | D-102 | 10 | 3.5 | 110 |
| Example 3 | 56 | D-102 | 10 | 3.4 | 93 |
| Example 4 | 58 | D-102 | 10 | 3.3 | 86 |
| Example 5 | 61 | D-102 | 10 | 3.3 | 128 |
| Example 6 | 66 | D-102 | 10 | 3.4 | 113 |
| Example 7 | 89 | D-102 | 10 | 3.3 | 120 |
| Example 8 | 90 | D-102 | 10 | 3.4 | 147 |
| Example 9 | 91 | D-102 | 10 | 3.5 | 127 |
| Example 10 | 92 | D-102 | 10 | 3.4 | 138 |
| Comparative Example 1 | BH1 | D-102 | 10 | 3.6 | 55 |
| Comparative Example 2 | BH2 | D-102 | 10 | 3.4 | 42 |
| Comparative Example 3 | BH3 | D-102 | 10 | 3.5 | 50 |
| Comparative Example 4 | BH4 | D-102 | 10 | 3.6 | 34 |
| Comparative Example 5 | BH5 | D-102 | 10 | 3.9 | 35 |
| Comparative Example 6 | BH6 | D-102 | 10 | 4.0 | 47 |

As can be seen from the results in Table 1, the organic electroluminescent devices of Examples 1-10, each of which employed the inventive compound as a host compound for the light emitting layer, showed significantly improved life characteristics (including long lifetimes) and low-voltage characteristics compared to the devices of Comparative Examples 1-6, which employed BH1, BH2, BH3, BH4, BH5, and BH6, respectively, whose structures are different from the specific structures of the host compounds employed in the organic electroluminescent devices of Examples 1-10.

What is claimed is:

1. An anthracene derivative selected from the following compounds 1-4, 6-19, 21-31, 33-39, 41, 42, 44-52, 57-60, and 62-104:

1

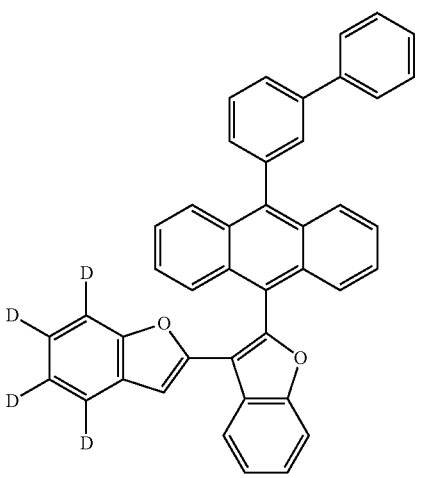

2

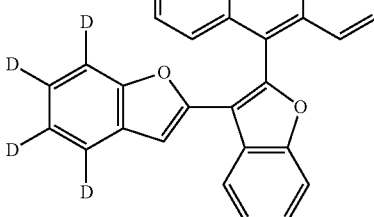

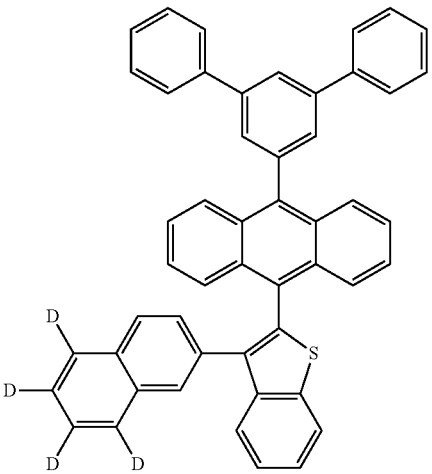

3

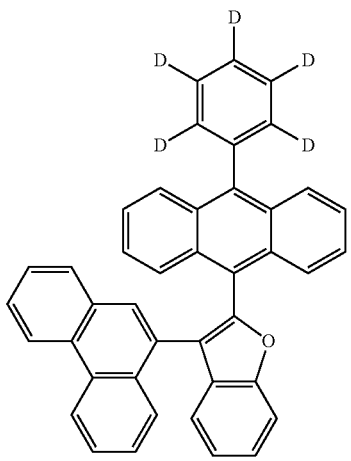

4
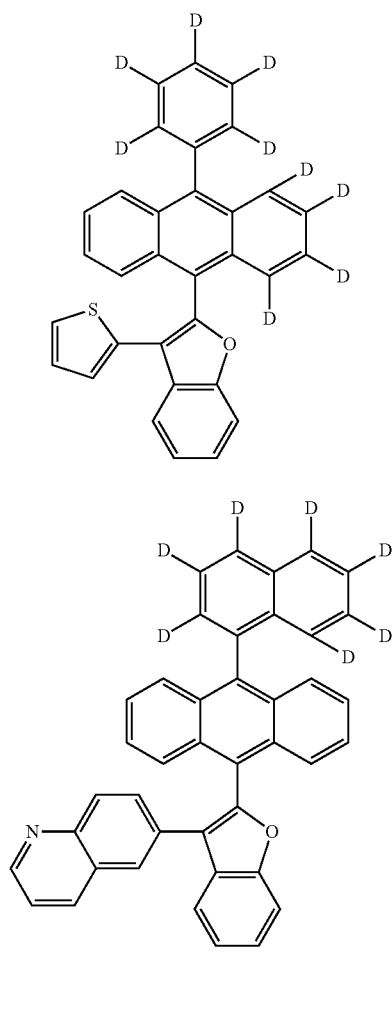
5
6
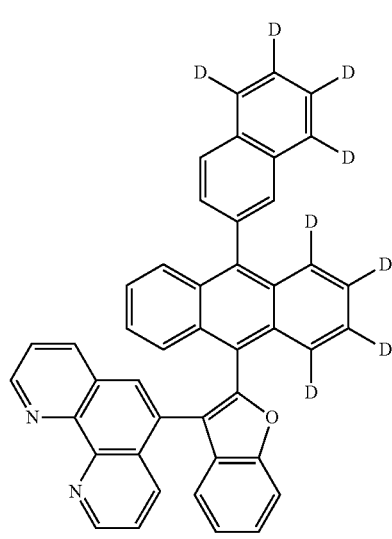
7
8
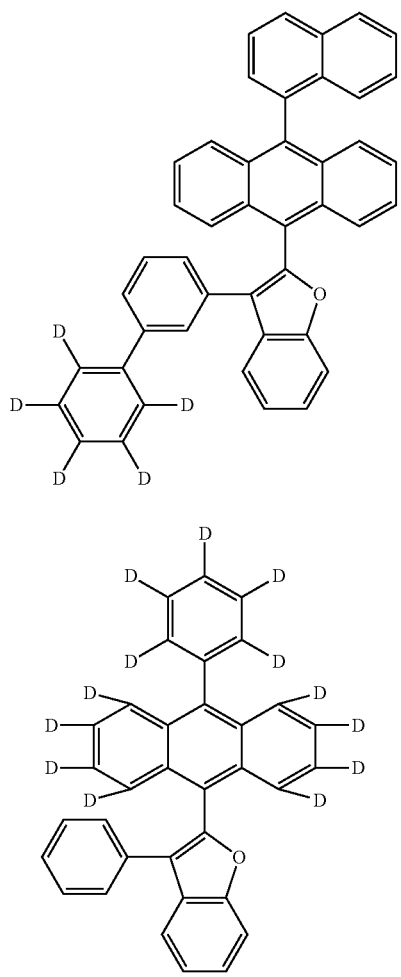
9
10
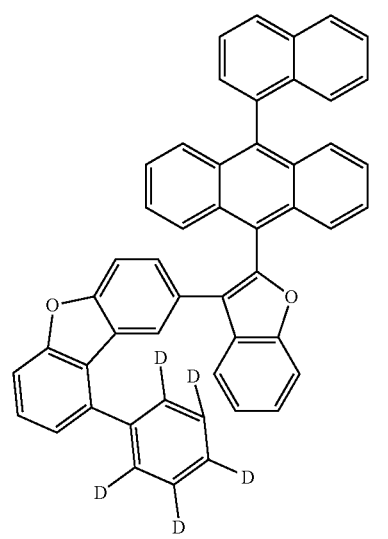

11
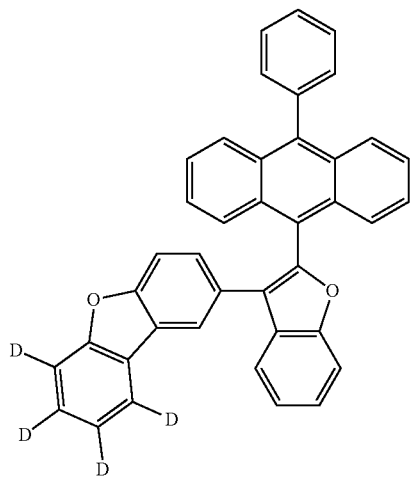
12
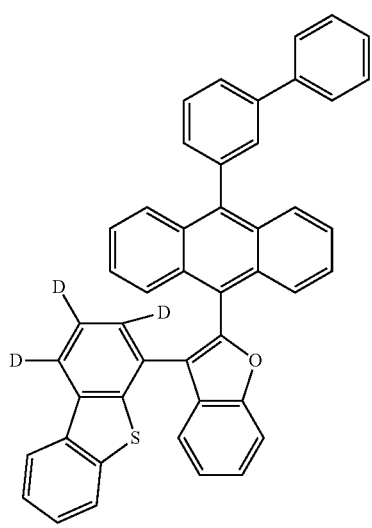
13
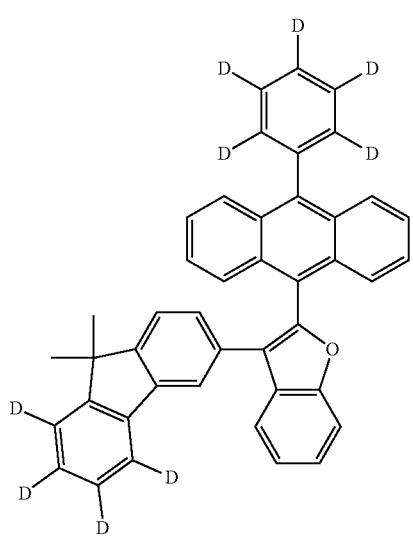
14
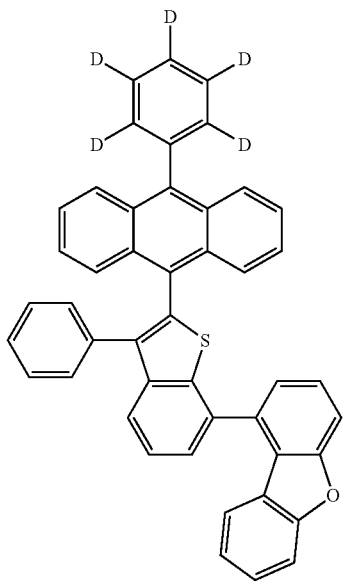
15
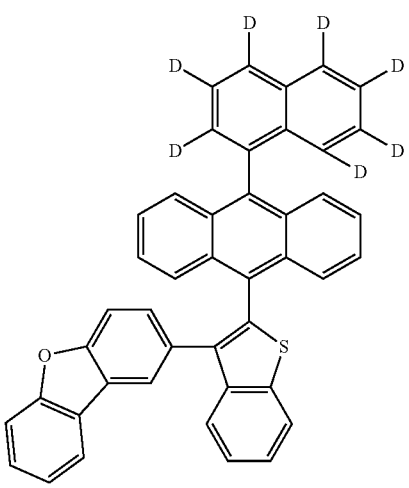
16
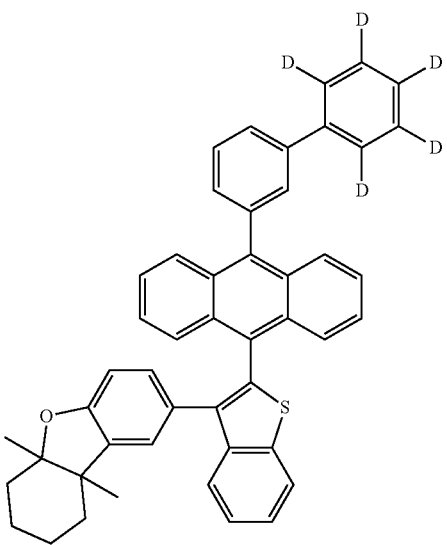

17
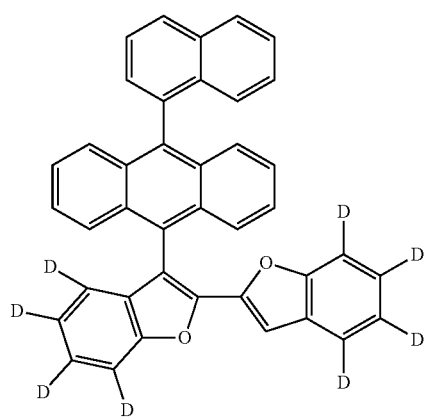
18
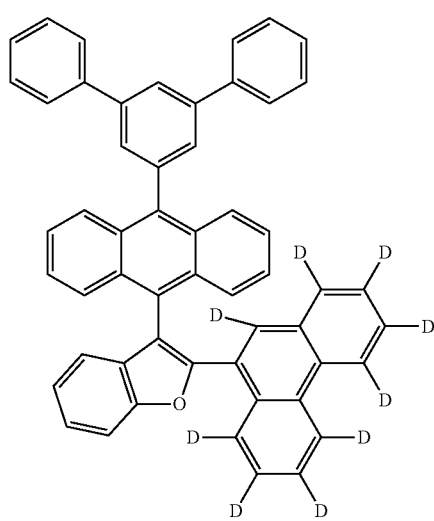
19
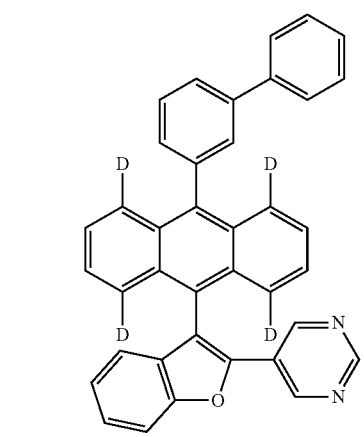
21
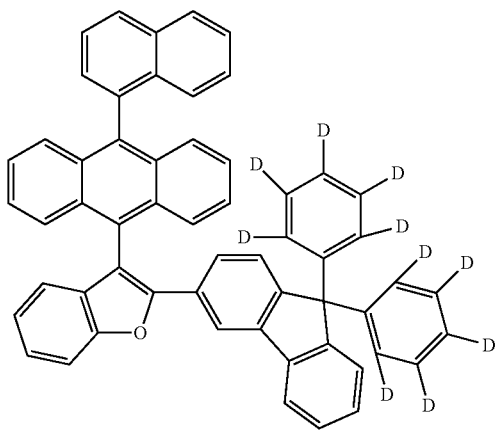
22
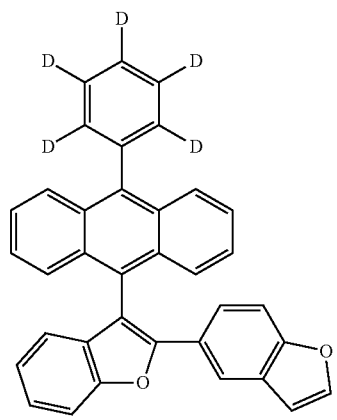
23
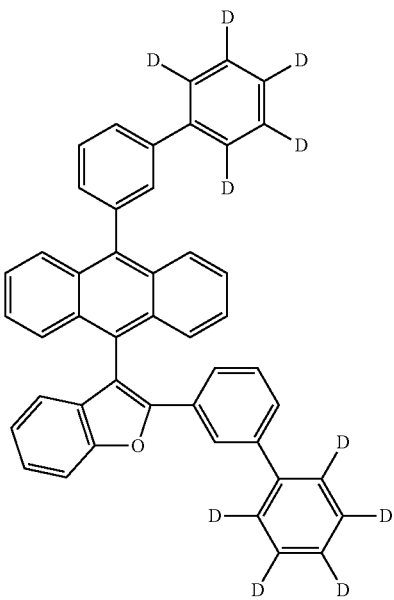

24
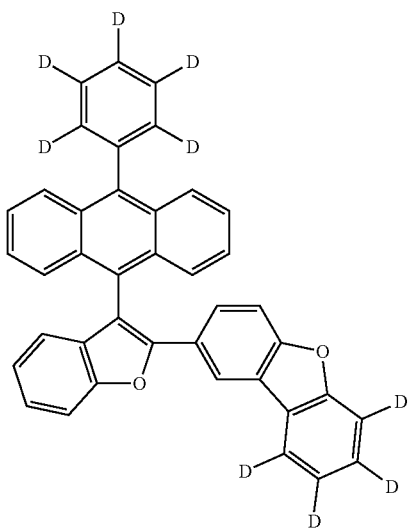
25
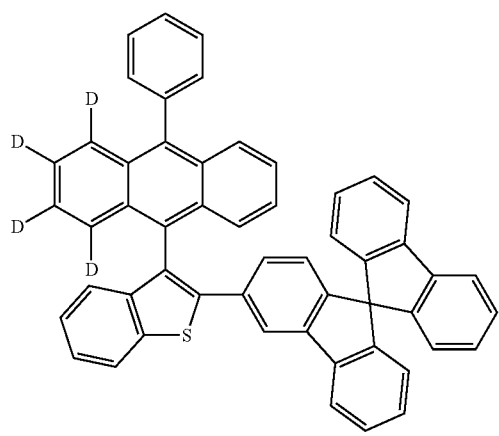
26
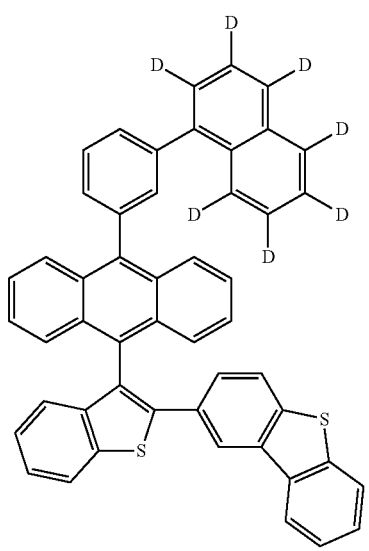
27
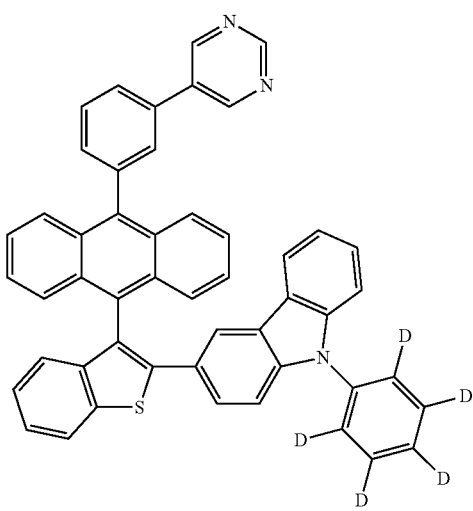
28
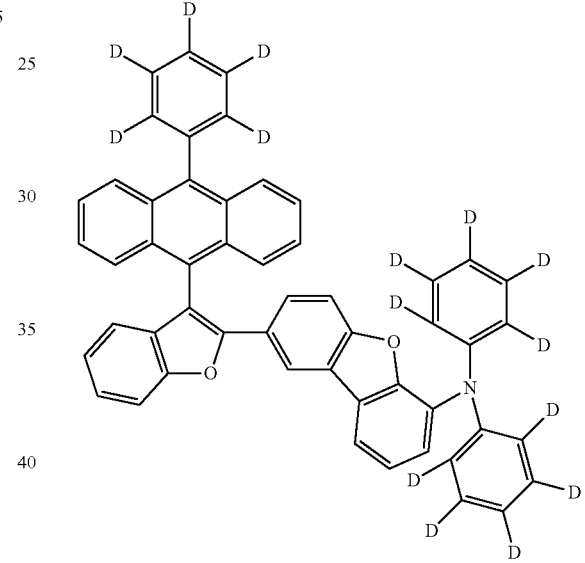
29
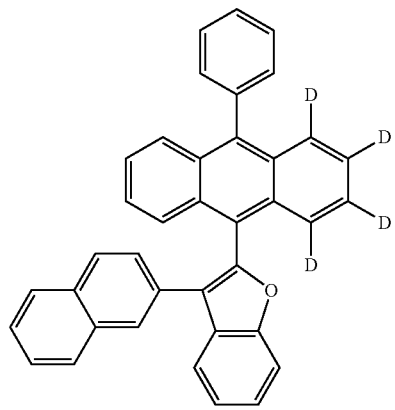

30
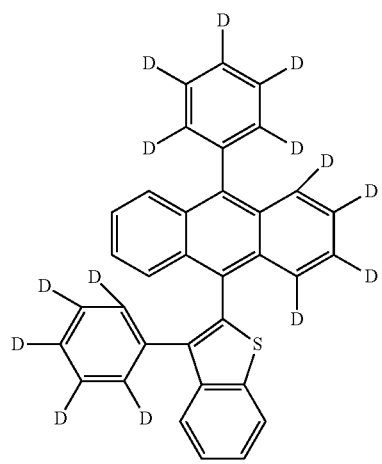
31
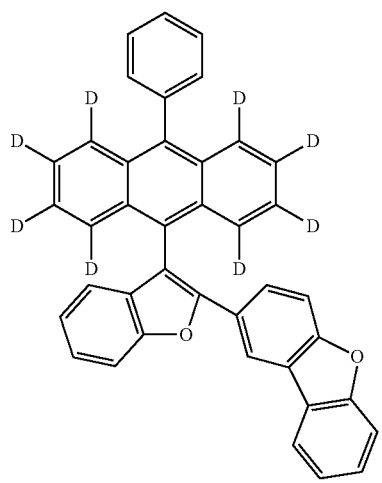
33
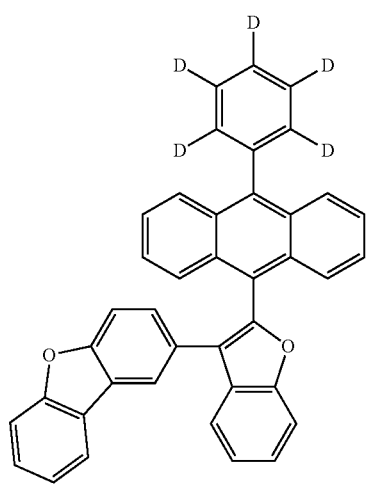
34
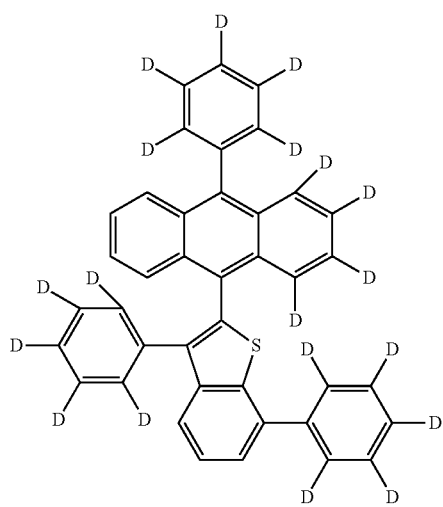
35
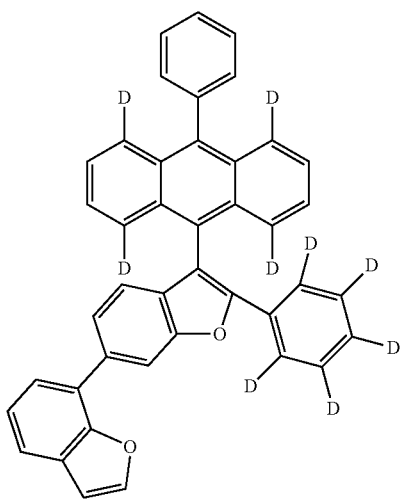
36
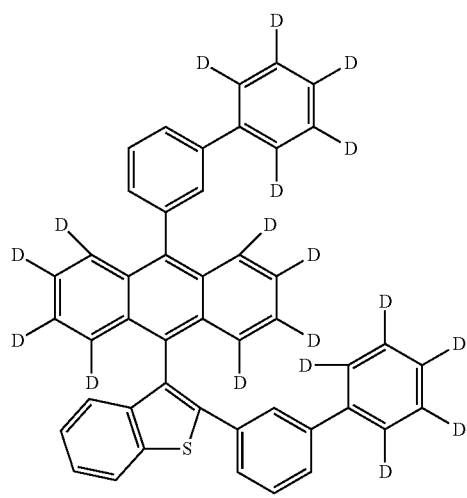

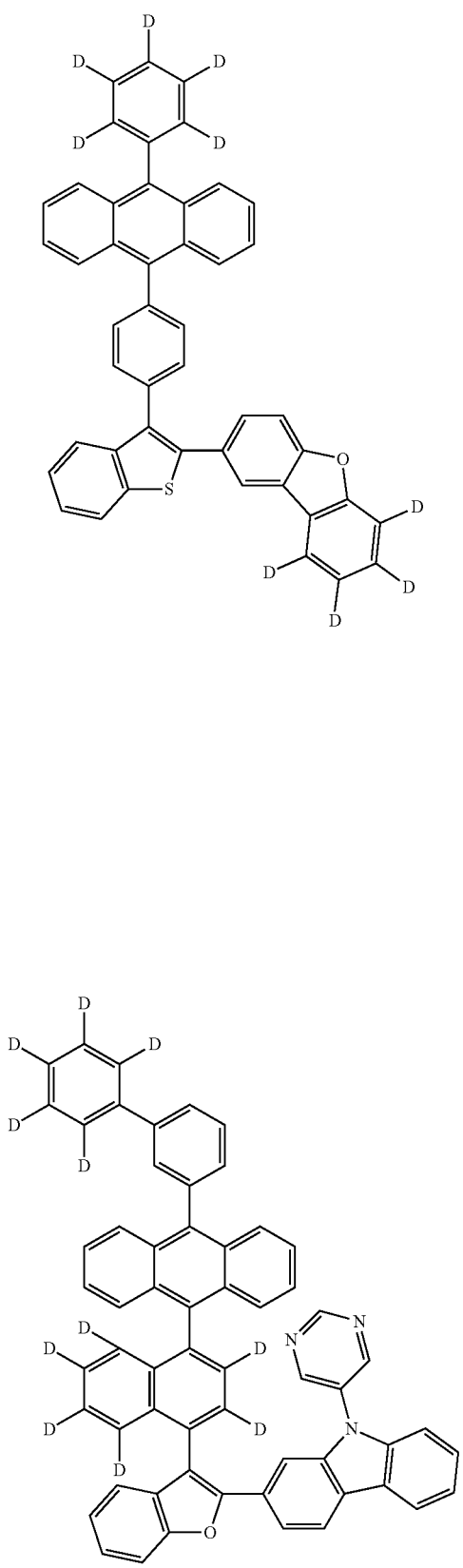
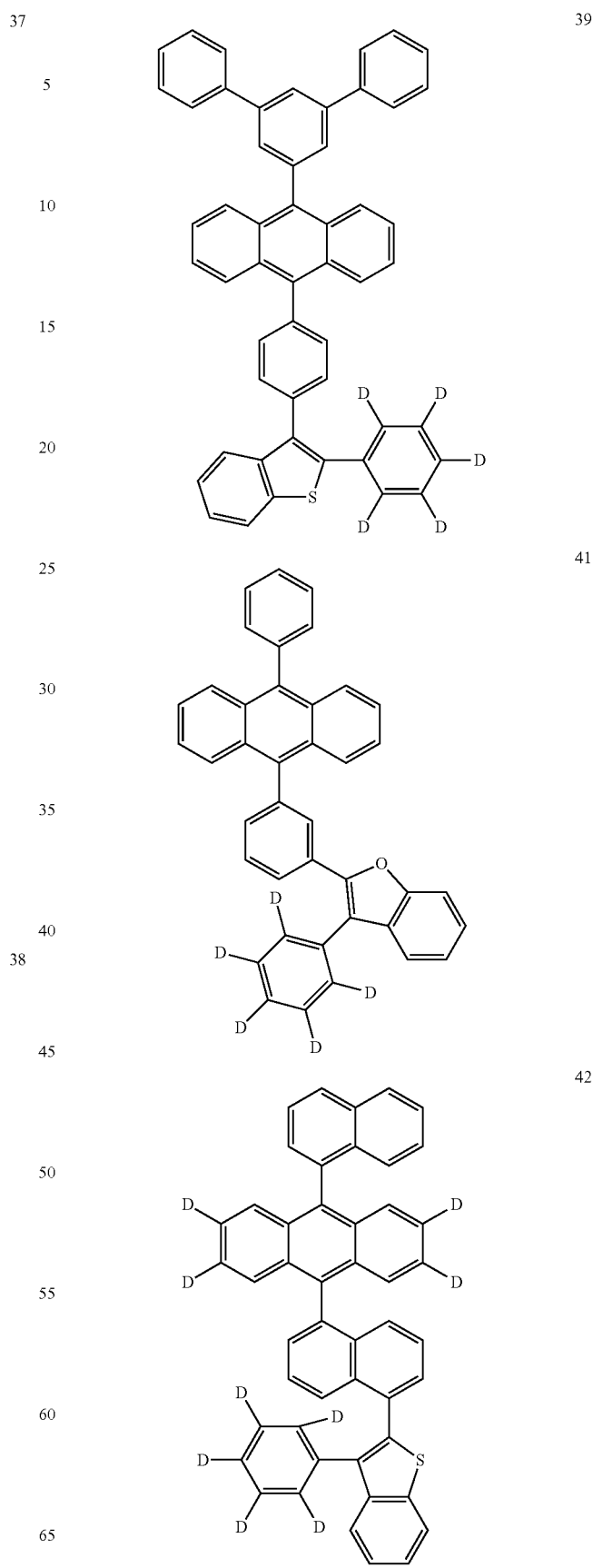

125
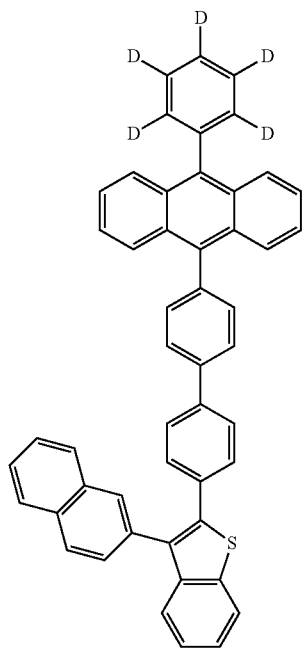
44
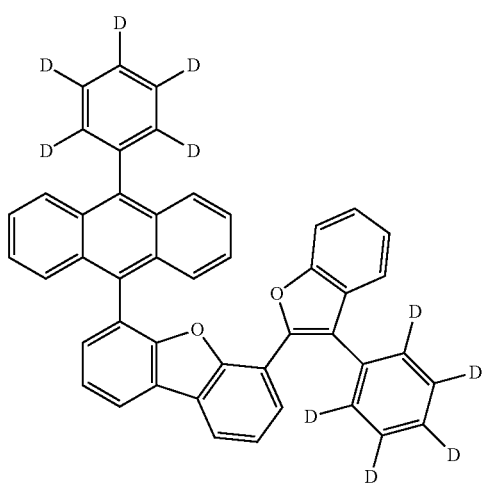
126
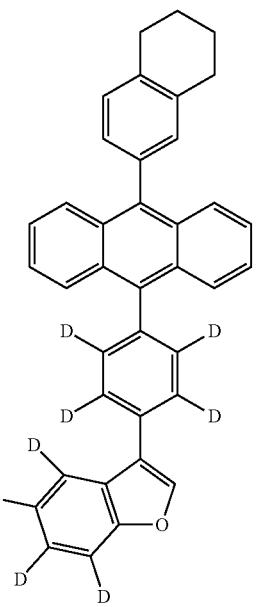
47
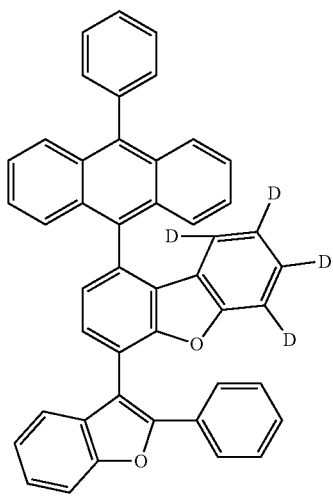

127
-continued
48
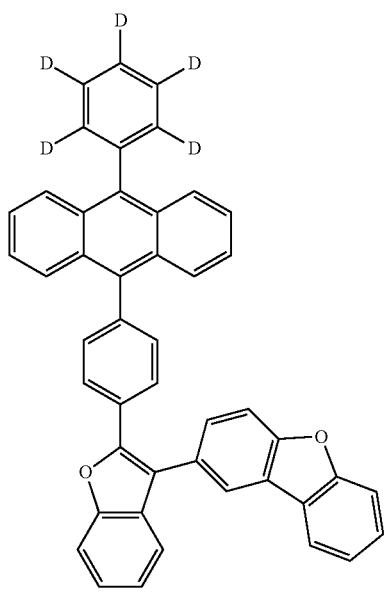
49
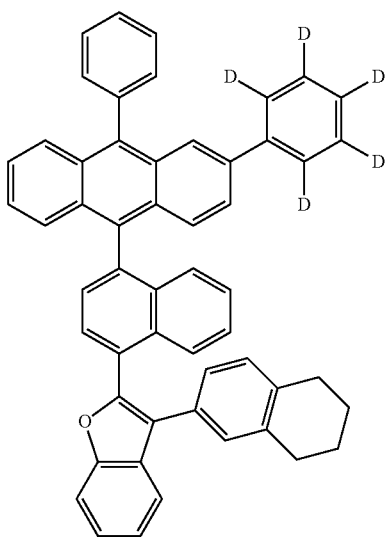
128
-continued
50
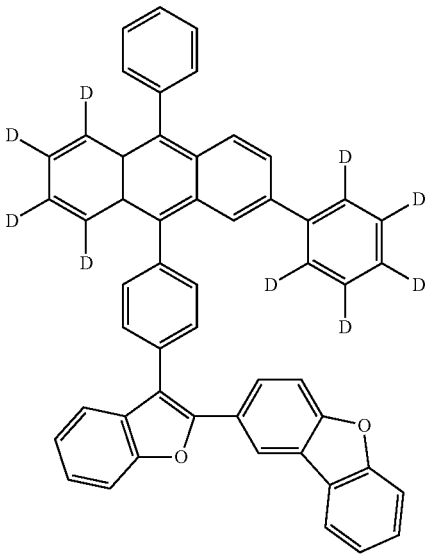
51
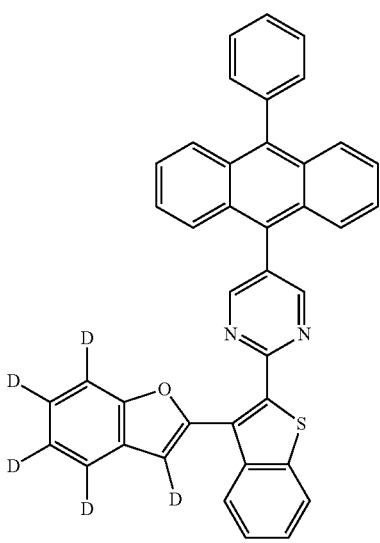

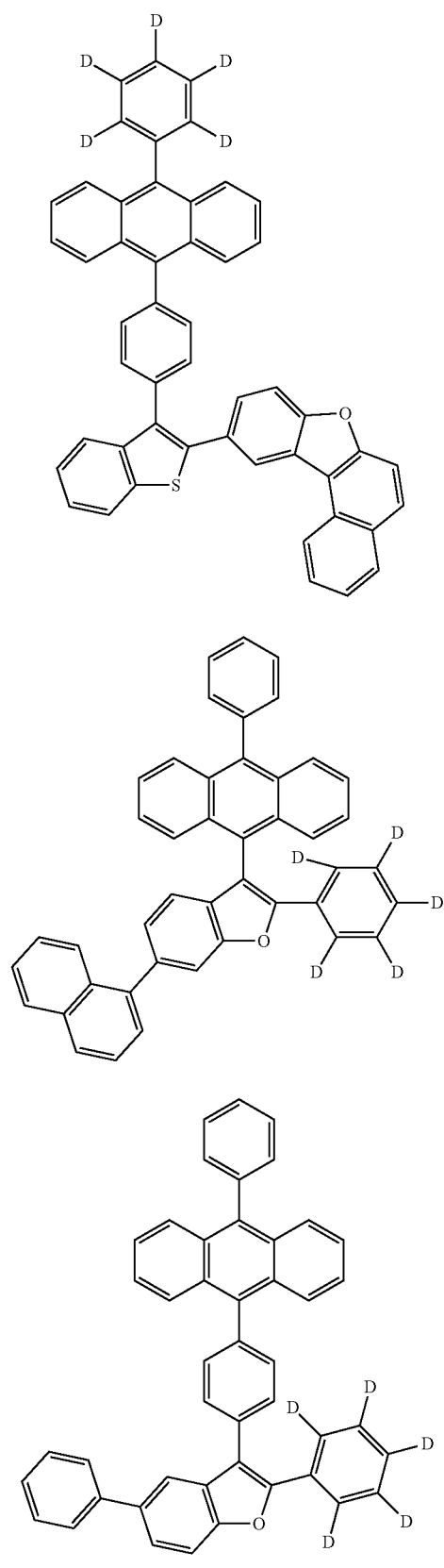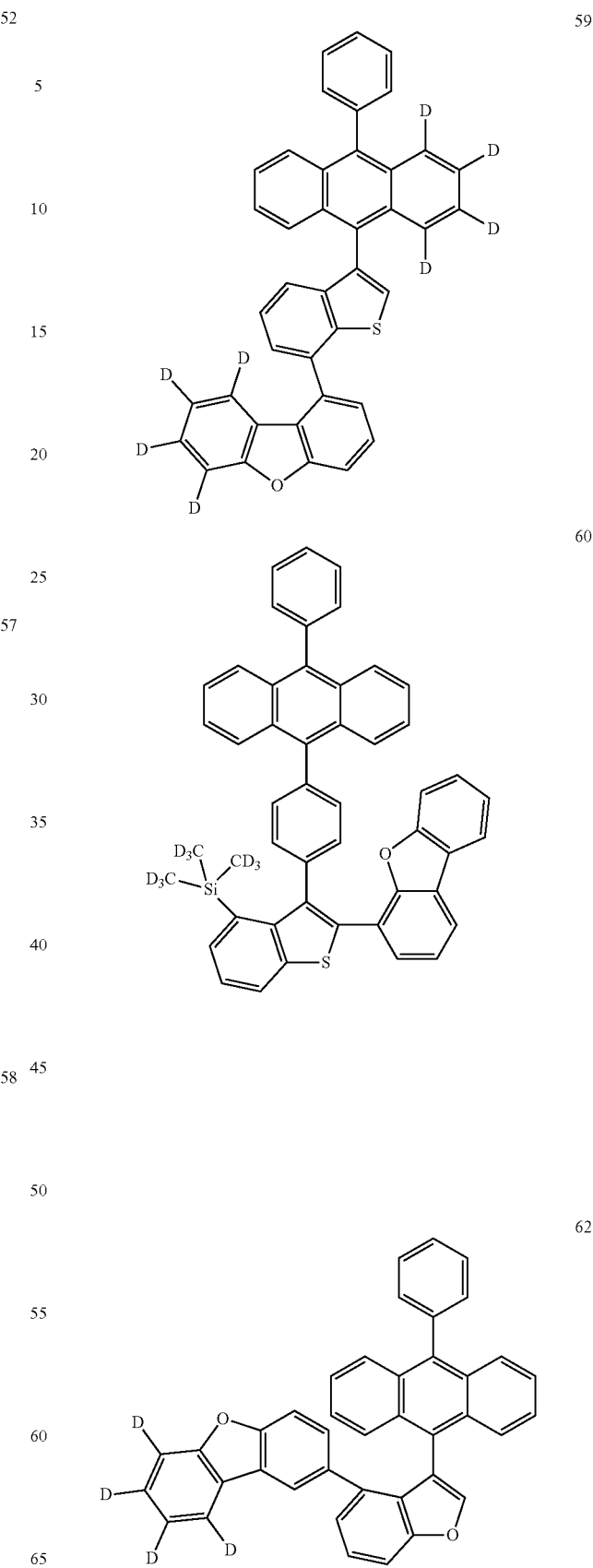

131
-continued
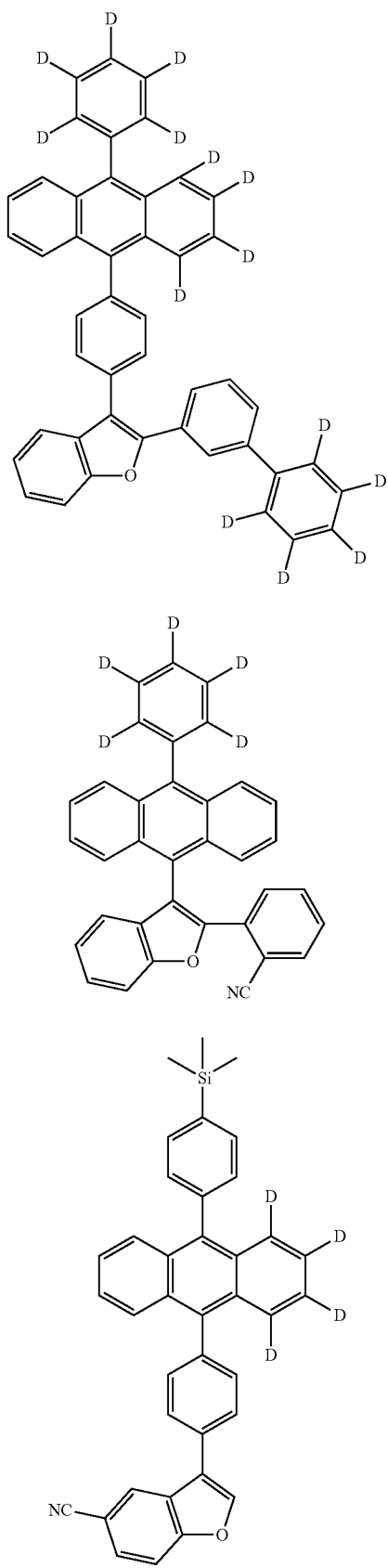
132
-continued
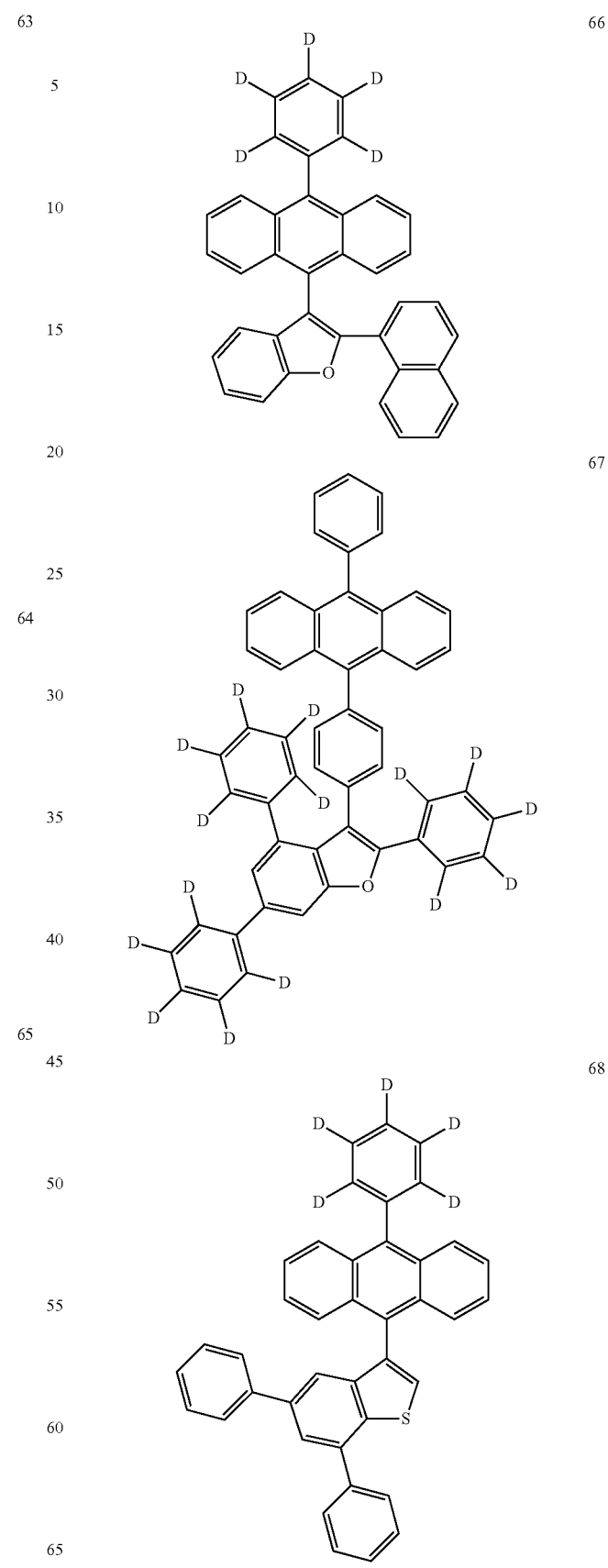

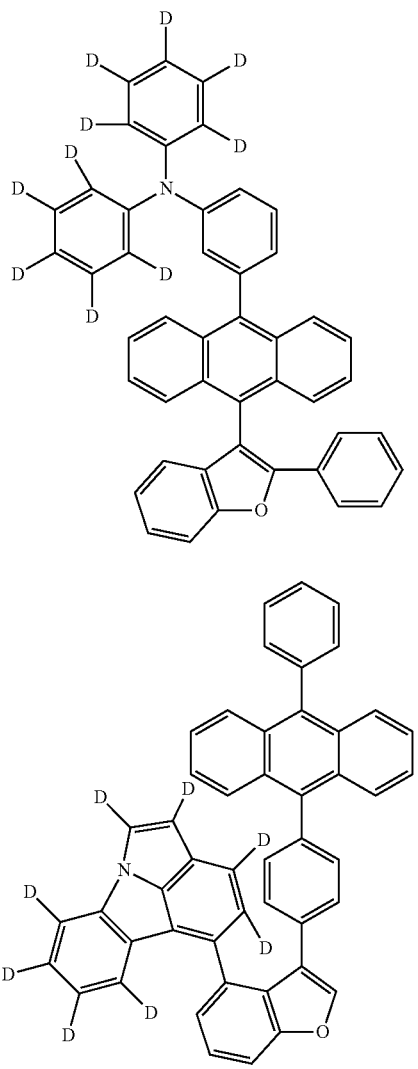
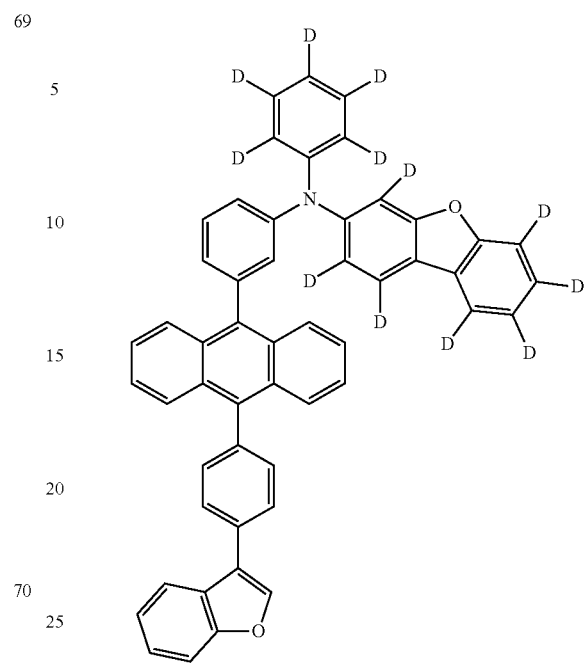
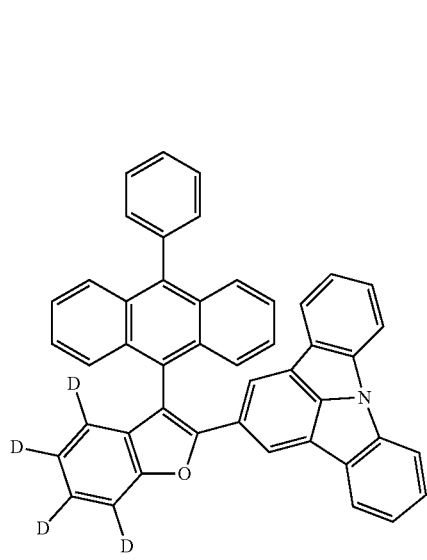
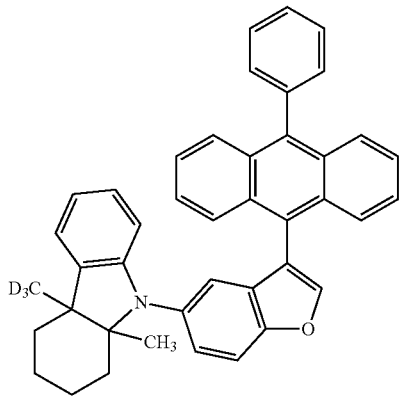

135
-continued
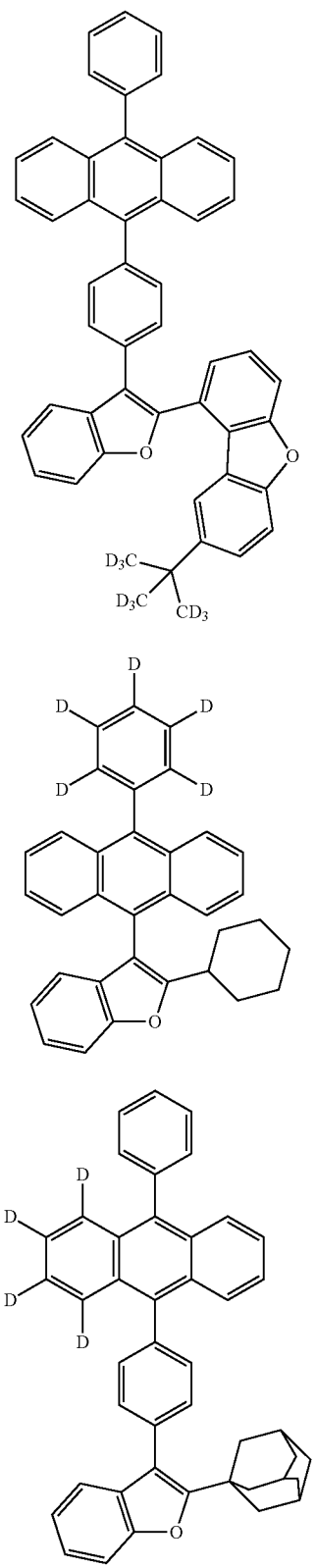
74
75
76
136
-continued
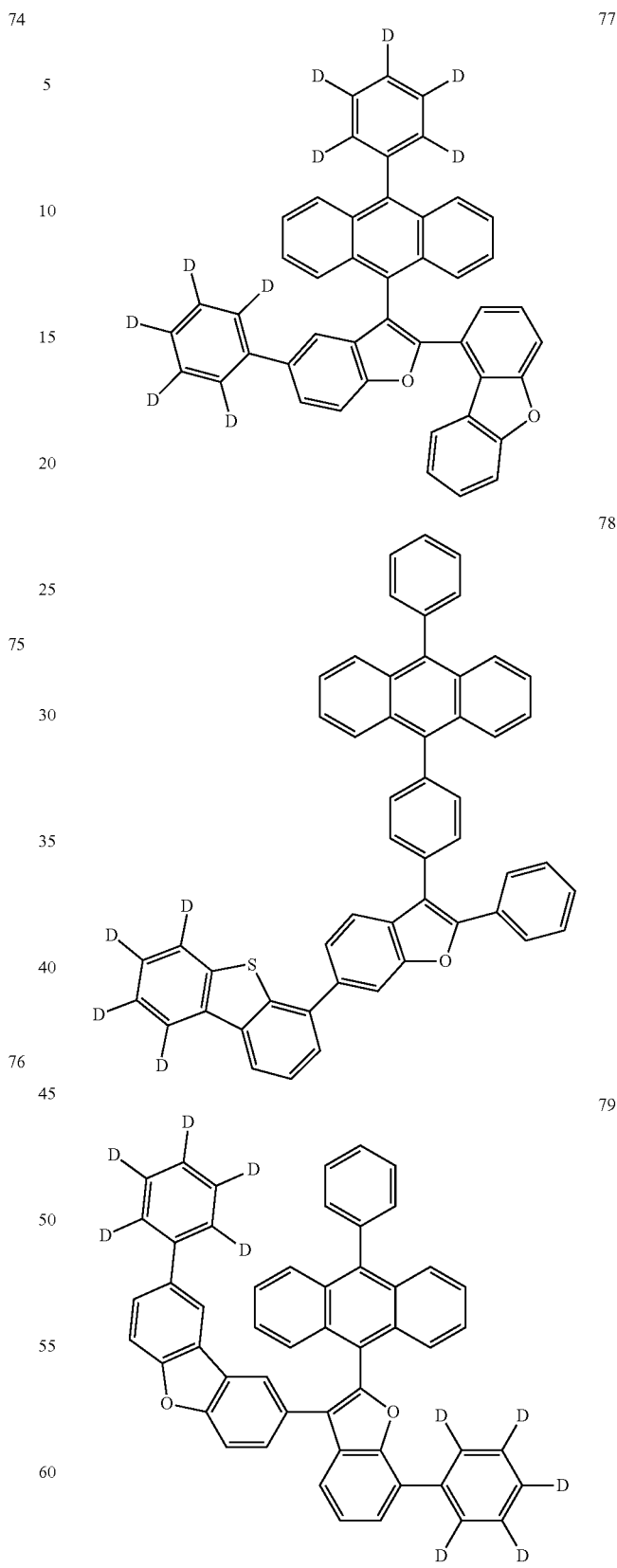
77
78
79

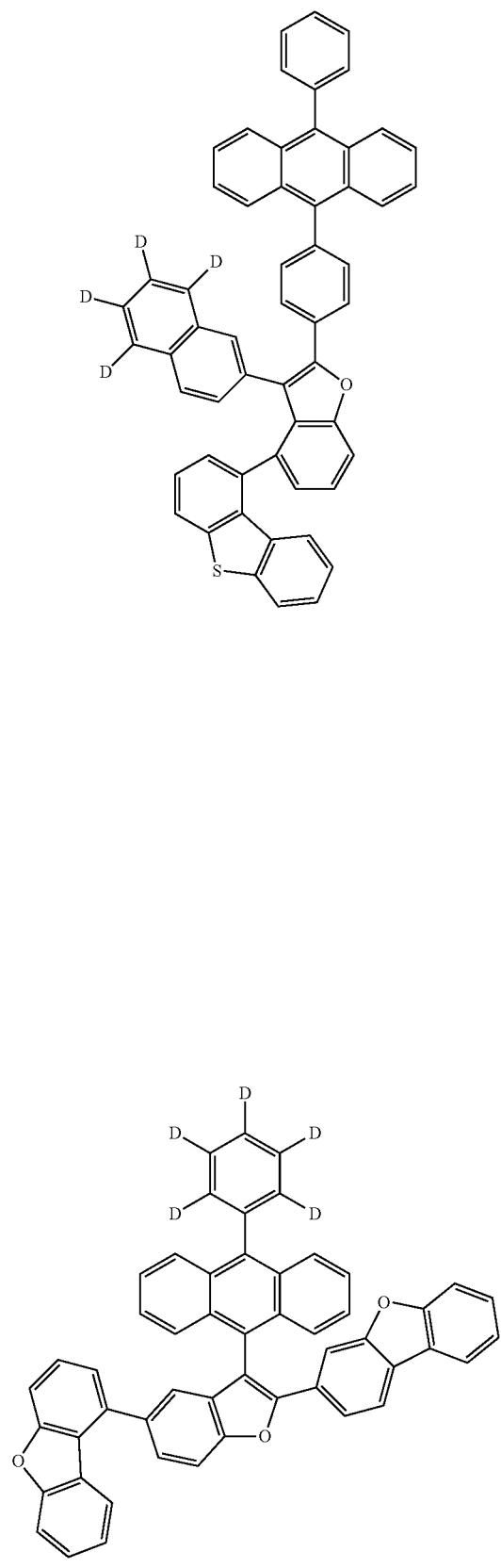
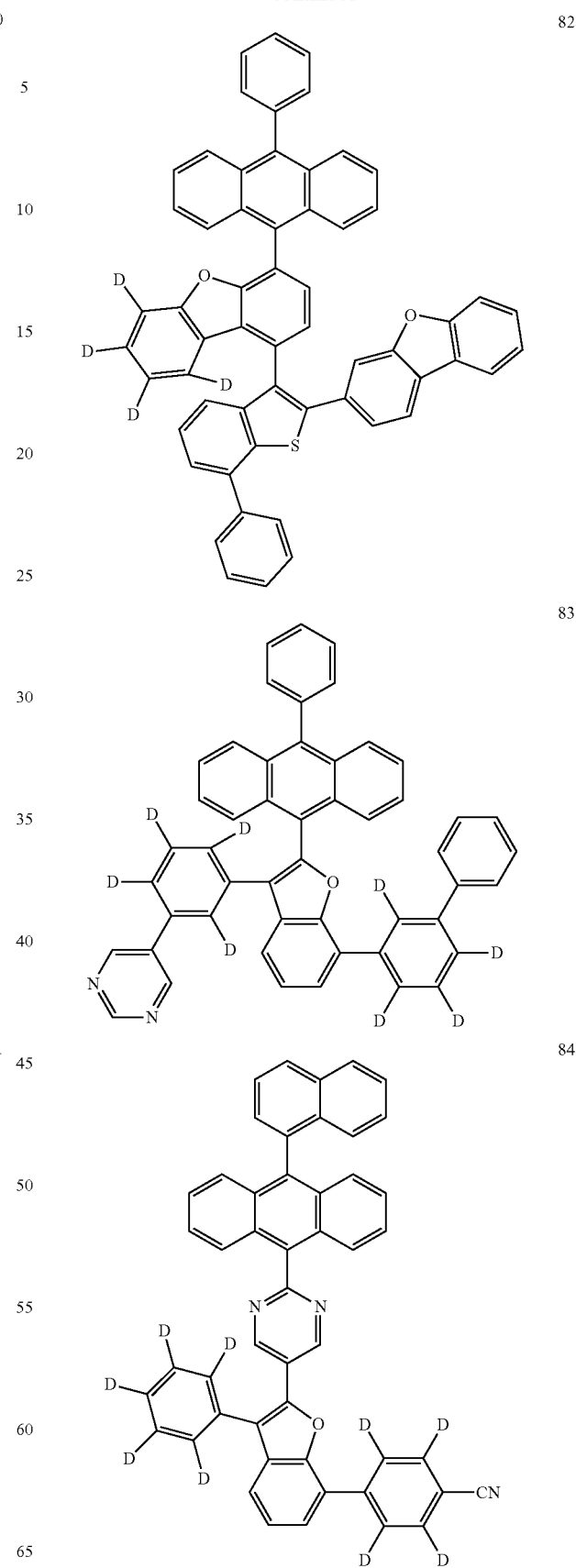

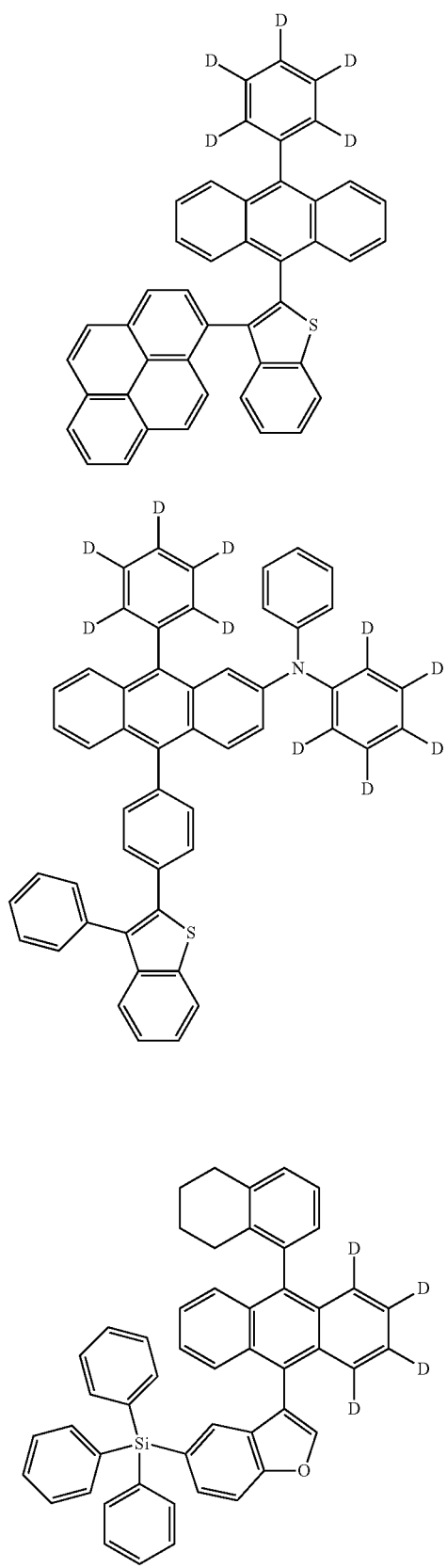
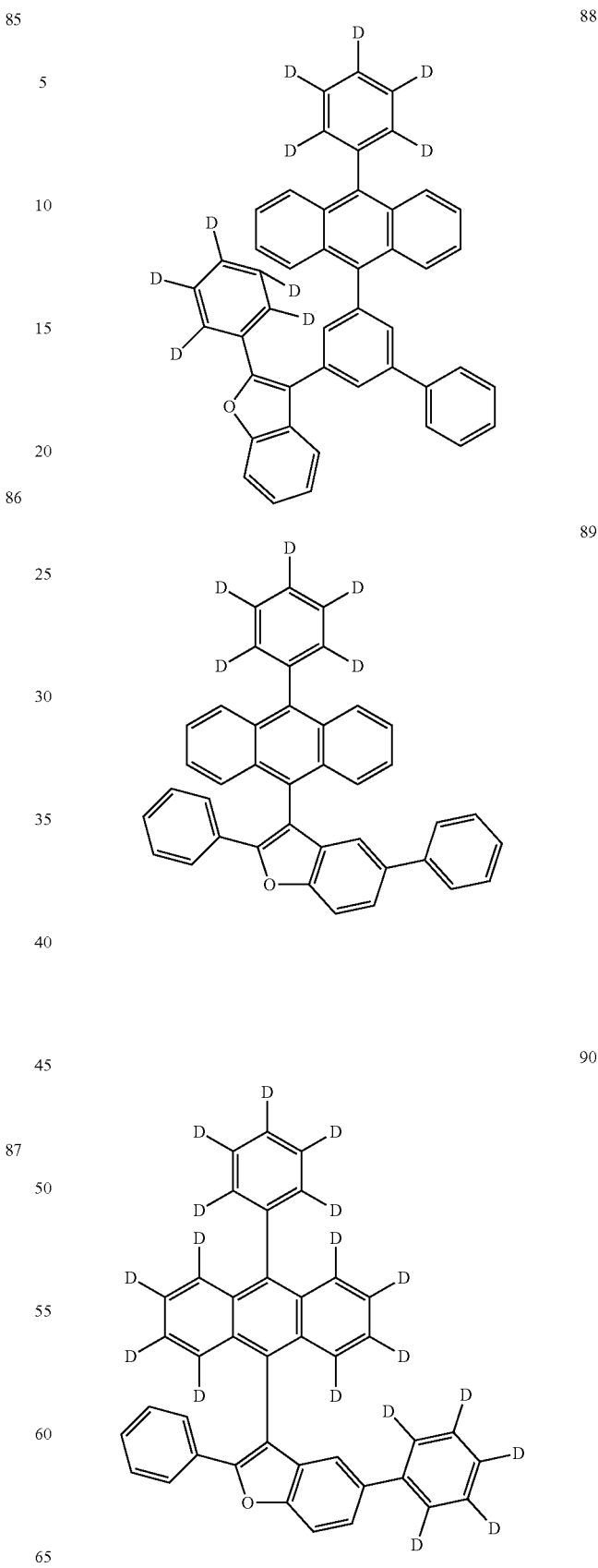

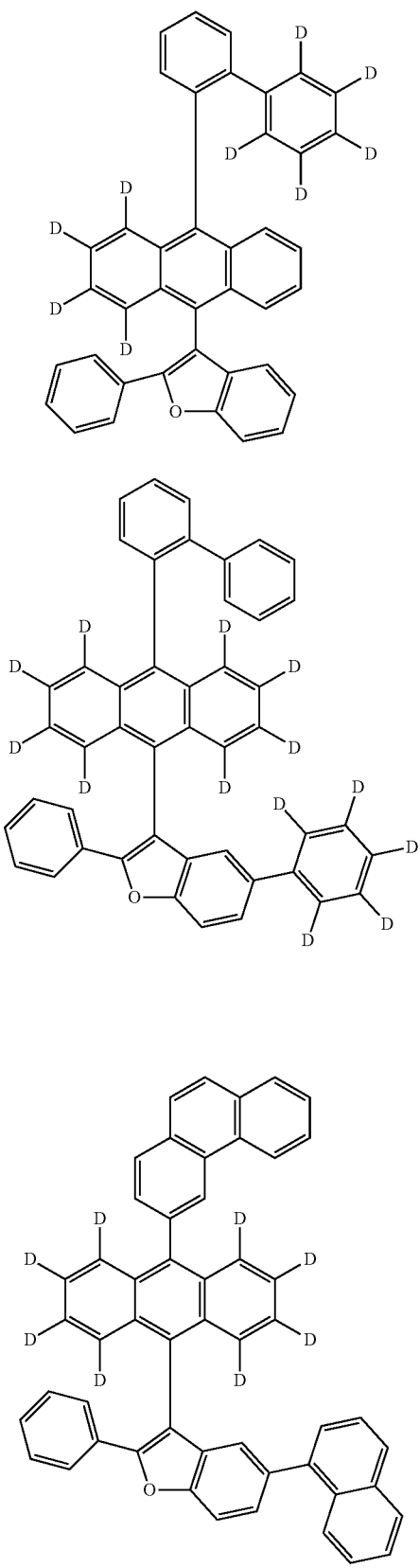
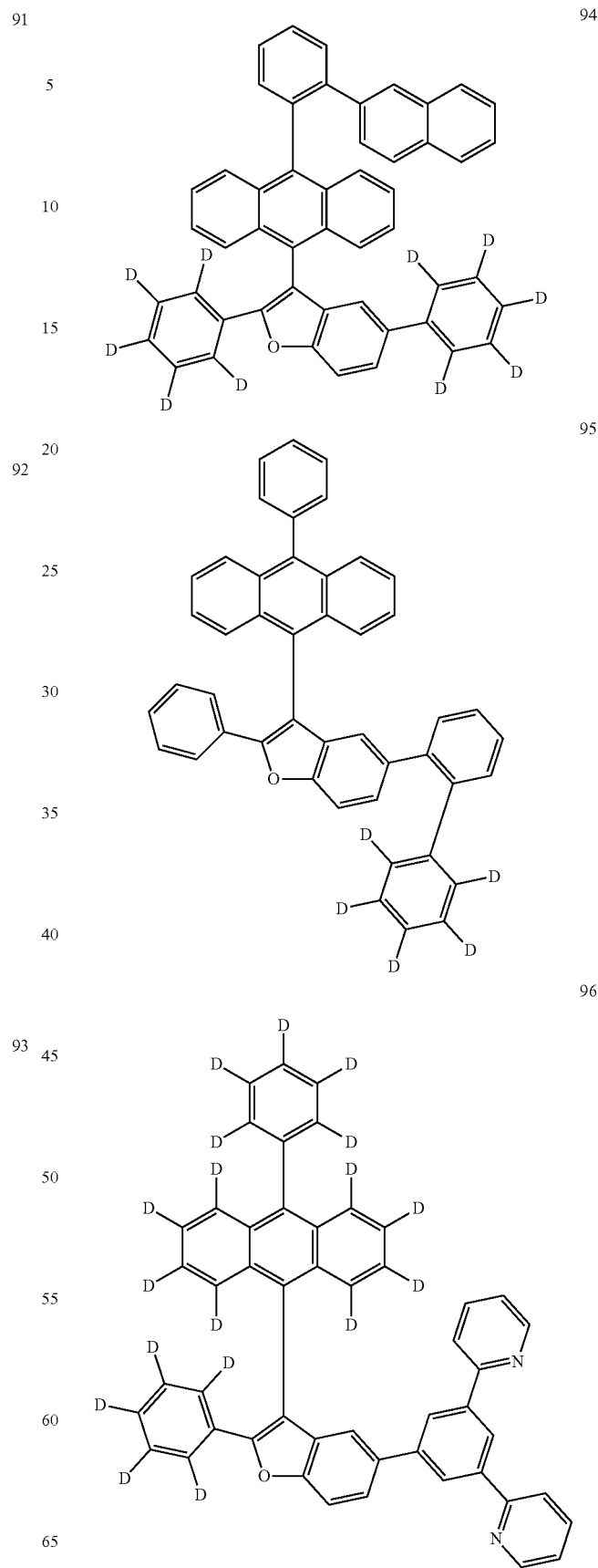

97 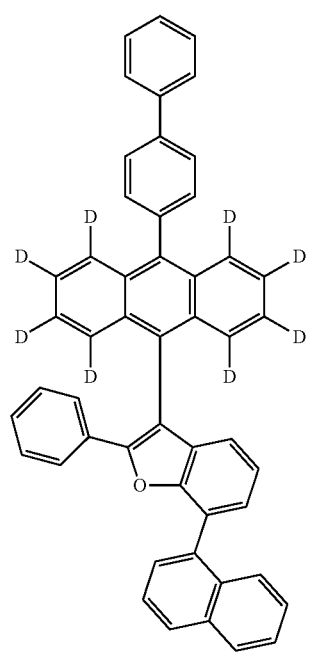
98 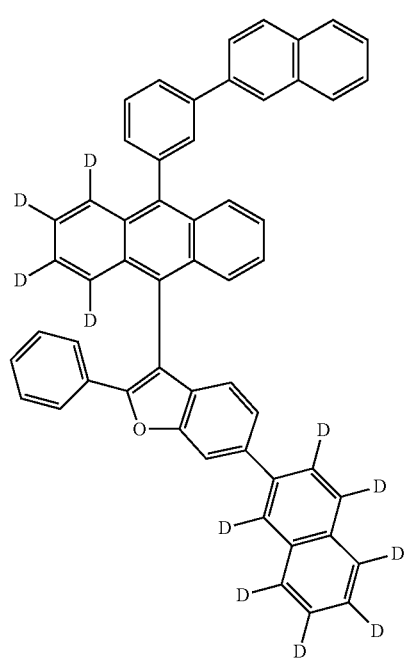
99 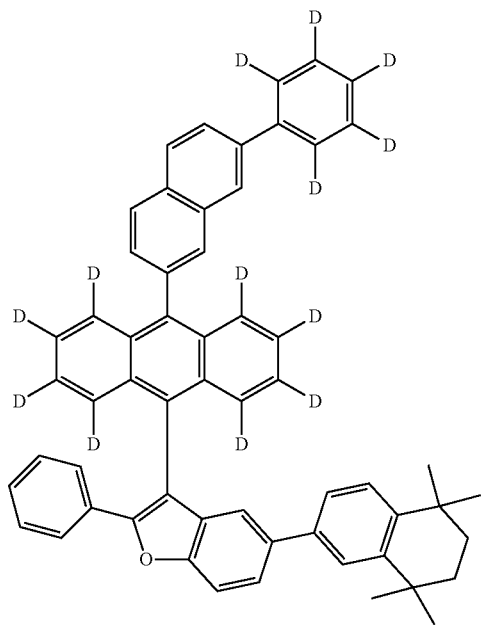
100 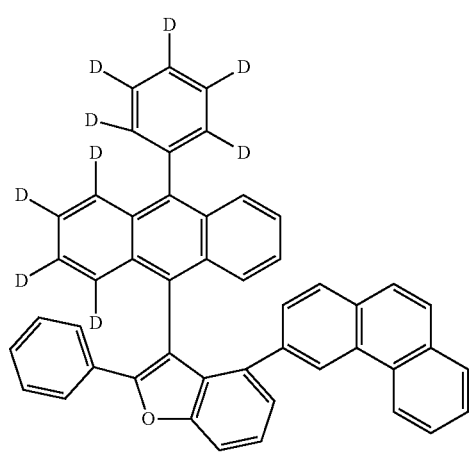

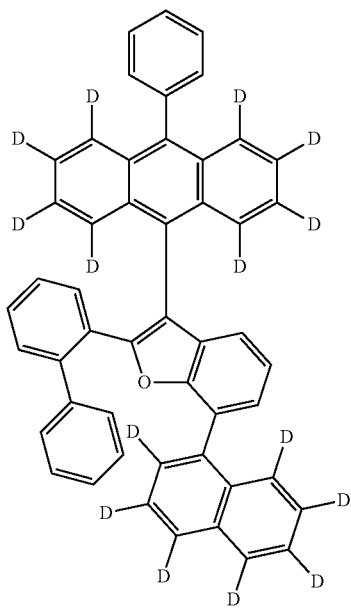

101

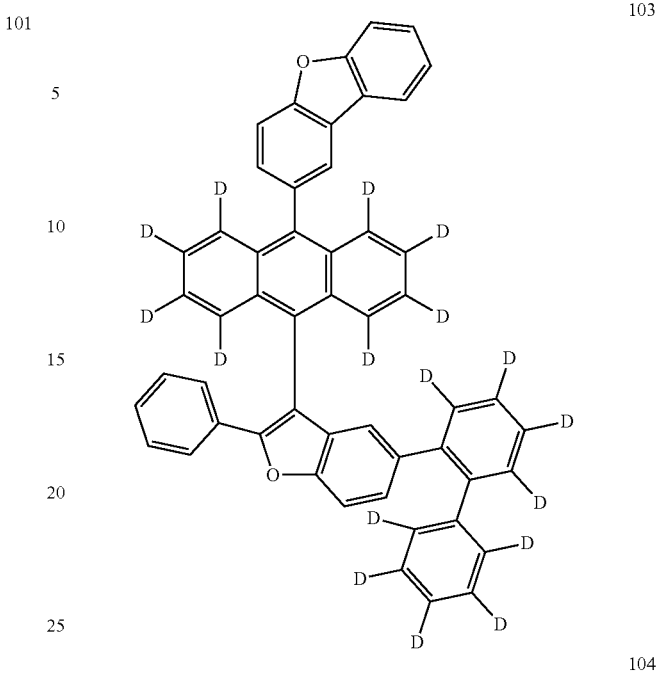

103

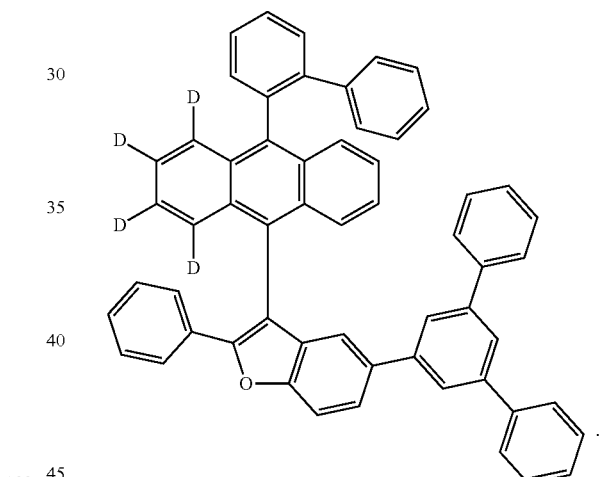

104

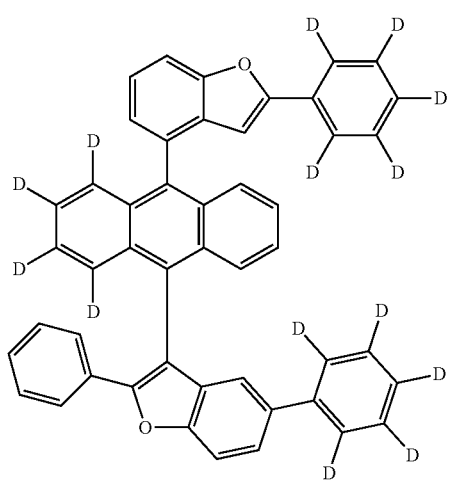

102

2. An organic electroluminescent device comprising a first electrode, a second electrode opposite to the first electrode, and one or more organic layers interposed between the first and second electrodes wherein one of the organic layers comprises the anthracene derivative according to claim 1.

3. The organic electroluminescent device according to claim 2, wherein the organic layers comprise one or more layers selected from a hole injecting layer, a hole transport layer, a functional layer having functions of both hole injection and hole transport, a light emitting layer, an electron transport layer, and an electron injecting layer.

4. The organic electroluminescent device according to claim 3, wherein one of the organic layers interposed between the first and second electrodes is a light emitting layer composed of a host and a dopant and the anthracene derivative according to claim 1 is used as the host.

5. The organic electroluminescent device according to claim 4, wherein one or more host compounds other than the host of claim 4 are mixed or stacked in the light emitting layer.

6. The organic electroluminescent device according to claim 4, wherein the dopant is represented by Formula D-1:

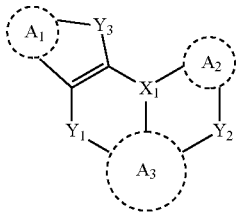

(D-1)

wherein $X_1$ is selected from B, P=O, and P=S, $Y_1$ to $Y_3$ are each independently selected from $NR_{41}$, $CR_{42}R_{43}$, O, S, Se, and $SiR_{44}R_{45}$, $R_{41}$ to $R_{45}$ are identical to or different from each other and are each independently selected from hydrogen, deuterium, substituted or unsubstituted $C_1$-$C_{30}$ alkyl, substituted or unsubstituted $C_6$-$C_{50}$ aryl, substituted or unsubstituted $C_3$-$C_{30}$ cycloalkyl, substituted or unsubstituted $C_3$-$C_{30}$ heterocycloalkyl, substituted or unsubstituted $C_2$-$C_{50}$ heteroaryl, substituted or unsubstituted $C_1$-$C_{30}$ alkoxy, substituted or unsubstituted $C_6$-$C_{30}$ aryloxy, substituted or unsubstituted $C_1$-$C_{30}$ alkylthioxy, substituted or unsubstituted $C_6$-$C_{30}$ arylthioxy, substituted or unsubstituted $C_1$-$C_{30}$ alkylamine, substituted or unsubstituted $C_6$-$C_{30}$ arylamine, substituted or unsubstituted $C_2$-$C_{30}$ heteroarylamine, substituted or unsubstituted $C_1$-$C_{30}$ alkylsilyl, substituted or unsubstituted $C_6$-$C_{30}$ arylsilyl, substituted or unsubstituted $C_3$-$C_{20}$ mixed aliphatic-aromatic cyclic groups, nitro, cyano, and halogen, with the proviso that each of $R_{41}$ to $R_{45}$ is optionally bonded to one or more of the rings $A_1$ to $A_3$ to form an alicyclic or aromatic monocyclic or polycyclic ring and that $R_{42}$ and $R_{43}$ together and $R_{44}$ and $R_{45}$ together optionally form an alicyclic or aromatic monocyclic or polycyclic ring, and $A_1$ to $A_3$ are each independently selected from substituted or unsubstituted $C_6$-$C_{50}$ aromatic hydrocarbon rings, substituted or unsubstituted $C_2$-$C_{50}$ heteroaromatic rings, substituted or unsubstituted $C_3$-$C_{30}$ aliphatic rings, and substituted or unsubstituted $C_3$-$C_{30}$ mixed aliphatic-aromatic cyclic groups, with the proviso that the substituents of each of the rings $A_1$ to $A_3$ together optionally form an alicyclic or aromatic monocyclic or polycyclic ring, the "substituted" in the definition of $A_1$ to $A_3$ and $R_{41}$ to $R_{45}$ indicating substitution with one or more substituents selected from deuterium, cyano, halogen, hydroxyl, nitro, alkyl, haloalkyl, cycloalkyl, alkenyl, alkynyl, heteroalkyl, aryl, arylalkyl, alkylaryl, heteroaryl, heteroarylalkyl, alkoxy, alkylamino, arylamino, heteroarylamino, alkylsilyl, arylsilyl, aryloxy, and mixed aliphatic-aromatic cyclic groups, or Formula D-2:

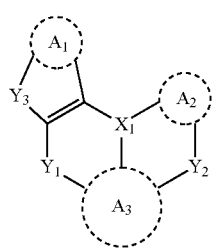

(D-2)

wherein $X_1$, $Y_1$ to $Y_3$, $R_{41}$ to $R_{45}$, and $A_1$ to $A_3$ are as defined in Formula D-1.

7. The organic electroluminescent device according to claim 3, wherein the organic electroluminescent device is used in a display or lighting system selected from flat panel displays, flexible displays, monochromatic flat panel lighting systems, white flat panel lighting systems, flexible monochromatic lighting systems, flexible white lighting systems, displays for automotive applications, displays for virtual reality, and displays for augmented reality.

8. An anthracene derivative represented by Formula A:

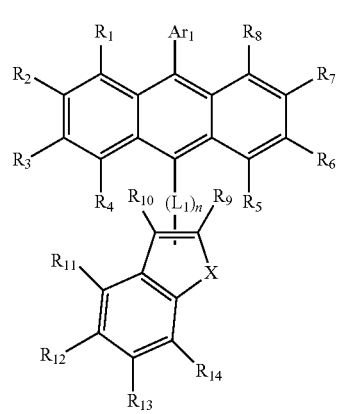

(A)

wherein $Ar_1$ is selected from substituted or unsubstituted $C_6$-$C_{50}$ aryl, substituted or unsubstituted $C_2$-$C_{50}$ heteroaryl, and substituted or unsubstituted $C_3$-$C_{50}$ mixed aliphatic-aromatic cyclic groups, $R_1$ to $R_{14}$ are identical to or different from each other and are each independently selected from hydrogen, deuterium, substituted or unsubstituted $C_1$-$C_{30}$ alkyl, substituted or unsubstituted $C_6$-$C_{50}$ aryl, substituted or unsubstituted $C_2$-$C_{30}$ alkenyl, substituted or unsubstituted $C_2$-$C_{30}$ alkynyl, substituted or unsubstituted $C_3$-$C_{30}$ cycloalkyl, substituted or unsubstituted $C_3$-$C_{30}$ cycloalkenyl, substituted or unsubstituted $C_2$-$C_{50}$ heteroaryl, substituted or unsubstituted $C_2$-$C_{30}$ heterocycloalkyl, substituted or unsubstituted $C_1$-$C_{30}$ alkoxy, substituted or unsubstituted $C_6$-$C_{50}$ aryloxy, substituted or unsubstituted $C_1$-$C_{30}$ alkylthioxy, substituted or unsubstituted $C_6$-$C_{50}$ arylthioxy, substituted or unsubstituted $C_1$-$C_{30}$ alkylamine, substituted or unsubstituted $C_6$-$C_{50}$ arylamine, substituted or unsubstituted $C_1$-$C_{30}$ alkylsilyl, substituted or unsubstituted $C_6$-$C_{50}$ arylsilyl, substituted or unsubstituted $C_3$-$C_{50}$ mixed aliphatic-aromatic cyclic groups, cyano, nitro, and halogen, with the proviso that one of $R_9$ and $R_{50}$ is bonded to $L_1$, X is sulfur atom(S), $L_1$ is a divalent linker and is a single bond or is selected from substituted or unsubstituted $C_6$-$C_{50}$ arylene, substituted or unsubstituted $C_2$-$C_{50}$ heteroarylene, and substituted or unsubstituted $C_3$-$C_{50}$ mixed aliphatic-aromatic cyclic groups, and n is an integer from 1 to 3, provided that when n is 2 or more, the linkers $L_1$ are identical to or different from each other, the "substituted" in the definition of $Ar_1$, $R_1$ to $R_{14}$, and Li indicating substitution with one or more substituents selected from deuterium, cyano, halogen, hydroxyl, nitro, alkyl, haloalkyl, cycloalkyl, alkenyl, alkynyl, heteroalkyl, aryl, arylalkyl, alkylaryl, heteroaryl, heteroarylalkyl, alkoxy, alkylamino, arylamino, heteroarylamino, alkylsilyl, arylsilyl, aryloxy, and mixed aliphatic-aromatic cyclic groups, and wherein the anthracene derivative represented by Formula A comprises at least one deuterium atom (D).

9. The anthracene derivative according to claim 8, wherein the anthracene derivative represented by Formula A is a compound represented by Formula A-1:

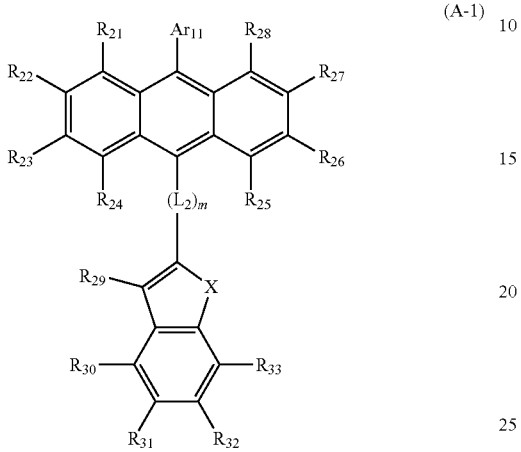

(A-1)

wherein $Ar_{11}$ is selected from substituted or unsubstituted $C_6$-$C_{50}$ aryl, substituted or unsubstituted $C_2$-$C_{50}$ heteroaryl, and substituted or unsubstituted $C_3$-$C_{50}$ mixed aliphatic-aromatic cyclic groups, $R_{21}$ to $R_{33}$ are identical to or different from each other and are each independently selected from hydrogen, deuterium, substituted or unsubstituted $C_1$-$C_{30}$ alkyl, substituted or unsubstituted $C_6$-$C_{50}$ aryl, substituted or unsubstituted $C_2$-$C_{30}$ alkenyl, substituted or unsubstituted $C_2$-$C_{30}$ alkynyl, substituted or unsubstituted $C_3$-$C_{30}$ cycloalkyl, substituted or unsubstituted $C_3$-$C_{30}$ cycloalkenyl, substituted or unsubstituted $C_2$-$C_{50}$ heteroaryl, substituted or unsubstituted $C_2$-$C_{30}$ heterocycloalkyl, substituted or unsubstituted $C_1$-$C_{30}$ alkoxy, substituted or unsubstituted $C_6$-$C_{50}$ aryloxy, substituted or unsubstituted $C_1$-$C_{30}$ alkylthioxy, substituted or unsubstituted $C_6$-$C_{50}$ arylthioxy, substituted or unsubstituted $C_1$-$C_{30}$ alkylamine, substituted or unsubstituted $C_6$-$C_{50}$ arylamine, substituted or unsubstituted $C_1$-$C_{30}$ alkylsilyl, substituted or unsubstituted $C_6$-$C_{50}$ arylsilyl, substituted or unsubstituted $C_3$-$C_{50}$ mixed aliphatic-aromatic cyclic groups, cyano, nitro, and halogen, X is sulfur atom(S), $L_2$ is a divalent linker and is a single bond or is selected from substituted or unsubstituted $C_6$-$C_{50}$ arylene, substituted or unsubstituted $C_2$-$C_{50}$ heteroarylene, and substituted or unsubstituted $C_3$-$C_{50}$ mixed aliphatic-aromatic cyclic groups, and m is an integer from 1 to 3, provided that when m is 2 or more, the linkers $L_1$ are identical to or different from each other, the "substituted" in the definition of $Ar_{11}$, $R_{21}$ to $R_{33}$, and $L_2$ indicating substitution with one or more substituents selected from deuterium, cyano, halogen, hydroxyl, nitro, alkyl, haloalkyl, cycloalkyl, alkenyl, alkynyl, heteroalkyl, aryl, arylalkyl, alkylaryl, heteroaryl, heteroarylalkyl, alkoxy, alkylamino, arylamino, heteroarylamino, alkylsilyl, arylsilyl, aryloxy, and mixed aliphatic-aromatic cyclic groups, or Formula A-2:

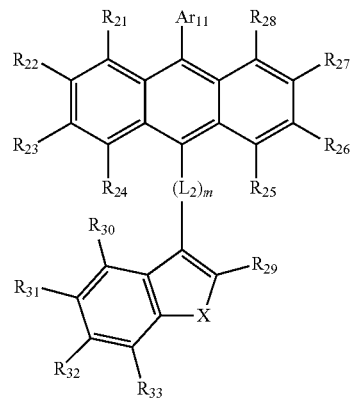

(A-2)

wherein $Ar_{11}$, $R_{21}$ to $R_{33}$, X, $L_2$, and m are as defined in Formula A-1, and wherein each of the compounds represented by Formulae A-1 and A-2 comprises at least one deuterium atom (D).

10. The anthracene derivative according to claim 8, wherein at least one of $R_{11}$ to $R_{14}$ in Formula A is selected from substituted or unsubstituted $C_6$-$C_{20}$ aryl, substituted or unsubstituted $C_3$-$C_{20}$ cycloalkyl, and substituted or unsubstituted $C_3$-$C_{20}$ heteroaryl.

11. The anthracene derivative according to claim 10, wherein at least one of $R_{11}$ to $R_{14}$ in Formula A is substituted or unsubstituted deuterated $C_6$-$C_{20}$ aryl, substituted or unsubstituted deuterated $C_3$-$C_{20}$ cycloalkyl or substituted or unsubstituted deuterated $C_3$-$C_{20}$ heteroaryl.

12. The anthracene derivative according to claim 9, wherein each of $R_{29}$ in Formula A-1 and $R_{29}$ in Formula A-2 is substituted or unsubstituted deuterated $C_6$-$C_{20}$ aryl, substituted or unsubstituted deuterated $C_3$-$C_{20}$ cycloalkyl or substituted or unsubstituted deuterated $C_3$-$C_{20}$ heteroaryl which comprises at least one deuterium atom (D).

13. The anthracene derivative according to claim 8, wherein the degree of deuteration of the anthracene derivative represented by Formula A is at least 10%.

14. The anthracene derivative according to claim 8, wherein the degree of deuteration of the anthracene derivative represented by Formula A is at least 30%.

15. An organic electroluminescent device comprising a first electrode, a second electrode opposite to the first electrode, and one or more organic layers interposed between the first and second electrodes wherein one of the organic layers comprises the anthracene derivative according to claim 8.

16. The organic electroluminescent device according to claim 15, wherein the organic layers comprise one or more layers selected from a hole injecting layer, a hole transport layer, a functional layer having functions of both hole injection and hole transport, a light emitting layer, an electron transport layer, and an electron injecting layer.

17. The organic electroluminescent device according to claim 16, wherein one of the organic layers interposed between the first and second electrodes is a light emitting layer composed of a host and a dopant and the anthracene derivative is used as the host.

18. The organic electroluminescent device according to claim 17, wherein one or more host compounds other than the host 24 are mixed or stacked in the light emitting layer.

19. The organic electroluminescent device according to claim 17, wherein the dopant is represented by Formula D-1:

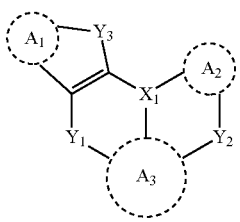

(D-1)

wherein $X_1$ is selected from B, P=O, and P=S, Y, to $Y_3$ are each independently selected from $NR_{41}$, $CR_{42}R_{43}$, O, S, Se, and $SiR_{44}R_{45}$, $R_{41}$ to $R_{45}$ are identical to or different from each other and are each independently selected from hydrogen, deuterium, substituted or unsubstituted $C_1$-$C_{30}$ alkyl, substituted or unsubstituted $C_6$-$C_{50}$ aryl, substituted or unsubstituted $C_3$-$C_{30}$ cycloalkyl, substituted or unsubstituted $C_3$-$C_{30}$ heterocycloalkyl, substituted or unsubstituted $C_2$-$C_{50}$ heteroaryl, substituted or unsubstituted $C_1$-$C_{30}$ alkoxy, substituted or unsubstituted $C_6$-$C_{30}$ aryloxy, substituted or unsubstituted $C_1$-$C_{30}$ alkylthioxy, substituted or unsubstituted $C_6$-$C_{30}$ arylthioxy, substituted or unsubstituted $C_1$-$C_{30}$ alkylamine, substituted or unsubstituted $C_6$-$C_{30}$ arylamine, substituted or unsubstituted $C_2$-$C_{30}$ heteroarylamine, substituted or unsubstituted $C_1$-$C_{30}$ alkylsilyl, substituted or unsubstituted $C_6$-$C_{30}$ arylsilyl, substituted or unsubstituted $C_3$-$C_{20}$ mixed aliphatic-aromatic cyclic groups, nitro, cyano, and halogen, with the proviso that each of $R_{41}$ to $R_{45}$ is optionally bonded to one or more of the rings $A_1$ to $A_3$ to form an alicyclic or aromatic monocyclic or polycyclic ring and that $R_{42}$ and $R_{43}$ together and $R_{44}$ and $R_{45}$ together optionally form an alicyclic or aromatic monocyclic or polycyclic ring, and $A_1$ to $A_3$ are each independently selected from substituted or unsubstituted $C_6$-$C_{50}$ aromatic hydrocarbon rings, substituted or unsubstituted $C_2$-$C_{50}$ heteroaromatic rings, substituted or unsubstituted $C_3$-$C_{30}$ aliphatic rings, and unsubstituted or unsubstituted $C_3$-$C_{30}$ mixed aliphatic-aromatic cyclic groups, with the proviso that the substituents of each of the rings $A_1$ to $A_3$ together optionally form an alicyclic or aromatic monocyclic or polycyclic ring, the "substituted" in the definition of $A_1$ to $A_3$ and $R_{41}$ to $R_{45}$ indicating substitution with one or more substituents selected from deuterium, cyano, halogen, hydroxyl, nitro, alkyl, haloalkyl, cycloalkyl, alkenyl, alkynyl, heteroalkyl, aryl, arylalkyl, alkylaryl, heteroaryl, heteroarylalkyl, alkoxy, alkylamino, arylamino, heteroarylamino, alkylsilyl, arylsilyl, aryloxy, and mixed aliphatic-aromatic cyclic groups, or Formula D-2:

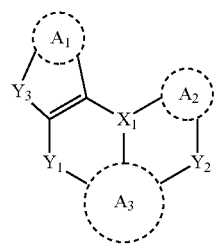

(D-2)

wherein $X_1$, $Y_1$ to $Y_3$, $R_{41}$ to $R_{45}$, and $A_1$ to $A_3$ are as defined in Formula D-1.

20. The organic electroluminescent device according to claim 16, wherein the organic electroluminescent device is used in a display or lighting system selected from flat panel displays, flexible displays, monochromatic flat panel lighting systems, white flat panel lighting systems, flexible monochromatic lighting systems, flexible white lighting systems, displays for automotive applications, displays for virtual reality, and displays for augmented reality.

* * * * *